(12) United States Patent
Chen et al.

(10) Patent No.: US 11,655,212 B2
(45) Date of Patent: May 23, 2023

(54) USING ADIPONECTIN RECEPTOR AGONISTS TO TREAT INFLAMMATION AND BONE DISEASES IN DIABETES

(71) Applicant: Trustees of Tufts College, Medford, MA (US)

(72) Inventors: Jinkun Chen, Lexington, MA (US); Qisheng Tu, Newton, MA (US); Xingwen Wu, Boston, MA (US); Gang Chen, Shanghai (CN); Wei Qiu, Boston, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 17/550,834

(22) Filed: Dec. 14, 2021

(65) Prior Publication Data

US 2022/0185777 A1 Jun. 16, 2022

Related U.S. Application Data

(60) Provisional application No. 63/125,362, filed on Dec. 14, 2020.

(51) Int. Cl.
*C07D 211/58* (2006.01)
*A61P 29/00* (2006.01)
*A61P 19/08* (2006.01)

(52) U.S. Cl.
CPC ............ *C07D 211/58* (2013.01); *A61P 19/08* (2018.01); *A61P 29/00* (2018.01)

(58) Field of Classification Search
CPC ......... C07D 211/58; A61P 19/08; A61P 29/00
See application file for complete search history.

(56) References Cited

U.S. PATENT DOCUMENTS

2005/0250792 A1* 11/2005 Thom .................... A61P 25/00
514/355

OTHER PUBLICATIONS

Curtis, Michael J. et al. "Experimental design and analysis and their reporting II: Updated and simplified guidance for authors and peer reviewers." British journal of pharmacology 175, No. 7 (2018): 987-993.
Daassi, Dhouha et al. "Differential expression patterns of MafB and c-Maf in macrophages in vivo and in vitro." Biochemical and biophysical research communications 473, No. 1 (2016): 118-124.
Deepa, Sathyaseelan S. et al. "APPL1: role in adiponectin signaling and beyond." American Journal of Physiology-Endocrinology and Metabolism 296, No. 1 (2009): E22-E36.
Diggins, Nicole L. et al. "APPL1 is a multifunctional endosomal signaling adaptor protein." Biochemical Society Transactions 45, No. 3 (2017): 771-779.
Du, Meng et al. "The LPS-inducible lncRNA Mirt2 is a negative regulator of inflammation." Nature communications 8, No. 1 (2017): 1-18.
Folco, Eduardo J. et al. "Adiponectin inhibits pro-inflammatory signaling in human macrophages independent of interleukin-10." Journal of Biological chemistry 284, No. 38 (2009): 25569-25575.
Foster, Simmie L. et al. "Gene-specific control of the TLR-induced inflammatory response." Clinical immunology 130, No. 1 (2009): 7-15.
Hirotani, Tomonori et al. "Regulation of lipopolysaccharide-inducible genes by MyD88 and Toll/IL-1 domain containing adaptor inducing IFN-β." Biochemical and biophysical research communications 328, No. 2 (2005): 383-392.
Kilkenny, Carol et al. "Animal research: reporting in vivo experiments: the ARRIVE guidelines." British journal of pharmacology 160, No. 7 (2010): 1577.
Kawai, Taro et al. "The role of pattern-recognition receptors in innate immunity: update on Toll-like receptors." Mature immunology 11, No. 5 (2010): 373-384.
Kim, James L. et al. "The transcription factor c-Maf controls the production of interleukin-4 but not other Th2 cytokines." Immunity 10, No. 6 (1999): 745-751.
Kim, Mi Jin et al. "Globular adiponectin inhibits lipopolysaccharide-primed inflammasomes activation in macrophages via autophagy induction: the critical role of AMPK signaling." International journal of molecular sciences 18, No. 6 (2017): 1275.
Kishimoto, Kazuya et al. "TAK1 mitogen-activated protein kinase kinase kinase is activated by autophosphorylation within its activation loop." Journal of Biological Chemistry 275, No. 10 (2000): 7359-7364.
Kobashi, Chikaaki et al. "Adiponectin inhibits endothelial synthesis of interleukin-8." Circulation research 97, No. 12 (2005): 1245-1252.
Kumada, Masahiro et al. "Adiponectin specifically increased tissue inhibitor of metalloproteinase-1 through interleukin-10 expression in human macrophages." Circulation 109, No. 17 (2004): 2046-2049.
Lamothe, Betty et al. "Site-specific Lys-63-linked tumor necrosis factor receptor-associated factor 6 auto-ubiquitination is a critical determinant of IκB kinase activation." Journal of Biological Chemistry 282, No. 6 (2007): 4102-4112.
Lian, Junxiang et al. "Potential roles of miR-335-5p on pathogenesis of experimental periodontitis." Journal of periodontal research 55, No. 2 (2020): 191-198.
Lovren, Fina et al. "Adiponectin primes human monocytes into alternative anti-inflammatory M2 macrophages." American Journal of Physiology-Heart and Circulatory Physiology 299, No. 3 (2010): H656-H663.
Mandal, Palash et al. "The anti-inflammatory effects of adiponectin are mediated via a heme oxygenase-1-dependent pathway in rat Kupffer cells." Hepatology 51, No. 4 (2010): 1420-1429.
Mandal, Palash et al. "Molecular mechanism for adiponectin-dependent M2 macrophage polarization: link between the metabolic and innate immune activity of full-length adiponectin." Journal of Biological Chemistry 286, No. 15 (2011): 13460-13469.

(Continued)

*Primary Examiner* — Timothy R Rozof
(74) *Attorney, Agent, or Firm* — Quarles & Brady LLP

(57) ABSTRACT

Disclosed herein are adiponectin receptor agonists and methods of using the same for the treatment of inflammation or bone loss in a subject.

20 Claims, 69 Drawing Sheets

Specification includes a Sequence Listing.

(56) References Cited

OTHER PUBLICATIONS

Mao, Liufeng et al. "Absence of Appl2 sensitizes endotoxin shock through activation of PI3K/Akt pathway." Cell & Bioscience 4, No. 1 (2014): 1-10.
Mao, Xuming et al. "APPL1 binds to adiponectin receptors and mediates adiponectin signalling and function." Nature cell biology 8, No. 5 (2006): 516-523.
Masamoto, Yosuke et al. "Adiponectin enhances antibacterial activity of hematopoietic cells by suppressing bone marrow inflammation." Immunity 44, No. 6 (2016): 1422-1433.
McGrath, John C. et al. "Implementing guidelines on reporting research using animals (ARRIVE etc.): new requirements for publication in BJP." British journal of pharmacology 172, No. 13 (2015): 3189-3193.
Medzhitov, Ruslan et al. "Transcriptional control of the inflammatory response." Nature Reviews Immunology 9, No. 10 (2009): 692-703.
Murray, Peter J. et al. "Macrophage activation and polarization: nomenclature and experimental guidelines." Immunity 41, No. 1 (2014): 14-20.
Murray, Peter J. et al. "Restraint of inflammatory signaling by interdependent strata of negative regulatory pathways." Nature immunology 13, No. 10 (2012): 916-924.
Nicolas S. et al. "Adiponectin: an endogenous molecule with anti-inflammatory and antidepressant properties?". Med Sci (Paris). May 2018;34(5):417-423. French, doi: 10.1051/medsci/20183405014. Epub Jun. 13, 2018. PMID: 29900844.
Harding, Simon D. et al. "The IUPHAR/BPS Guide to Pharmacology in 2018: updates and expansion to encompass the new guide to Immunopharmacology." Nucleic acids research 46, No. D1 (2018): D1091-D1106.
Ohashi, Koji et al. "Adiponectin promotes macrophage polarization toward an anti-inflammatory phenotype." Journal of Biological Chemistry 285, No. 9 (2010): 6153-6160.
Okada-Iwabu, Miki et al. "A small-molecule AdipoR agonist for type 2 diabetes and short life in obesity." Nature 503, No. 7477 (2013): 493-499.
Ouchi, Noriyuki et al. "Adiponectin as an anti-inflammatory factor." Clinica chimica acta 380, No. 1-2 (2007): 24-30.
Piao, Wenji et al. "Endotoxin tolerance dysregulates MyD88-and Toll/IL-1R domain-containing adapter inducing IFN-β-dependent pathways and increases expression of negative regulators of TLR signaling." Journal of leukocyte biology 86, No. 4 (2009): 863-875.
Tilija Pun et al. "Globular adiponectin causes tolerance to LPS-induced TNF-α expression via autophagy induction in RAW 264.7 macrophages: involvement of SIRT1/FoxO3A axis" PloS one 10, No. 5 (2015): e0124636.
Salomao, Reinaldo et al. "Bacterial sensing, cell signaling, and modulation of the immune response during sepsis." Shock 38, No. 3 (2012): 227-242.
Sattar, Naveed et al. "Adiponectin and coronary heart disease: a prospective study and meta-analysis." Circulation 114, No. 7 (2006): 623-629.
Skaug, Brian et al. "The role of ubiquitin in NF-κB regulatory pathways." Annual review of biochemistry 78 (2009): 769-796.
Thakur, Varsha et al. "Adiponectin normalizes LPS-stimulated TNF-α production by rat Kupffer cells after chronic ethanol feeding." American Journal of Physiology—Gastrointestinal and Liver Physiology 290, No. 5 (2006): G998-G1007.
Tilija Pun et al. "Adiponectin inhibits inflammatory cytokines production by Beclin-1 phosphorylation and B-cell lymphoma 2 mRNA destabilization: role for autophagy induction." British Journal of Pharmacology 175, No. 7 (2018): 1066-1084.
Tu, Qisheng et al. "Adiponectin inhibits osteoclastogenesis and bone resorption via APPL1-mediated suppression of Akt1." Journal of Biological Chemistry 286, No. 14 (2011): 12542-12553.
Van Den Bosch, Mirjam WM et al. "LPS induces the degradation of programmed cell death protein 4 (PDCD4) to release Twist2, activating c-Maf transcription to promote interleukin-10 production." Journal of Biological Chemistry 289, No. 33 (2014): 22980-22990.
Wang, Nan et al. "Molecular mechanisms that influence the macrophage M1-M2 polarization balance." Frontiers in immunology 5 (2014): 614.
Wess, Jurgen "G-protein-coupled receptors: molecular mechanisms involved in receptor activation and selectivity of G-protein recognition." The FASEB Journal 11, No. 5 (1997): 346-354.
Wolf, Anna M. et al. "Adiponectin induces the anti-inflammatory cytokines IL-10 and IL-1RA in human leukocytes." Biochemical and biophysical research communications 323, No. 2 (2004): 630-635.
Wu, X. et al. "An adiponectin receptor agonist reduces type 2 diabetic periodontitis." Journal of dental research 98, No. 3 (2019): 313-321.
Wulster-Radcliffe, Meghan C. et al. "Adiponectin differentially regulates cytokines in porcine macrophages." Biochemical and biophysical research communications 316, No. 3 (2004): 924-929.
Xie, Qing et al. "Regulation of c-Maf and αA-crystallin in ocular lens by fibroblast growth factor signaling." Journal of Biological Chemistry 291, No. 8 (2016): 3947-3958.
Xu, Mo et al. "c-MAF-dependent regulatory T cells mediate immunological tolerance to a gut pathobiont." Nature 554, No. 7692 (2018): 373-377.
Xuan, Dongying et al. "Epigenetic modulation in periodontitis: interaction of adiponectin and JMJD3-IRF4 axis in macrophages." Journal of cellular physiology 231, No. 5 (2016): 1090-1096.
Yamaguchi, Noboru et al. "Adiponectin inhibits Toll-like receptor family-induced signaling." FEBS letters 579, No. 30 (2005): 6821-6826.
Yamauchi, Toshimasa et al. "Cloning of adiponectin receptors that mediate antidiabetic metabolic effects." Nature 423, No. 6941 (2003): 762-769.
Yokota, Takafumi et al. "Adiponectin, a new member of the family of soluble defense collagens, negatively regulates the growth of myelomonocytic progenitors and the functions of macrophages." Blood, The Journal of the American Society of Hematology 96, No. 5 (2000): 1723-1732.
Zhang, Jin et al. "Exercise-induced irisin in bone and systemic irisin administration reveal new regulatory mechanisms of bone metabolism." Bone research 5, No. 1 (2017): 1-14.
Zhang, Lan et al. "Adiponectin ameliorates experimental periodontitis in diet-induced obesity mice." PloS one 9, No. 5 (2014): e97824.
U.S. Appl. No. 63/125,362, filed Dec. 14, 2020, Trustees of Trfts College.
Nesse, Willem et al. "Increased prevalence of cardiovascular and autoimmune diseases in periodontitis patients: A cross-sectional study." Journal of periodontology 81, No. 11 (2010): 1622-1628.
Nibali, Luigi et al. "Association between metabolic syndrome and periodontitis: a systematic review and meta-analysis." The Journal of Clinical Endocrinology & Metabolism 98, No. 3 (2013): 913-920.
Zhou, Xuan et al. "Effects of periodontal treatment on lung function and exacerbation frequency in patients with chronic obstructive pulmonary disease and chronic periodontitis: A 2-year pilot randomized controlled trial." Journal of clinical periodontology 41, No. 6 (2014): 564-572.
Preshaw, P. M. et al. "Periodontitis and diabetes: a two-way relationship." Diabetologia 55, No. 1 (2012): 21-31.
Sanz, Mariano et al. "Scientific evidence on the links between periodontal diseases and diabetes: Consensus report and guidelines of the joint workshop on periodontal diseases and diabetes by the International Diabetes Federation and the European Federation of Periodontology." Diabetes research and clinical practice 137 (2018): 231-241.
Ainamo, J. et al. "Rapid periodontal destruction in adult humans with poorly controlled diabetes A report of 2 cases." Journal of Clinical Periodontology 17, No. 1 (1990): 22-28.
Seppälä, B. et al. "A site-by-site follow-up study on the effect of controlled versus poorly controlled insulin-dependent diabetes mellitus." Journal of clinical periodontology 21, No. 3 (1994): 161-165.

(56) References Cited

OTHER PUBLICATIONS

Sima, Corneliu et al. "Therapeutic targets for management of periodontitis and diabetes." Current pharmaceutical design 22, No. 15 (2016): 2216-2237.
Eke, Paul I. et al. "Prevalence of periodontitis in adults in the United States: 2009 and 2010." Journal of dental research 91, No. 10 (2012): 914-920.
Graves, D. T. et al. "Inflammation and uncoupling as mechanisms of periodontal bone loss." Journal of dental research 90, No. 2 (2011): 143-153.
Liu, Rongkun et al. "Diabetes enhances periodontal bone loss through enhanced resorption and diminished bone formation." Journal of dental research 85, No. 6 (2006): 510-514.
Wu, Yi et al. "MicroRNA-126 regulates inflammatory cytokine secretion in human gingival fibroblasts under high glucose via targeting tumor necrosis factor receptor associated factor 6." Journal of periodontology 88, No. 11 (2017): e179-e187.
Tang, Yin et al. "Porphyromonas endodontalis lipopolysaccharides induce RANKL by mouse osteoblast in a way different from that of *Escherichia coli* lipopolysaccharide." Journal of endodontics 37, No. 12 (2011): 1653-1658.
Yin, Xing et al. "Autophagy in bone homeostasis and the onset of osteoporosis." Bone research 7, No. 1 (2019): 1-16.
Djajadikerta, Alvin et al. "Autophagy induction as a therapeutic strategy for neurodegenerative diseases." Journal of molecular biology 432, No. 8 (2020): 2799-2821.
Mizushima, Noboru. "Autophagy: process and function." Genes & development 21, No. 22 (2007): 2861-2873.
Wang, Lei et al. "Netrin-1 regulates ERK1/2 signaling pathway and autophagy activation in wear particle-induced osteoclastogenesis." Cell Biology International 45, No. 3 (2021): 612-622.
Pierrefite-Carle, Valerie et al. "Autophagy in bone: self-eating to stay in balance." Ageing Research Reviews 24 (2015): 206-217.
Tong, Xishuai et al. "Osteoprotegerin inhibit osteoclast differentiation and bone resorption by enhancing autophagy via AMPK/mTOR/p70S6K signaling pathway in vitro." Journal of Cellular Biochemistry 120, No. 2 (2019): 1630-1642.
Boyce, Brendan F. et al. "Functions of RANKL/RANK/OPG in bone modeling and remodeling." Archives of biochemistry and biophysics 473, No. 2 (2008): 139-146.
Li, Rui-Fang et al. "The adaptor protein p62 is involved in RANKL-induced autophagy and osteoclastogenesis." Journal of Histochemistry & Cytochemistry 62, No. 12 (2014): 879-888.
Montaseri, Azadeh et al. "The role of autophagy in osteoclast differentiation and bone resorption function." Biomolecules 10, No. 10 (2020): 1398.
Qiu, Wei et al. "Identification and characterization of a novel adiponectin receptor agonist adipo anti-inflammation agonist and its anti-inflammatory effects in vitro and in vivo." British journal of pharmacology 178, No. 2 (2021): 280-297.
Li, Ruixue et al. "Effect of GARP on osteogenic differentiation of bone marrow mesenchymal stem cells via the regulation of TGFβ1 in vitro." PeerJ 7 (2019): e6993.
Chen, Jin-Fei et al. "STAT3-induced lncRNA HAGLROS overexpression contributes to the malignant progression of gastric cancer cells via mTOR signal-mediated inhibition of autophagy." Molecular cancer 17, No. 1 (2018): 1-16.
Zhang, Yanqing et al. "AdipoRon, the first orally active adiponectin receptor activator, attenuates postischemic myocardial apoptosis through both AMPK-mediated and AMPK-independent signalings." American Journal of Physiology-Endocrinology and Metabolism 309, No. 3 (2015): E275-E282.
Kim, Yaeni et al. "The adiponectin receptor agonist AdipoRon ameliorates diabetic nephropathy in a model of type 2 diabetes." Journal of the American Society of Nephrology 29, No. 4 (2018): 1108-1127.
Dikic, Ivan et al. "Mechanism and medical implications of mammalian autophagy." Nature reviews Molecular cell biology 19, No. 6 (2018): 349-364.
Hansen, Malene et al. "Autophagy as a promoter of longevity: insights from model organisms." Nature reviews Molecular cell biology 19, No. 9 (2018): 579-593.
Xu, Aimin et al. "Emerging role of autophagy in mediating widespread actions of ADIPOQ/adiponectin." Autophagy 11, No. 4 (2015): 723-724.
Liu, Ying et al. "Adiponectin stimulates autophagy and reduces oxidative stress to enhance insulin sensitivity during high-fat diet feeding in mice." Diabetes 64, No. 1 (2015): 36-48.
Ahlstrom, Penny et al. "Adiponectin improves insulin sensitivity via activation of autophagic flux." Journal of molecular endocrinology 59, No. 4 (2017): 339-350.
Hocking, Lynne J. et al. "Autophagy: a new player in skeletal maintenance?." Journal of Bone and Mineral Research 27, No. 7 (2012): 1439-1447.
Sanchez, Cheryl P. et al. "Bone growth during rapamycin therapy in young rats." BMC pediatrics 9, No. 1 (2009): 1-13.
Smink, Jeske J. et al. "Rapamycin inhibits osteoclast formation in giant cell tumor of bone through the C/EBPβ-MafB axis." Journal of molecular medicine 90, No. 1 (2012): 25-30.
Aderem, Alan et al. "Toll-like receptors in the induction of the innate immune response." Nature 406, No. 6797 (2000): 782-787.
Alexander, Steve PH et al. "Goals and practicalities of immunoblotting and immunohistochemistry: A guide for submission to the British Journal of Pharmacology." British journal of pharmacology 175, No. 3 (2018): 407.
Alexander, Steve PH et al. "The Concise Guide to Pharmacology 2019/20: Introduction and other protein targets." British journal of pharmacology 176 (2019): S1-S20.
Barton, Gregory M. "A calculated response: control of inflammation by the innate immune system." The Journal of clinical investigation 118, No. 2 (2008): 413-420.
Brochu-Gaudreau, Karine et al. "Adiponectin action from head to toe." Endocrine 37, No. 1 (2010): 11-32.
Bruce, Clinton R. et al. "The stimulatory effect of globular adiponectin on insulin-stimulated glucose uptake and fatty acid oxidation is impaired in skeletal muscle from obese subjects." Diabetes 54, No. 11 (2005): 3154-3160.
Cao, Shanjin et al. "The protooncogene c-Maf is an essential transcription factor for IL-10 gene expression in macrophages." The Journal of Immunology 174, No. 6 (2005): 3484-3492.
Chau, Tieu-Lan et al. "A role for APPL1 in TLR3/4-dependent TBK1 and IKKε activation in macrophages." The Journal of Immunology 194, No. 8 (2015): 3970-3983.
Chen, Linlin et al. "Inflammatory responses and inflammation-associated diseases in organs." Oncotarget 9, No. 6 (2018): 7204.
Cheng, Xiang et al. "Adiponectin induces pro-inflammatory programs in human macrophages and CD4+ T cells." Journal of Biological Chemistry 287, No. 44 (2012): 36896 36904.
Curtis, Michael J. et al. "Experimental design and analysis and their reporting: new guidance for publication in BJP." British journal of pharmacology 172, No. 14 (2015): 3461.

\* cited by examiner

| g | AdipoAI+L | LPS | |
|---|---|---|---|
| immune response | 205 | 1153 | 0.177797 |
| immune system process | 289 | 2209 | 0.130828 |
| defense response | 219 | 1378 | 0.159854 |
| response to stress | 336 | 3158 | 0.106464 |
| response to external stimulus | 245 | 1955 | 0.125321 |
| regulation of response to stimulus | 323 | 3171 | 0.101861 |
| positive regulation of biological process | 434 | 5011 | 0.086609 |
| response to cytokine | 117 | 556 | 0.210432 |
| innate immune response | 119 | 598 | 0.199664 |
| regulation of immune system process | 173 | 1183 | 0.146238 |
| inflammatory response | 119 | 601 | 0.198003 |
| regulation of response to stress | 187 | 1124 | 0.148577 |
| regulation of defense response | 112 | 573 | 0.195462 |
| cellular response to cytokine stimulus | 100 | 461 | 0.21692 |
| positive regulation of cellular process | 397 | 4516 | 0.085695 |
| positive regulation of immune system process | 125 | 753 | 0.166003 |
| response to biotic stimulus | 137 | 901 | 0.152053 |
| response to organic substance | 255 | 2502 | 0.101918 |
| cytokine production | 109 | 608 | 0.179868 |
| intracellular signal transduction | 238 | 2257 | 0.10545 |

FIG. 2 (Continued)

| | AdipoAI+L | LPS | |
|---|---|---|---|
| inflammatory response | 49 | 601 | 0.081531 |
| defense response | 69 | 1370 | 0.050365 |
| immune response | 59 | 1153 | 0.051171 |
| immune system process | 83 | 2209 | 0.037574 |
| response to stress | 96 | 3156 | 0.030418 |
| regulation of immune system process | 51 | 1183 | 0.043111 |
| positive regulation of immune system process | 39 | 753 | 0.051793 |
| cell chemotaxis | 22 | 239 | 0.09205 |
| response to external stimulus | 67 | 1955 | 0.034271 |
| response to cytokine | 31 | 556 | 0.055755 |
| leukocyte migration | 22 | 282 | 0.078014 |
| regulation of multicellular organismal process | 78 | 2711 | 0.028772 |
| regulation of cell proliferation | 53 | 1498 | 0.035381 |
| cellular response to cytokine stimulus | 27 | 461 | 0.058568 |
| leukocyte chemotaxis | 17 | 176 | 0.096591 |
| regulation of inflammatory response | 21 | 281 | 0.074733 |
| cell proliferation | 60 | 1842 | 0.032573 |
| regulation of response to stimulus | 86 | 3171 | 0.027121 |
| cytokine-mediated signaling pathway | 21 | 299 | 0.070234 |
| positive regulation of biological process | 117 | 5011 | 0.023349 | g

FIG. 2 (Continued)

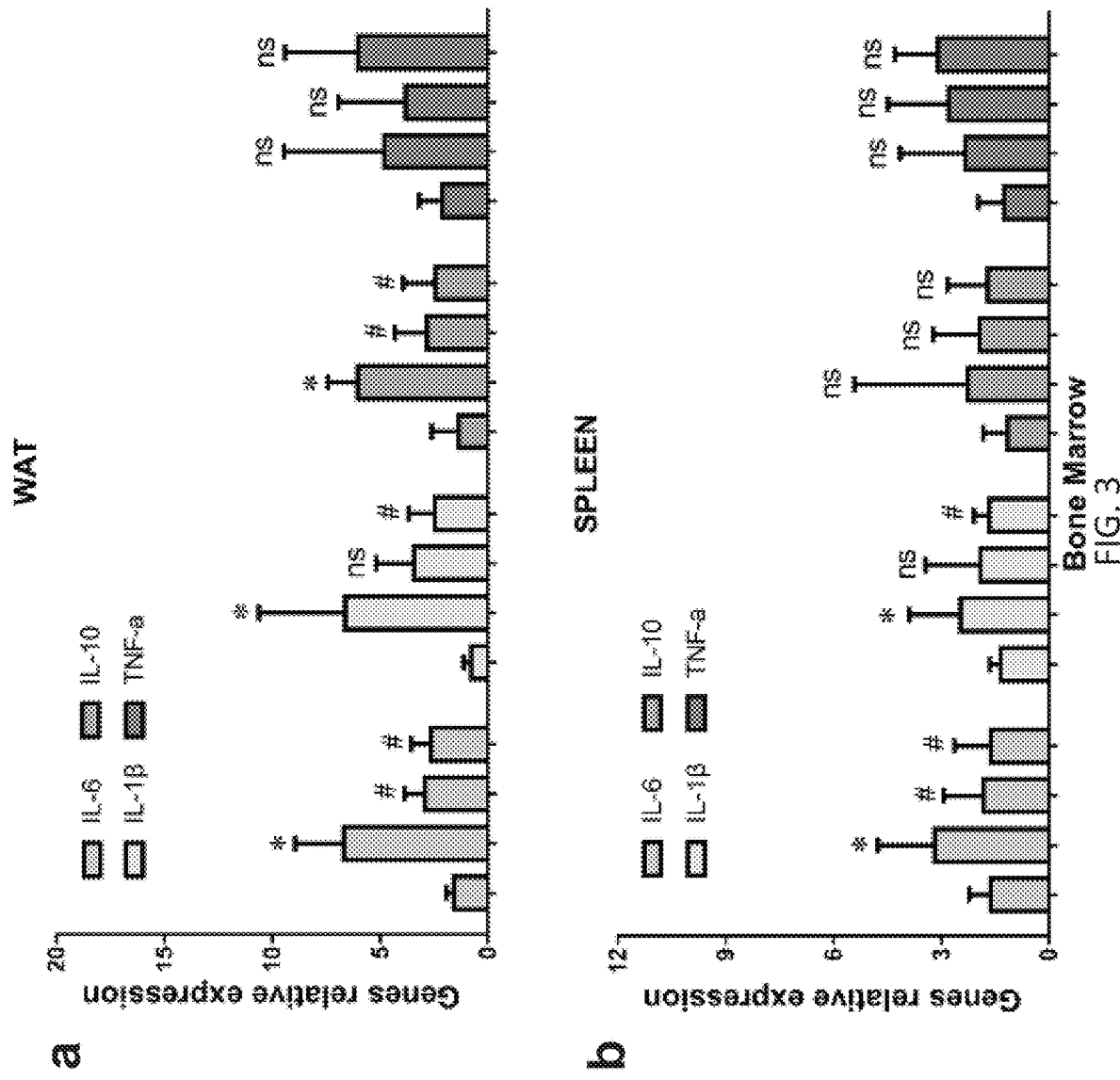

e

NO RANKL

RANKL

AdipoRon 20 μM

AdipoAI 5 μM

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic- qPCR IL-6 F

<400> SEQUENCE: 1
tccagttgcc ttcttgggac                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic- qPCR IL-6 R

<400> SEQUENCE: 2
agtctcctct ccggacttgt                                           20

<210> SEQ ID NO 3
<211> LENGTH: 20
<212> TYPE: DNA
<213> ORGANISM: Artificial Sequence
<220> FEATURE:
<223> OTHER INFORMATION: Synthetic- qPCR IL-1B F

<400> SEQUENCE: 3
gtcaacgtgt gggggatgaa                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic- qPCR IL1B R

<400> SEQUENCE: 4
aagcaatgtg ctggtgcttc                                           20

<210> SEQ ID NO 5

```
<211> LENGTH: 21
<212> TYPE: DNA
<213> ORGANISM: Artificial Sequence
<220> FEATURE:
<223> OTHER INFORMATION: Synthetic- qPCR IL-10 F

<400> SEQUENCE: 5
gctcttactg actggcatga g                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic- qPCR IL-10 R

<400> SEQUENCE: 6
cgcagctcta ggagcatgtg                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic- qPCR TNF-a F

<400> SEQUENCE: 7 tgtcccttc actcactggc                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic- qPCR TNF-a R

<400> SEQUENCE: 8
catcttttgg gggagtgcct                                                20

<210> SEQ ID NO 9
<211> LENGTH: 19
<212> TYPE: DNA
<213> ORGANISM: Artificial Sequence
<220> FEATURE:
<223> OTHER INFORMATION: Synthetic- qPCR AdipoR1 F

<400> SEQUENCE: 9 tcttttggg tgcagtgct                                                  19

<210> SEQ ID NO 10
<211> LENGTH: 22
<212> TYPE: DNA
<213> ORGANISM: Artificial Sequence
<220> FEATURE:
<223> OTHER INFORMATION: Synthetic- qPCR AdipoR1 R

<400> SEQUENCE: 10
gcaattcctg aatagtccag tt                                             22

<210> SEQ ID NO 11
<211> LENGTH: 18
<212> TYPE: DNA
<213> ORGANISM: Artificial Sequence
<220> FEATURE:
<223> OTHER INFORMATION: Synthetic- qPCR AdipoR2 F

<400> SEQUENCE: 11
```

```
gggcattgca gccattat                                                   18

<210> SEQ ID NO 12
<211> LENGTH: 20
<212> TYPE: DNA
<213> ORGANISM: Artificial Sequence
<220> FEATURE:
<223> OTHER INFORMATION: Synthetic- qPCR AdipoR2 R

<400> SEQUENCE: 12
taggcccaaa aacactcctg                                                 20

<210> SEQ ID NO 13
<211> LENGTH: 23
<212> TYPE: DNA
<213> ORGANISM: Artificial Sequence
<220> FEATURE:
<223> OTHER INFORMATION: Synthetic- qPCR APPL1 F

<400> SEQUENCE: 13
gctttgttag aacctctact ggg                                             23

<210> SEQ ID NO 14
<211> LENGTH: 23
<212> TYPE: DNA
<213> ORGANISM: Artificial Sequence
<220> FEATURE:
<223> OTHER INFORMATION: Synthetic- qPCR APPL1 R

<400> SEQUENCE: 14
ggtcaggcag atataaaggg tca                                             23

<210> SEQ ID NO 15
<211> LENGTH: 22
<212> TYPE: DNA
<213> ORGANISM: Artificial Sequence
<220> FEATURE:
<223> OTHER INFORMATION: Synthetic- qPCR APPL2 F

<400> SEQUENCE: 15
caccctcaca gattacacca ac                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic- qPCR APPL2 R

<400> SEQUENCE: 16
ggagaaccat agtgtctgcc ag                                              22

<210> SEQ ID NO 17
<211> LENGTH: 21
<212> TYPE: DNA
<213> ORGANISM: Artificial Sequence
<220> FEATURE:
<223> OTHER INFORMATION: Synthetic- qPCR MyD88 F

<400> SEQUENCE: 17
aggacaaacg ccggaacttt t                                               21

<210> SEQ ID NO 18
<211> LENGTH: 23
<212> TYPE: DNA
```

```
<213> ORGANISM: Artificial Sequence
<220> FEATURE:
<223> OTHER INFORMATION: Synthetic- qPCR MyD88 R

<400> SEQUENCE: 18
gccgatagtc tgtctgttct agt                                           23

<210> SEQ ID NO 19
<211> LENGTH: 19
<212> TYPE: DNA
<213> ORGANISM: Artificial Sequence
<220> FEATURE:
<223> OTHER INFORMATION: Synthetic- qPCR c-Maf F

<400> SEQUENCE: 19
ggagaccgac cgcatcatc                                                19

<210> SEQ ID NO 20
<211> LENGTH: 23
<212> TYPE: DNA
<213> ORGANISM: Artificial Sequence
<220> FEATURE:
<223> OTHER INFORMATION: Synthetic- qPCR c-Maf R

<400> SEQUENCE: 20
tcatccagta gtagtcttcc agg                                           23

<210> SEQ ID NO 21
<211> LENGTH: 21
<212> TYPE: DNA
<213> ORGANISM: Artificial Sequence
<220> FEATURE:
<223> OTHER INFORMATION: Synthetic- qPCR GAPDH F

<400> SEQUENCE: 21
aggtcggtgt gaacggattt g                                             21

<210> SEQ ID NO 22
<211> LENGTH: 23
<212> TYPE: DNA
<213> ORGANISM: Artificial Sequence
<220> FEATURE:
<223> OTHER INFORMATION: Synthetic- qPCR GAPDH R

<400> SEQUENCE: 22
tgtagaccat gtagttgagg tca                                           23

<210> SEQ ID NO 23
<211> LENGTH: 20
<212> TYPE: DNA
<213> ORGANISM: Artificial Sequence
<220> FEATURE:
<223> OTHER INFORMATION: Synthetic- qPCR B-actin F

<400> SEQUENCE: 23
agagggaaat cgtgcgtgac                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic- qPCR B-actin R

<400> SEQUENCE: 24
caatagtgat gacctggcgt                                               20
```

```
<210> SEQ ID NO 25
<211> LENGTH: 19
<212> TYPE: RNA
<213> ORGANISM: Artificial Sequence
<220> FEATURE:
<223> OTHER INFORMATION: Synthetic- siRNA AdipoR1

<400> SEQUENCE: 25
gacuuggcuu gaguggugu                                                  19

<210> SEQ ID NO 26
<211> LENGTH: 19
<212> TYPE: RNA
<213> ORGANISM: Artificial Sequence
<220> FEATURE:
<223> OTHER INFORMATION: Synthetic- siRNA AdipoR1

<400> SEQUENCE: 26
acaccacuca agccaaguc                                                  19

<210> SEQ ID NO 27
<211> LENGTH: 19
<212> TYPE: RNA
<213> ORGANISM: Artificial Sequence
<220> FEATURE:
<223> OTHER INFORMATION: Synthetic- siRNA AdipoR2

<400> SEQUENCE: 27
agagugaagc caccugguu                                                  19

<210> SEQ ID NO 28
<211> LENGTH: 19
<212> TYPE: RNA
<213> ORGANISM: Artificial Sequence
<220> FEATURE:
<223> OTHER INFORMATION: Synthetic- siRNA AdipoR2

<400> SEQUENCE: 28
aaccaggugg cuucacucu                                                  19

<210> SEQ ID NO 29
<211> LENGTH: 21
<212> TYPE: DNA
<213> ORGANISM: Artificial Sequence
<220> FEATURE:
<223> OTHER INFORMATION: Synthetic- siRNA APPL1

<400> SEQUENCE: 29
ggucuuuacu ugguguauut t                                               21

<210> SEQ ID NO 30
<211> LENGTH: 21
<212> TYPE: DNA
<213> ORGANISM: Artificial Sequence
<220> FEATURE:
<223> OTHER INFORMATION: Synthetic- siRNA APPL1

<400> SEQUENCE: 30
aauacaccaa guaaagacct t                                               21

<210> SEQ ID NO 31
<211> LENGTH: 21
<212> TYPE: DNA
<213> ORGANISM: Artificial Sequence
<220> FEATURE:
```

<223> OTHER INFORMATION: Synthetic- siRNA APPL2

<400> SEQUENCE: 31
gcacuuugaa ggaucucuut t                                             21

<210> SEQ ID NO 32
<211> LENGTH: 21
<212> TYPE: DNA
<213> ORGANISM: Artificial Sequence
<220> FEATURE:
<223> OTHER INFORMATION: Synthetic- siRNA APPL2

<400> SEQUENCE: 32
aagagauccu ucaaagugct g                                             21

<210> SEQ ID NO 33
<211> LENGTH: 21
<212> TYPE: DNA
<213> ORGANISM: Artificial Sequence
<220> FEATURE:
<223> OTHER INFORMATION: Synthetic- siRNA MyD88

<400> SEQUENCE: 33
cuauaugcga cuauaccaat t                                             21

<210> SEQ ID NO 34
<211> LENGTH: 21
<212> TYPE: DNA
<213> ORGANISM: Artificial Sequence
<220> FEATURE:
<223> OTHER INFORMATION: Synthetic- siRNA MyD88

<400> SEQUENCE: 34
uugguauagu cgcauauagt g                                             21

<210> SEQ ID NO 35
<211> LENGTH: 21
<212> TYPE: DNA
<213> ORGANISM: Artificial Sequence
<220> FEATURE:
<223> OTHER INFORMATION: Synthetic- siRNA c-Maf

<400> SEQUENCE: 35
guuaaugacu ucgaucugat t                                             21

<210> SEQ ID NO 36
<211> LENGTH: 21
<212> TYPE: DNA
<213> ORGANISM: Artificial Sequence
<220> FEATURE:
<223> OTHER INFORMATION: Synthetic- siRNA c-Maf

<400> SEQUENCE: 36
ucagaucgaa gucauuaaca t                                             21

<210> SEQ ID NO 37
<211> LENGTH: 19
<212> TYPE: DNA
<213> ORGANISM: Artificial Sequence
<220> FEATURE:
<223> OTHER INFORMATION: Synthetic- LC3 F

<400> SEQUENCE: 37
gaccgctgta aggaggtgc                                                19

```
<210> SEQ ID NO 38
<211> LENGTH: 22
<212> TYPE: DNA
<213> ORGANISM: Artificial Sequence
<220> FEATURE:
<223> OTHER INFORMATION: Synthetic- LC3 R

<400> SEQUENCE: 38
cttgaccaac tcgctcatgt ta                                              22

<210> SEQ ID NO 39
<211> LENGTH: 20
<212> TYPE: DNA
<213> ORGANISM: Artificial Sequence
<220> FEATURE:
<223> OTHER INFORMATION: Synthetic- IL-6 F

<400> SEQUENCE: 39
ccaagaggtg agtgcttccc                                                 20

<210> SEQ ID NO 40
<211> LENGTH: 22
<212> TYPE: DNA
<213> ORGANISM: Artificial Sequence
<220> FEATURE:
<223> OTHER INFORMATION: Synthetic- IL-6 R

<400> SEQUENCE: 40
ctgttgttca gactctctcc ct                                              22

<210> SEQ ID NO 41
<211> LENGTH: 23
<212> TYPE: DNA
<213> ORGANISM: Artificial Sequence
<220> FEATURE:
<223> OTHER INFORMATION: Synthetic- CCL2 F

<400> SEQUENCE: 41
ttaaaaacct ggatcggaac caa                                             23

<210> SEQ ID NO 42
<211> LENGTH: 23
<212> TYPE: DNA
<213> ORGANISM: Artificial Sequence
<220> FEATURE:
<223> OTHER INFORMATION: Synthetic- CCL2 R

<400> SEQUENCE: 42
gcattagctt cagatttacg ggt                                             23

<210> SEQ ID NO 43
<211> LENGTH: 20
<212> TYPE: DNA
<213> ORGANISM: Artificial Sequence
<220> FEATURE:
<223> OTHER INFORMATION: Synthetic- B-actin F

<400> SEQUENCE: 43
ggctgtattc ccctccatcg                                                 20

<210> SEQ ID NO 44
<211> LENGTH: 22
<212> TYPE: DNA
<213> ORGANISM: Artificial Sequence
<220> FEATURE:
<223> OTHER INFORMATION: Synthetic- B-actin R
```

```
<400> SEQUENCE: 44
ccagttggta acaatgccat gt                                          22

<210> SEQ ID NO 45
<211> LENGTH: 21
<212> TYPE: DNA
<213> ORGANISM: Artificial Sequence
<220> FEATURE:
<223> OTHER INFORMATION: Synthetic- TRAP F

<400> SEQUENCE: 45
cactcccacc ctgagatttg t                                           21

<210> SEQ ID NO 46
<211> LENGTH: 19
<212> TYPE: DNA
<213> ORGANISM: Artificial Sequence
<220> FEATURE:
<223> OTHER INFORMATION: Synthetic- TRAP R

<400> SEQUENCE: 46
catcgtctgc acggttctg                                              19

<210> SEQ ID NO 47
<211> LENGTH: 22
<212> TYPE: DNA
<213> ORGANISM: Artificial Sequence
<220> FEATURE:
<223> OTHER INFORMATION: Synthetic- Cathepsin K F

<400> SEQUENCE: 47
gaagaagact caccagaagc ag                                          22

<210> SEQ ID NO 48
<211> LENGTH: 21
<212> TYPE: DNA
<213> ORGANISM: Artificial Sequence
<220> FEATURE:
<223> OTHER INFORMATION: Synthetic- Cathepsin K R

<400> SEQUENCE: 48
tccaggttat gggcagagat t                                           21
```

USING ADIPONECTIN RECEPTOR AGONISTS TO TREAT INFLAMMATION AND BONE DISEASES IN DIABETES

CROSS-REFERENCE TO RELATED APPLICATIONS

The present application claims benefit of priority to U.S. Patent Application Ser. No. 63/125,362, filed Dec. 14, 2020, the contents of which is incorporated by reference in its entirety.

STATEMENT REGARDING FEDERALLY SPONSORED RESEARCH

This invention was made with government support under DE-26507 awarded by National Institutes of Health. The government has certain rights in the invention.

REFERENCE TO A SEQUENCE LISTING

This application is being filed electronically via EFS-Web and includes an electronically submitted Sequence Listing in .txt format. The .txt file contains a sequence listing entitled "166118_01126_ST25.txt" created on Dec. 14, 2021 and is 9,729 bytes in size. The Sequence Listing contained in this .txt file is part of the specification and is hereby incorporated by reference herein in its entirety.

BACKGROUND OF THE INVENTION

Adiponectin (APN) is an adipokine secreted from adipocytes that binds to adiponectin receptors AdipoR1 and AdipoR2 and exerts an anti-inflammatory response through mechanisms not fully understood. Despite the therapeutic promise of APN, its clinical use has significant disadvantages, including the high probability of adverse immunoreactions, the requirement of high dosage and constant intravenous (i.v.) injection to elicit beneficial effects, and the challenges associated with producing APN protein on a large scale.

AdipoRon is an adiponectin receptor agonist that has been shown to reduce insulin resistance, glucose intolerance, and it prolongs the shortened life span of diabetic mice. AdipoRon attenuates diabetes-related periodontal bone loss in the diet-induced obesity (DIO) mouse model by inhibiting osteoclastogenesis. AdipoRon has also been suggested as alleviating the calcification of osteoarthritis chondrocytes by enhancing autophagy. However, AdipoRon has clinical limitations due to its week binding affinity for AdipoRs and a relatively high $K_m$, which have delayed its development and clinical application. As a result, there is a need to develop small molecules that activate AdipoR1 and AdipoR2 to be used to inhibit the inflammatory response in endotoxemia and other inflammatory disorders or bone loss in periodontitis and other bone disorders.

BRIEF SUMMARY OF THE INVENTION

Disclosed herein are AdipoR agonists and methods of making and using the same. One aspect of the invention provides for a compound of Formula I

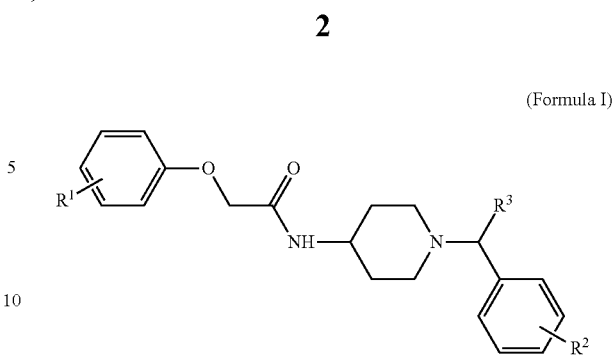
(Formula I)

or a pharmaceutically acceptable salt thereof where $R^1$ is $-C(=O)R^4$ where $R^4$ is a halo-substituted phenyl, an unsubstituted phenyl, or a $C_1$-$C_4$ alkyl or $R^1$ is an unsubstituted phenyl; $R^2$ is a $C_1$-$C_4$ alkoxyl, hydrogen, or halo; and $R^3$ is hydrogen of a $C_1$-$C_4$ alkyl. In some embodiments, if $R^1$ is $-C(=O)R^4$ and $R^4$ is a 4-chloro substituted phenyl, $R^2$ and $R^3$ are not both hydrogen; if $R^1$ is $-C(=O)R^4$ and $R^4$ is the unsubstituted phenyl, (i) $R^2$ and $R^3$ are not both hydrogen or (ii) $R^2$ and $R^3$ are not respectively 4-chloro and hydrogen; if $R^1$ is $-C(=O)R^4$ and $R^4$ is methyl, $R^2$ is not 3,4-difluoro, 3,4-dichloro, or 4-bromo and R3 is not hydrogen; if $R^1$ is $-C(=O)R^4$ and $R^4$ is ethyl, $R^2$ and $R^3$ are not respectively 3,4-dichloro and hydrogen; and/or if $R^1$ is phenyl, $R^2$ and $R^3$ are not respectively hydrogen and methyl. In some embodiments, the compound is one or more of Compound 1

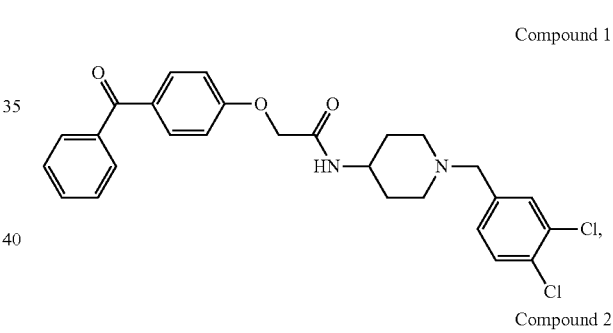

Compound 2

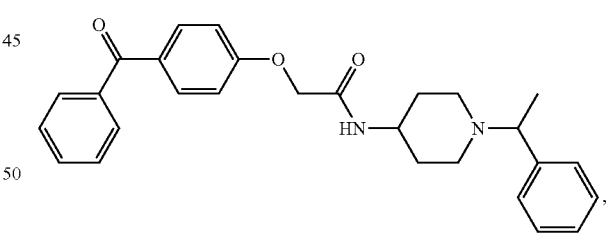

Compound 3

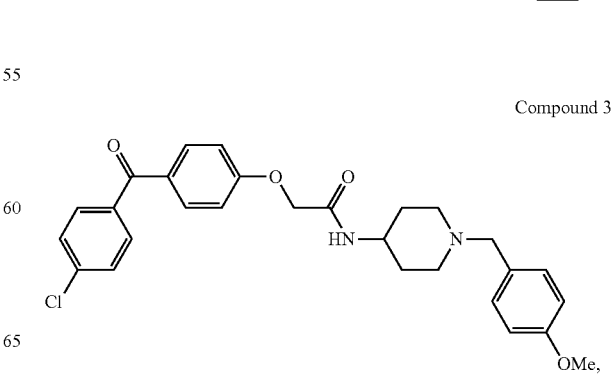

Compound 4

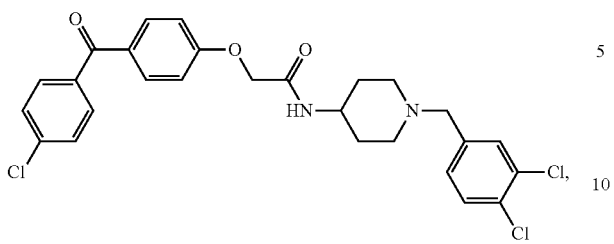

Compound 5

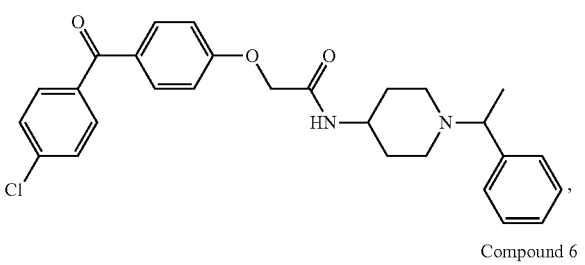

Compound 6

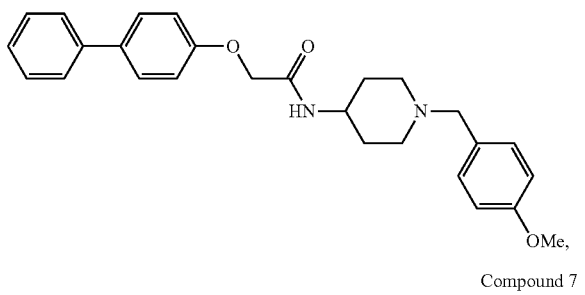

Compound 7

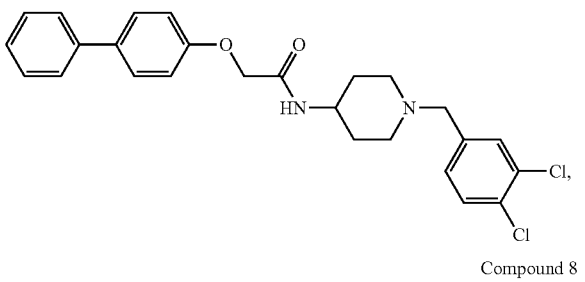

Compound 8

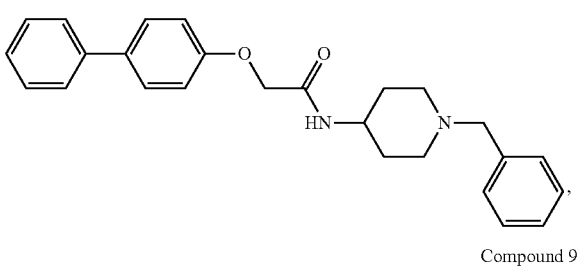

Compound 9

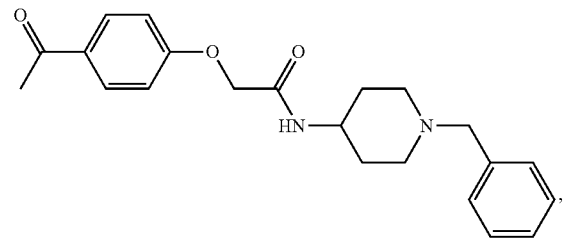

Compound 10

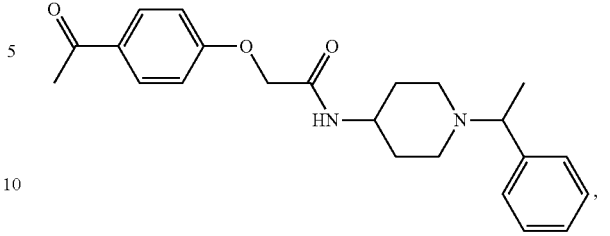

or a pharmaceutically acceptable salt thereof. In a particular embodiment, the compound is Compound 3.

Another aspect of the invention provides for a method for the treatment of inflammation in a subject. The method may comprise administering an effective amount of any of the compounds described herein.

Another aspect of the invention provides for a method for the treatment of bone loss a subject. The method may comprise administering an effective amount of any of the compounds described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
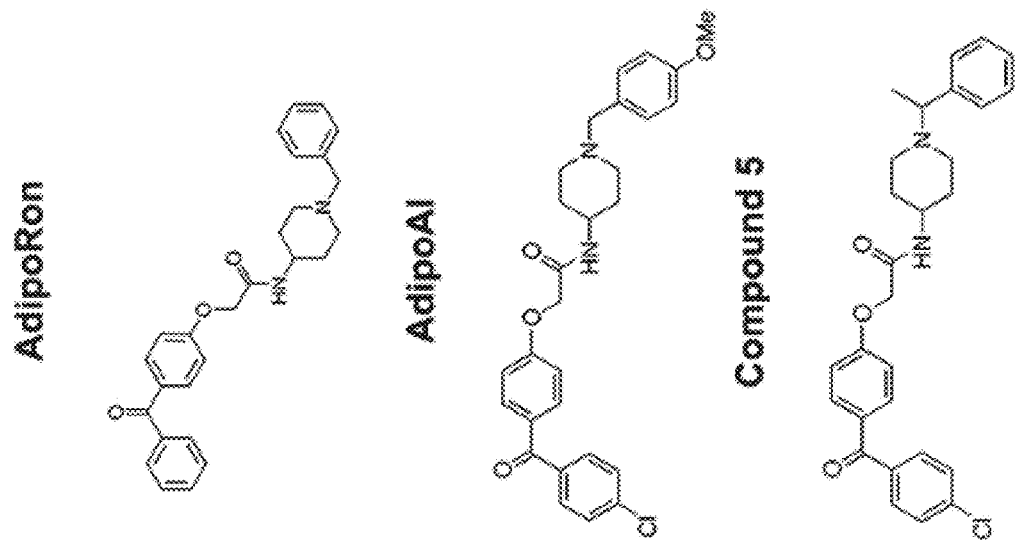
FIG. 1 Characterization of anti-inflammatory properties of APR-like compounds. (a) Raw264.7 cells were pretreated with APR (20 μM) or new compounds 1 to 10 (5 μM) for 24 h followed by incubation with LPS (100 ng/mL) for an additional 6 h. IL-6 and IL-10 mRNA expression levels were evaluated by qPCR and normalized with GAPDH mRNA level. (b) Raw264.7 cells were pretreated with different doses of AdipoAI for 24 h followed by incubation with LPS (100 ng/mL) for additional 6 h to evaluate dose-dependency of AdipoAI in inhibiting IL-6 and IL-1β mRNA expression levels by qRT-PCR and normalized with GAPDH mRNA level. (c) Evaluation of cytotoxicity of APR, AdipoAI and compound 5 by CCK8 assay in Raw264.7 cells treated for 24 hours. (d) BMMs were pretreated with APR (20 μM), AdipoAI (5 μM) or compound 5 (5 μM) for 24 h followed by incubation with LPS (100 ng/mL) for additional 6 h for the measurement of IL-6 and IL-1β mRNA expression levels by qRT-PCR and normalized with GAPDH mRNA level. Data were expressed as the mean±SEM at five biological independent experiments. One-way ANOVA test for multiple-group comparisons, *P<0.05, significant differences between each indicated group.
Figure 1:
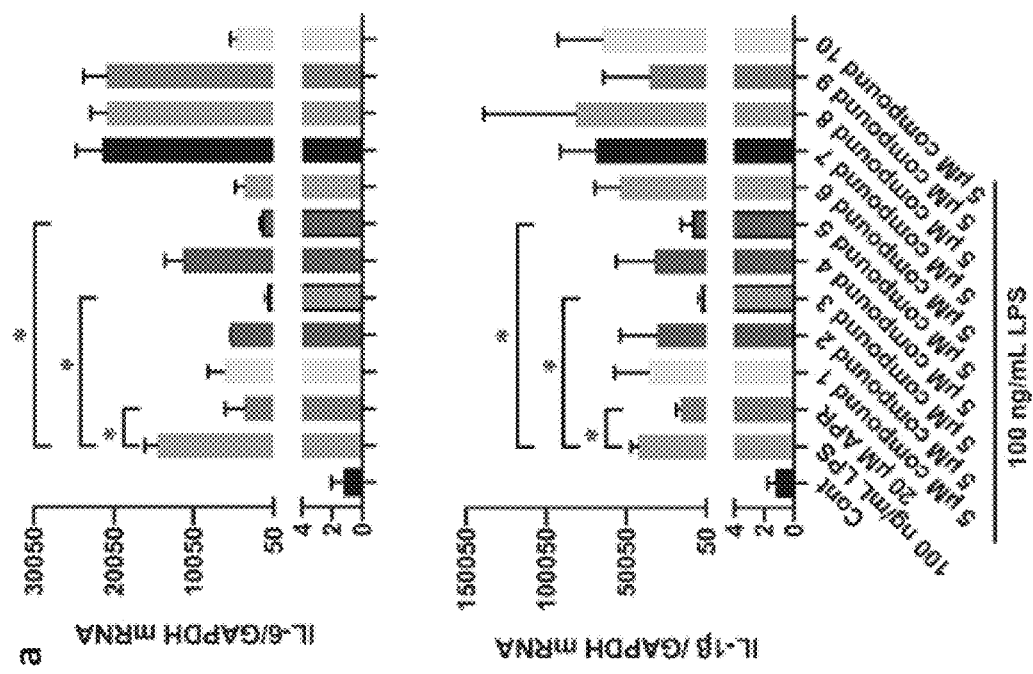
Figure 1:
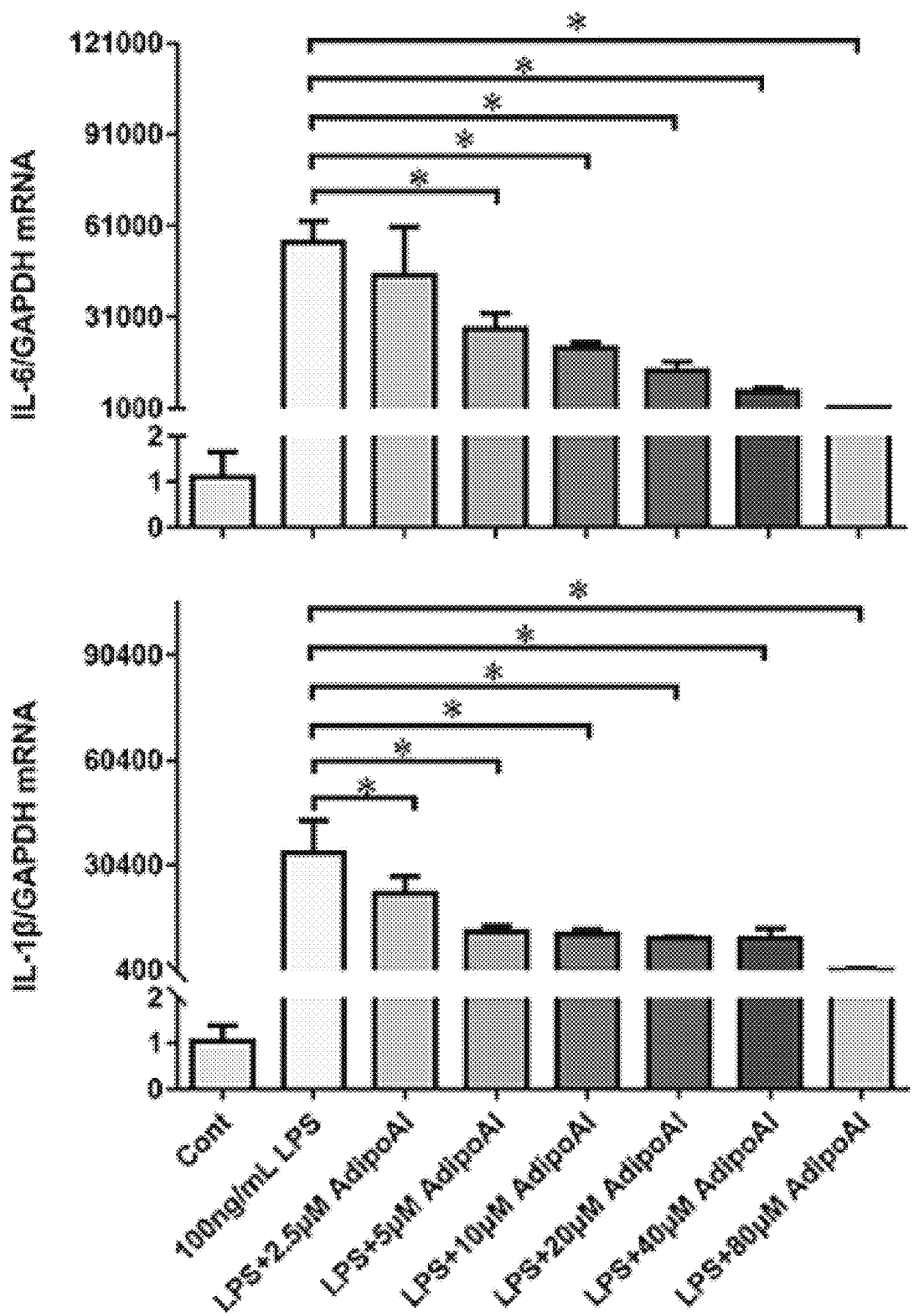
Figure 1:
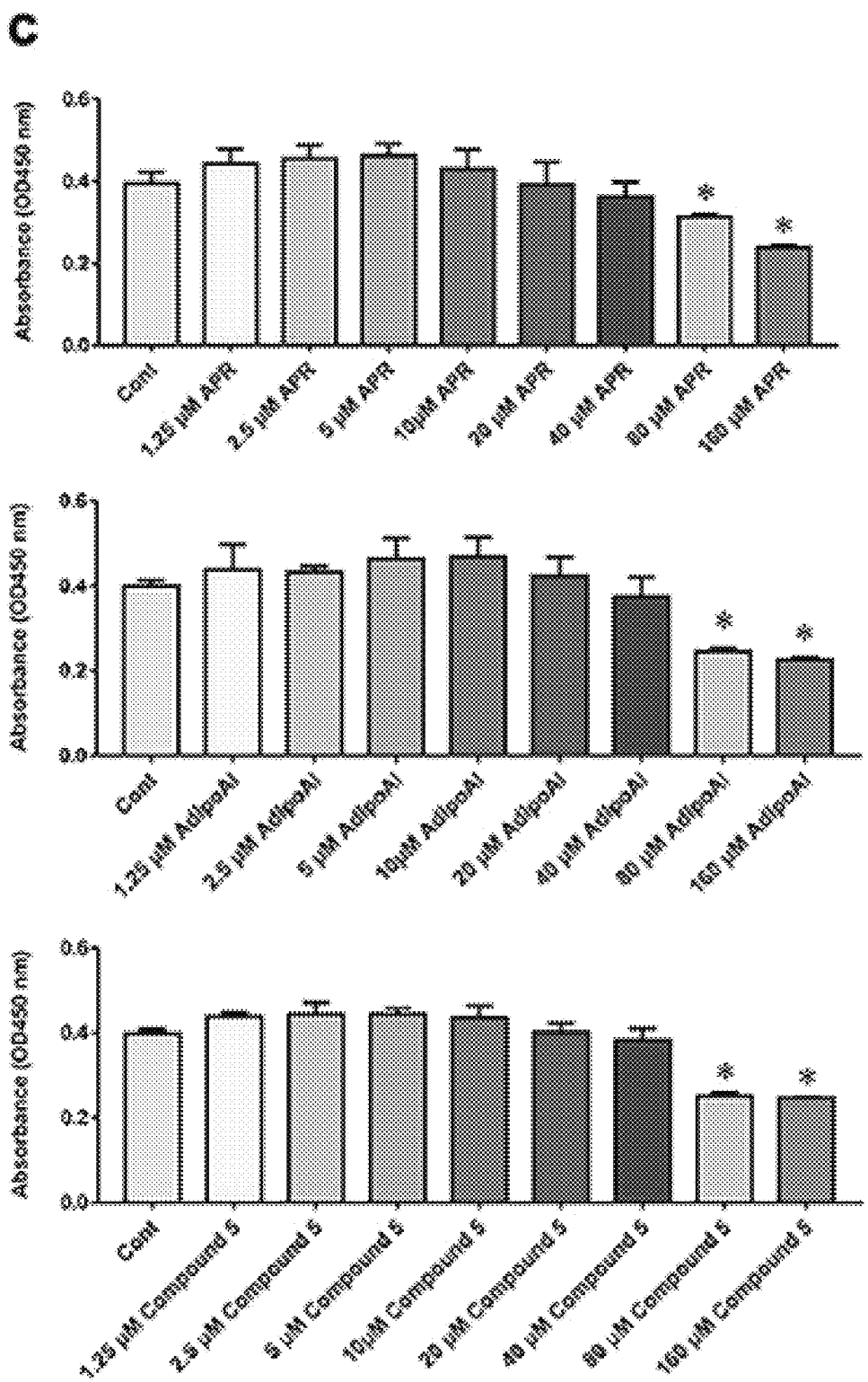
Figure 1:
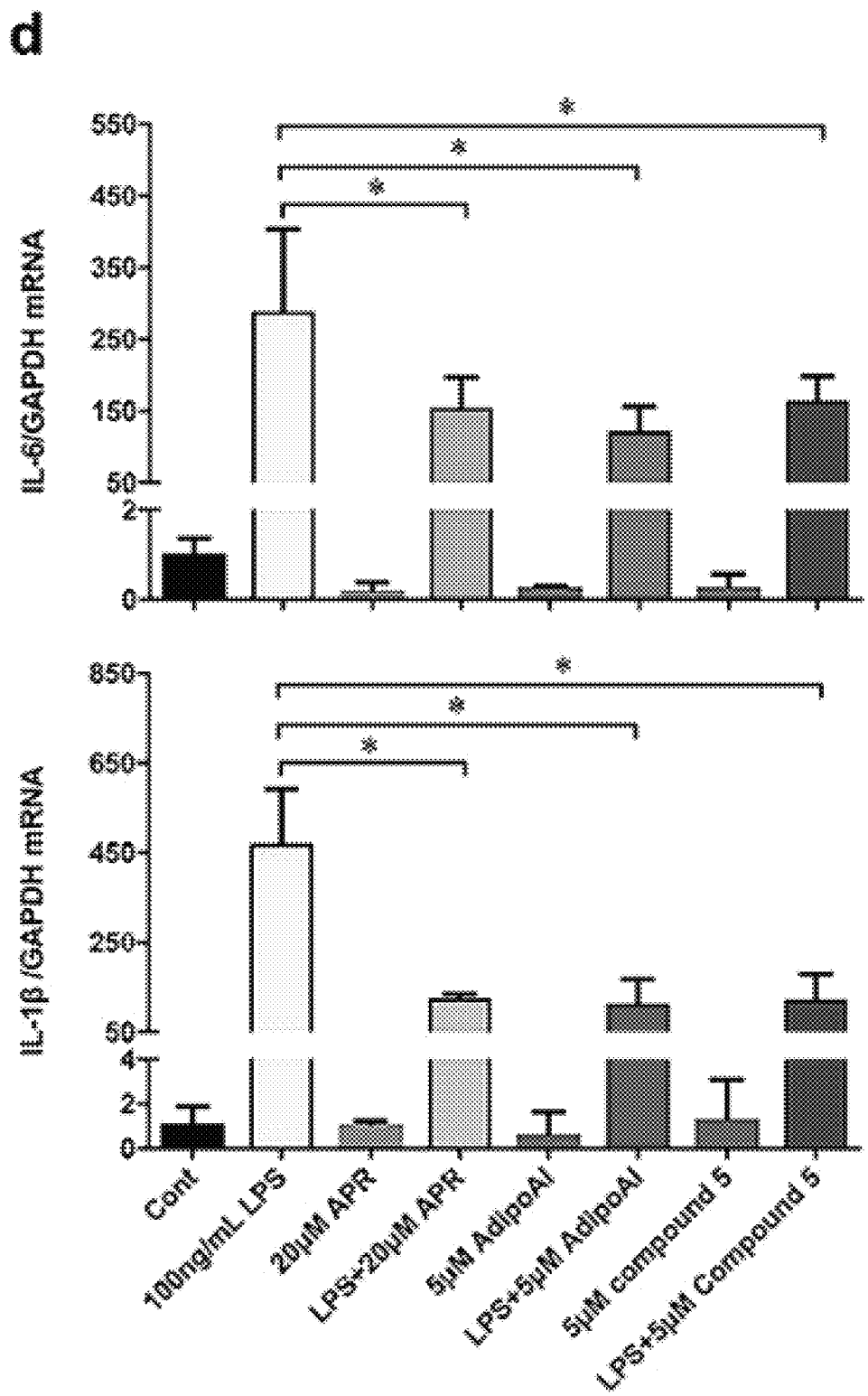

Disclosed herein are AdipoR agonists, such as AdipoAI, and methods of making and using the same. AdipoR agonists are compounds that bind and activate adipopectin receptor 1 (AdipoR1) and receptor 2 (AdipoR2) that can show the biological effects of adiponectin (APN). AdipoR agonists, such as AdipoAI, decrease fasting blood glucose, improves diabetes, inhibits osteoclastic resorption, promotes bone formation, and controls local and systemic inflammation. Therefore, AdipoR agonists, such as AdipoAI, have clinical applications in treating inflammatory and bone diseases in diabetics through oral administration as it can be systemically or locally delivered.

AdipoR Agonists

One aspect of the invention provides for AdipoR agonists of Formula I

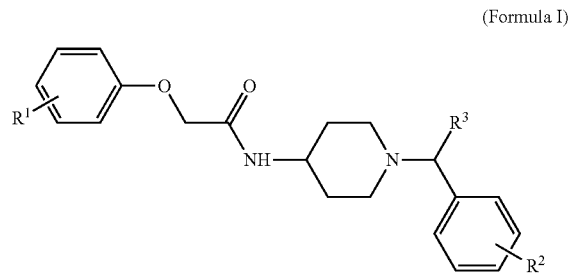

(Formula I)

or a pharmaceutically acceptable salt thereof where $R^1$ is —C(=O)$R^4$ where $R^4$ is a halo-substituted phenyl, an unsubstituted phenyl, or a $C_1$-$C_4$ alkyl or $R^1$ is an unsubstituted phenyl; $R^2$ is a $C_1$-$C_4$ alkoxyl, hydrogen, or halo; and $R^3$ is hydrogen of a $C_1$-$C_4$ alkyl.

In some embodiments, $R^1$ is —C(=O)$R^4$ and $R^4$ is the halo substituted phenyl. When $R^1$ is —C(=O)$R^4$ and $R^4$ is a halo substituted phenyl, the phenyl may be substituted with one or more halogen atoms, including chlorine, fluorine, bromine, or combinations thereof. The halo substitution may occur at any suitable phenyl position, including 2, 3, 4, 5, and/or 6 where 1 is the point of attachment to the phenyl to the carbonyl. In some embodiments, the halo substitution occurs at position 4, i.e., a 4-halo substitution. Suitably the AdipoR agonist may comprise a 4-chloro substituted phenyl. In some embodiments where $R^4$ is a 4-chloro substituted phenyl, $R^2$ and $R^3$ are not both hydrogen.

In some embodiments, $R^1$ is —C(=O)$R^4$ and $R^4$ is an unsubstituted phenyl. In some embodiments where $R^4$ is an unsubstituted phenyl, $R^2$ and $R^3$ are not both hydrogen or $R^2$ and $R^3$ are not respectively 4-chloro and hydrogen.

In some embodiments, $R^1$ is —C(=O)$R^4$ and $R^4$ is a $C_1$-$C_4$ alkyl, such as methyl, ethyl, propyl, isopropyl, butyl, 1-methylpropyl, or 2-methylpropyl. In some embodiments, $R^4$ is methyl. In some embodiments where the $R^4$ is methyl, $R^2$ is not 3,4-difluoro, 3,4-dichloro, or 4-bromo and $R^3$ is not hydrogen. In some embodiments, $R^4$ is ethyl. In some embodiments where $R^4$ is ethyl, $R^2$ and $R^3$ are not respectively 3,4-dichloro and hydrogen.

In some embodiments, $R^2$ is selected from phenyl. In some embodiments where $R^1$ is phenyl, $R^2$ and $R^3$ are not respectively hydrogen and methyl.

In some embodiments, $R^2$ is hydrogen.

In some embodiments, $R^2$ comprises one or more $C_1$-$C_4$ alkoxyl substituents, such as —O— methyl, —O-ethyl, —O-propyl, —O-isopropyl, —O-butyl, —O-1-methylpropyl, or —O-2-methylpropyl. The $C_1$-$C_4$ alkoxyl substitution may occur at any suitable phenyl position, including 2, 3, 4, 5, and/or 6 where 1 is the point of attachment of the phenyl to the methylene of Formula I. In some embodiments, the $C_1$-$C_4$ substitution occurs at position 4, i.e., a 4-alkyoxyl substitution. In some embodiments, the AdipoR against comprises a 4-O-methyl substitution.

In some embodiments, $R^2$ comprises one or more halo substituents, such as chlorine, fluorine, bromine, or combinations thereof. The $C_1$-$C_4$ alkoxyl substitution may occur at any suitable phenyl position, including 2, 3, 4, 5, and/or 6 where 1 is the point of attachment of the phenyl to the methylene of Formula I. In some embodiments, the halo substitution occurs at position 3, position 4 or both positions 3 and 4, i.e., a 3-halo, 4-halo, or 3,4-dihalo substitution. In some embodiments, the AdipoR against comprises a 3,4-dichloro substitution.

In some embodiments, $R^3$ is hydrogen.

In some embodiments, $R^3$ comprises a $C_1$-$C_4$ alkyl, such as methyl, ethyl, propyl, isopropyl, butyl, 1-methylpropyl, or 2-methylpropyl. In some embodiments, $R^3$ is methyl.

Exemplary AdipoR agonists, include without limitation, one or more of

Compound 1

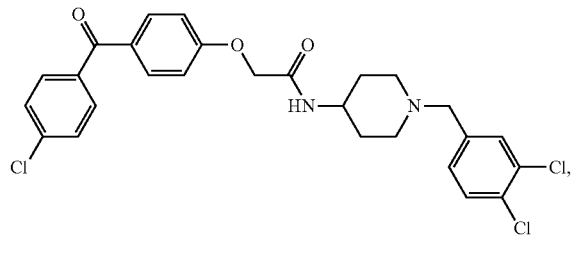

Compound 2

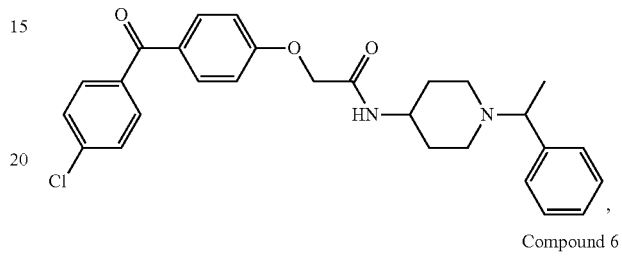

Compound 3

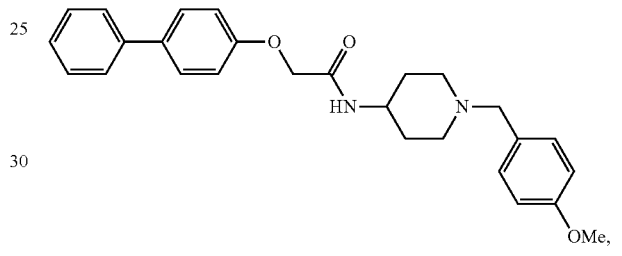

Compound 4

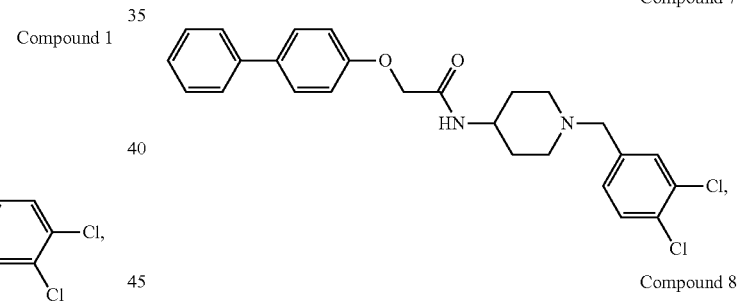

Compound 5

Compound 6

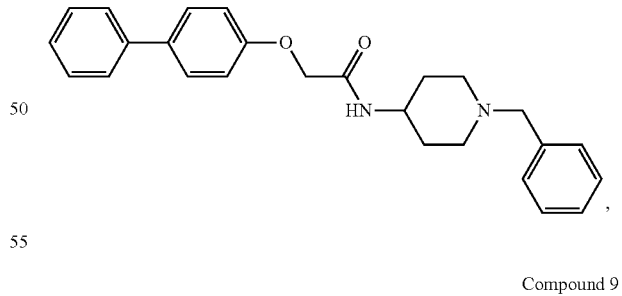

Compound 7

Compound 8

Compound 9

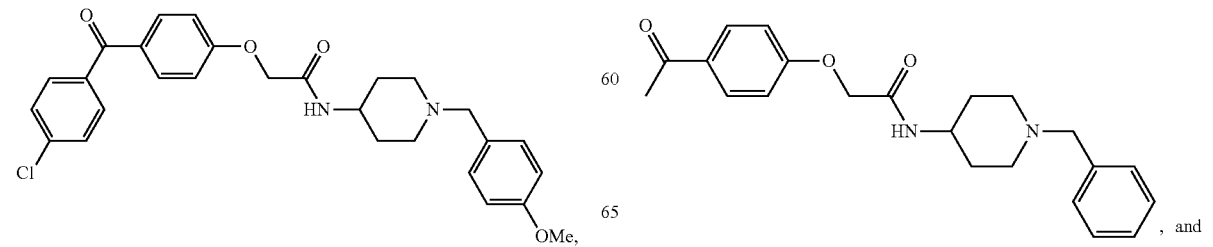

, and

-continued

Compound 10

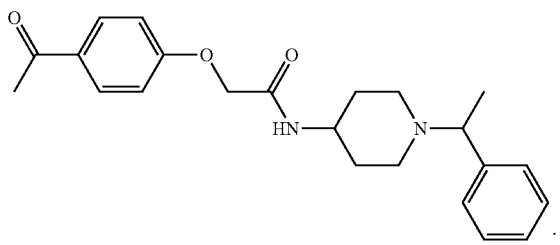

An exemplary method for making the compounds described herein is provided in the Examples below.

In some embodiments, the AdipoR agonists used in the methods described herein may comprise AdipoR agonists such as those described in US 2016/0214967. In other embodiments, the AdipoR agonists described in US 2016/0214967 are specifically excluded.

Pharmaceutical Compositions

The AdipoR agonists described herein may be formulated as pharmaceutical compositions that include: (a) a therapeutically effective amount of one or more compounds as described herein and (b) one or more pharmaceutically acceptable carriers, excipients, or diluents. The pharmaceutical composition may include the compound in a range of about 0.1 to 5000 mg (preferably about 0.5 to 500 mg, and more preferably about 1 to 100 mg). The pharmaceutical composition may be administered to provide the compound at a daily dose of about 0.1 to 500 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration). In some embodiments, the pharmaceutical composition may further comprise a bioactive agent.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended-release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers, such as microcrystalline cellulose, lactose, dibasic calcium phosphate, saccharides, and mixtures of any of the foregoing.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders, and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating, compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route, intraperitoneal injection, and topically, such as via eye drop. Such formulations may be prepared by any method known in the art of pharmacy, for example by bringing into association the active ingredient with the carrier(s) or excipient(s).

The formulations may be presented in unit-dose or multi-dose containers.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the compound chosen for the therapy and other factors, such as the indication for which it is given. The pharmaceutical compositions disclosed herein may be formulated to provide quick, sustained, or delayed release of the active ingredient after administration to the patient by employing well known procedures. The compounds for use according to the methods of disclosed herein may be administered as a single compound or a combination of compounds. For example, a compound may be administered as a single compound or in combination with another compound that has the same or different pharmacological activity.

As indicated above, pharmaceutically acceptable salts of the compounds are contemplated and may be utilized in the disclosed methods. The term "pharmaceutically acceptable salt" as used herein, refers to salts of the compounds that are substantially non-toxic to living organisms.

Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Methods of Treatment

Another aspect of the technology provides for a method for treating of subject in need of an AdipoR agonist. Suitably, method may comprise administering an effective amount of the compound to the subject. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the compounds disclosed herein alone or in combination with another bioactive agent.

As used herein the term "effective amount" refers to the amount or dose of the compound, such as upon single or multiple dose administration to the subject, which provides the desired effect. An effective amount can be determined by the attending diagnostician, as one skilled in the art, using known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

Methods for the Treatment of Inflammation

In some embodiments, the subject is in need of a treatment for inflammation. Inflammation refers the release of pro-inflammatory cytokines from immune-related cells and the activation of the innate immune systems. The tissue inflammatory response caused by bacteria, trauma, toxins, heat, or other factors, can potentially activate the innate immune responses. Innate immune responses are capable of not only combating infectious microbes but also contributing to pathological situations, such as sepsis, obesity, atherosclerosis, autoimmunity, and cancer. Lipopolysaccharide (LPS) is a natural adjuvant synthesized by Gram-negative bacteria that stimulates cells through Toll-like receptor 4 (TLR4) and has profound effects on inflammation and immune responses. Also, TLR4-triggered signaling depends on the adaptor proteins MyD88 and Toll—interleukin-1 (IL-1) receptor (TIR) domain-containing adaptor-inducing IFNβ (TRIF), which mediate MyD88-dependent and TRIF-dependent signaling pathways.

In MyD88-dependent signaling pathways, the recruitment and phosphorylation of IL-1 receptor-associated kinase 1 (IRAK1) and IRAK4 is triggered by MyD88 binding to TLR4, which further facilitates oligomerization and auto-ubiquitination of TNF receptor-associated factor 6 (TRAF6). Ubiquitinated TRAF6 subsequently engages other signaling proteins, such as transforming growth factor β-activated kinase (TAK1), to activate the inhibitor of κB (IκB) kinase (IKK) and MAPK kinase (MKK), which induce immune and inflammatory responses via transcription factors such as NF-κB and activator protein 1 (AP-1).

As the most abundant adipokine, adiponectin (APN) exerts various biological functions, including insulin sensitization, fatty acid oxidation, and glucose uptake, and plays a role in maintaining tissue homeostasis. APN inhibits TNF-α-stimulated IL-8 synthesis in endothelial cells by modulating NF-κB signaling, and normalizes cytokine production in LPS-primed Kupffer cells and macrophages by suppressing ERK and p38 MAPK signaling. Furthermore, APN increases the expression of anti-inflammatory genes, such as heme oxygenase-1 (HO-1) and the genes of autophagy.

AdipoR1 and AdipoR2 serve as the main receptors for APN in vivo. Both contain seven transmembrane domains, but the structure and function are distinct from G-protein coupled receptors. Adaptors APPL1 and APPL2 (adaptor protein containing pleckstrin homology domain, phosphotyrosine binding (PTB) domain, and leucine zipper motif), bind to APN receptors and mediate APN signaling and function in mammalian cells.

In some embodiments, the subject has chronic inflammation. Chronic inflammation refers to a slow, long-term inflammation lasting several months to years. Chronic inflammation may be associated with a number of inflammation-mediated disorders, conditions, or diseases, such as diabetes, cardiovascular disease, arthritis and joint diseases, allergies, and chronic obstructive pulmonary disease. Risk factors that contribute to chronic inflammation include, obesity, age, diet, smoking, low sex hormones, stress, and sleep disorders.

In other embodiments, the subject has acute inflammation. Tissue damage due to trauma, microbial invasion, or noxious compounds can induce acute inflammation. Acute inflammation may start rapidly, become severe in a short time, and symptoms may last for hours, days, or a few weeks, e.g., 1-6 weeks. In some embodiments, the subject may have an infection, such as a viral or bacterial infection, or suffer from a condition such as sepsis, septic shock, or endotoxemia.

As demonstrated in the Examples, the AdipoR agonists described herein suppress inflammation and endotoxemia. Moreover, the AdipoR agonists also attenuated the association of AdipoR1 and APPL1 via myeloid differentiation marker 88 (MyD88) signaling, thus inhibiting activation of nuclear factor kappa B (NF-κB), mitogen-activated protein kinase (MAPK) and c-Maf pathways and limiting the production of pro-inflammatory cytokines.

Methods for the Treatment of Bone Loss

In some embodiments, the subject is in need of a treatment for bone loss. Bone loss occurs when the body absorbs bone tissue at a faster rate than new bone tissue is formed. Bone tissue exists in a state of dynamic equilibrium involving constant reconstruction via resorption of old bone by osteoclasts and the subsequent reformation of new bone by osteoblasts. Autophagy is the natural, regulated mechanism of a cell that removes unnecessary or dysfunctional components that also plays a major role in maintaining cell homeostasis. It is also a dynamic catabolic process that occurs when cells are exposed to adverse conditions, including nutrient deprivation, hypoxia, radiation and pathogenic infection. Autophagy plays important roles in osteoclast differentiation, formation, and bone loss.

In some embodiments, the subject is need of a treatment for periodontitis. Periodontitis, a common oral disease responsible for tooth loss, is characterized by periodontal inflammation and progressive alveolar bone destruction. Furthermore, periodontitis can trigger an increase in systemic inflammation, negatively impacting cardiovascular, endocrine, and respiratory systems. Twice as prevalent in diabetic patients as in non-diabetics, periodontitis is a common diabetes-associated complication. Type 2 diabetes (T2D)-associated periodontitis is particularly severe and refractory in many cases. Currently, T2D afflicts 40 million Americans, a number expected to increase as the American population ages and becomes more obese. Periodontal inflammation not only stimulates osteoclastogenesis, but also interferes with the coupling of bone formation and bone resorption. T2D-associated periodontitis is associated with supernormal osteoclastogenesis with increased production of pro-inflammatory molecules like interleukin 1β(3 (IL-1β), IL-6, and CC chemokine ligand 2 (CCL2) leading to upregulated production of receptor activator of nuclear factor κB ligand (RANKL) by osteoblasts resulting in osteoclastogenesis and increased numbers of osteoclasts in periodontal tissues.

As demonstrated in the Examples, AdipoR agonists, such as AdipoAI, ameliorate the severity of bone loss and more particularly, T2D-associated periodontitis, by enhancing autophagy in osteoclasts.

ABBREVIATIONS

AdipoAI, Adipo Anti-Inflammation Agonist; LPS, Lipopolysaccharide; APN, Adiponectin; APR, AdipoRon; BMMs, Bone marrow-derived macrophages; PEMs, Peritoneal macrophages; DIO, Diet-induced obesity; i.v., Intravenous; WAT, White adipose tissue.

MISCELLANEOUS

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1

Adipor Agonists Reduce Fasting Blood Glucose Levels and Reduce Inflammation

AdipoR agonists were assessed for their anti-inflammatory properties. The AdipoR agonists, and particularly AdipoAI, strongly suppress inflammation in DIO and endotoxemia mice, as well as in cultured macrophages. The AdipoR agonists also attenuated the association of AdipoR1 and APPL1 via myeloid differentiation marker 88 (MyD88) signaling, thus inhibiting activation of nuclear factor kappa B (NF-κB), mitogen-activated protein kinase (MAPK) and c-Maf pathways and limiting the production of pro-inflammatory cytokines in LPS-induced macrophages. Thus, the AdipoR agonists, such as AdipoAI, suppress inflammation

MATERIALS & METHODS

Synthetic Scheme

Step A: A mixture of tert-butyl 4-aminopiperidine-1-carboxylate (2, 1.0 eq.), 2-chloroacetyl chloride (1, 1.05 eq.) and Et$_3$N (2 eq.) was stirred in CH$_2$Cl$_2$ (0.5 M) at room temperature for 5 h. Evaporated to provide crude compound 3, which is used for the next step without further purification;

Step B: A mixture of compound 3 (1.1 eq.), the corresponding ArOH (1.0 eq) and K$_2$CO$_3$ (5 eq) was refluxed in CH$_3$CN overnight. TLC shows the reaction completed then cooled. The reaction mixture was evaporated and to the residue was added water followed by extraction with CH$_2$Cl$_2$ (×3), washed with brine and dried over anhydrous Na$_2$SO$_4$. Filtration and evaporation provided the crude compound 4 as light yellow solid, which is used for the next step without further purification.

Step C: To a solution of compound 4 in CH$_2$Cl$_2$ (0.5 M) was added HCl (4 M, in EtOAc, 10 eq) then stirred at room temperature for 2 h. Then the solution was evaporated and to the residue was added CH$_3$CN (0.5 M), K$_2$CO$_3$ (5 eq) and corresponding benzyl chloride (1.1 eq). The reaction mixture was refluxed until TLC shows compound 4 disappeared. The reaction mixture was evaporated and to the residue was added water followed by extraction with CH$_2$Cl$_2$ (×3), washed with brine and dried over anhydrous Na$_2$SO$_4$. Filtration and evaporation followed by column chromatography to provide the target compound as white or light yellow solid.

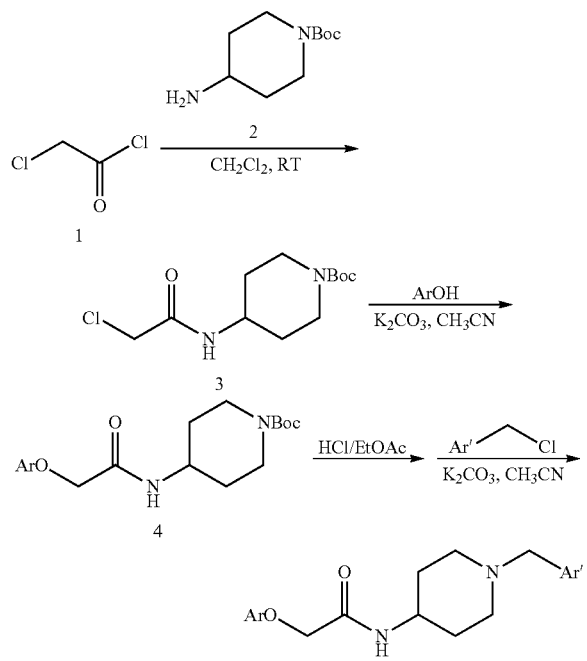

Successful synthesis was confirmed by high-performance liquid chromatography (HPLC). AdipoAI was confirmed to have >95% purity by HPLC.

Reagents and Antibodies

Mouse Colony Stimulating Factor-1 (MCSF-1) was purchased from PeproTech Inc (Rocky Hill, N.J., USA). AdipoRon was purchased from AdipoGen Life Sciences (San Diego, Calif., USA). LPS (*Escherichia coli* 0111: B4) was purchased from Sigma-Aldrich (St. Louis, Mo., USA). Antibodies for β-actin (cat #ab8226, RRID: AB_306371), AdipoR1 (cat #ab126611, RRID: AB_11129655), AdipoR2 (cat #ab77613, RRID: AB_2222054), APPL2 (cat #ab154545, RRID: AB_2861345) and c-maf (cat #ab77071, RRID: AB 1951643) were purchased from Abcam (Cambridge, Mass., USA). Antibodies for APPL1 (cat #3276, RRID: AB_2258386), MyD88 (cat #4283, RRID: AB_10547882), phospho-NF-κB p65 (cat #3034, RRID: AB_330561), NF-κB p65 (cat #8242, RRID: AB_10859369), phosphor-IRAK4 (cat #11927, RRID: AB_2797770), IRAK4 (cat #4363, RRID: AB_2126429), phosphor-p38 MAPK (cat #9211, RRID: AB_331614), p38 MAPK (cat #8690, RRID: AB_10999090), phosphor-AKT (cat #4060, RRID: AB_2315049), PI3K p85 α (cat #13666, RRID: AB_2798288), β-catenin (cat #8480, RRID: AB_11127855) and F4/80 (cat #70076, RRID: AB_2799771) were purchased from Cell Signaling Technology (Danvers, Mass., USA); Antibodies for Lamin B1 (cat #sc-377000, RRID: AB_2861346), TLR4 (cat #sc-293072, RRID: AB_10611320), phosphor-ERK (cat #sc-7383, RRID: AB_627545), ERK (cat #sc-514302, RRID: AB_2571739), phosphor-JNK (cat #sc-12882, RRID: AB_654355), JNK (cat #sc-7345, RRID: AB_675864), AKT (cat #sc-81434, RRID: AB_1118808) and m-IgGκ BP-HRP antibody (cat #sc-516102, RRID: AB_2687626) were purchased from Santa Cruz Biotechnology, Inc. (Dallas, Tex., USA). Normal Rabbit IgG (cat #NI01, RRID: AB_490574) was purchased from EMD Millipore (Billerica, Mass., USA).

Cell Culture of RAW 264.7 Macrophages

RAW 264.7 macrophage cell line was purchased from ATCC (Manassas, Va., USA) and maintained in DMEM (Gibco, Life Technologies, Carlsbad, Calif., USA) supplemented with 10% (v.v-1) FBS (Gibco, Life Technologies) and 1% (v.v-1) penicillin/streptomycin (Gibco, Life Technologies). The cells were routinely cultured in an incubator at 37° C. in a humidified atmosphere of 5% CO$_2$.

Isolation and Culture of Bone Marrow-Derived Macrophages (BMMs)

BMMs were obtained by isolating bone marrow from 4 to 8-week-old C57BL/6J mice (purchased from the Jackson Laboratory, Bar Harbor, Me., USA) and culturing in the presence of 10 mg/ml recombinant MCSF-1 (PeproTech Inc, Rocky Hill, N.J., USA) for 3 days. On day 3, BMMs were harvested and plated in complete DMEM media containing MCSF-1. All the animal experiments were conducted under the guidelines issued by the Tufts University Institutional Animal Care and Use Committee.

Isolation and Culture of Murine Peritoneal Macrophages (PEMs)

Murine peritoneal macrophages were isolated as described previously (Pun et al., 2015). Briefly, 6 to 7-week-old male C57BL/6J mice were treated by i.p. injection with 1 mL of 4% (w.v-1) thioglycolate medium (Difco, Detroit, Mich., USA) to induce the accumulation of macrophages in the peritoneum region. After 3 days of thioglycolate injection, peritoneal macrophages (PEMs) were extracted with ice-cold HBSS (Sigma-Aldrich, St Louis, Mo., USA) and centrifuged at 300×g for 5 min. The cell pellet was suspended in red blood cell lysis buffer (BioLegend, San Diego, Calif., USA) to remove contaminated red blood cells. After centrifugation, the remaining cell pellet was mixed with RPMI 1640 medium (Gibco, Life Technologies, Carlsbad, Calif., USA) containing 10% (v.v-1) fetal bovine serum (FBS) and 1% (v.v-1) penicillin/streptomycin. The cells were then seeded onto a culture dish (100 mm) at a density of $1\times10^7$ cells per dish and incubated in an incubator (37° C.) under a humidified atmosphere of 5% $CO_2$ for further experiments.

To examine the impact of AdipoAI on gene expression in vivo, 6- to 7-week-old male C57BL/6J mice were randomly divided into 2 groups (control and AdipoAI-treated groups with 5 mice per group). On day 1, mice were injected i.p. with 1 mL of 4% thioglycolate solution. On day 2, mice were injected i.p. with AdipoAI at a concentration of 25 mg/kg body weight. On day 3 (after 24 h treatment with AdipoAI), peritoneal macrophages were isolated and cultured for 2 h. Cells were then washed with cold phosphate buffer saline (PBS) and used for different experiments.

Cytotoxicity Assays

Raw264.7 cells were seeded at $2\times10^3$ cells/well in 96-well plates for 16 hours and then serum-starved for 6 hours. Cells were maintained in DMEM in the presence of different concentrations of APR (AdipoGen Life Sciences, San Diego, Calif., USA) and compounds for 24 hours. Cytotoxicity was determined with the Cell Counting Kit-8 (CCK-8 kit, Dojindo, Santa Clara, Calif., USA) following the manufacturer's recommendations. The detailed group assignment is shown in the individual figure legends.

RNA Isolation, and Reverse Transcription and Real-Time Quantitative PCR (qRT-PCR)

Total RNA of cells was extracted using Quick-RNA Miniprep Kit (ZYMO Research, Irvine, Calif., USA) and total RNA from mouse tissues was prepared with TriZol reagent (Life Technologies) according to the manufacturer's instructions followed by qRT-PCR assays as described previously (L. Zhang et al., 2014). 1 µg of total RNA was used for reverse transcription using the M-MLV Reverse Transcriptase (Thermo Scientific, Waltham, Mass., USA) according to the manufacturer's protocol using PowerUp SYBR Green Master Mix (Thermo Scientific) on a Bio-Rad iQ5 thermal cycler (Bio-Rad Laboratories, Hercules, Calif., USA). Differences in expression were evaluated by the comparative cycle threshold method using GAPDH or β-actin as a control. The primer sequences used for the qRT-PCR experiments are listed in supplemental Table 1.

TABLE 1

Primers used in the qRT-PCR experiments

| Gene | Forward primer | Reverse primer |
| --- | --- | --- |
| qPCR IL-6 | TCCAGTTGCCTTCTTGGGAC (SEQ ID NO: 1) | AGTCTCCTCTCCGGACTTGT (SEQ ID NO: 2) |
| qPCR IL-1 β | GTCAACGTGTGGGGGATGAA (SEQ ID NO: 3) | AAGCAATGTGCTGGTGCTTC (SEQ ID NO: 4) |
| qPCR IL-1 0 | GCTCTTACTGACTGGCATGAG (SEQ ID NO: 5) | CGCAGCTCTAGGAGCATGTG (SEQ ID NO: 6) |
| qPCR TNF- α | TGTCCCTTTCACTCACTGGC (SEQ ID NO: 7) | CATCTTTTGGGGGAGTGCCT (SEQ ID NO: 8) |
| qPCR AdipoR1 | TCTTTTTGGGTGCAGTGCT (SEQ ID NO: 9) | GCAATTCCTGAATAGTCCAGTT (SEQ ID NO: 10) |
| qPCR AdipoR2 | GGGCATTGCAGCCATTAT (SEQ ID NO: 11) | TAGGCCCAAAAACACTCCTG (SEQ ID NO: 12) |
| qPCR APPL1 | GCTTTGTTAGAACCTCTACTGGG (SEQ ID NO: 13) | GGTCAGGCAGATATAAAGGGTCA (SEQ ID NO: 14) |
| qPCR APPL2 | CACCCTCACAGATTACACCAAC (SEQ ID NO: 15) | GGAGAACCATAGTGTCTGCCAG (SEQ ID NO: 16) |
| qPCR MyD88 | AGGACAAACGCCGGAACTTTT (SEQ ID NO: 17) | GCCGATAGTCTGTCTGTTCTAGT (SEQ ID NO: 18) |
| qPCR c-Maf | GGAGACCGACCGCATCATC (SEQ ID NO: 19) | TCATCCAGTAGTAGTCTTCCAGG (SEQ ID NO: 20) |
| qPCR GAPDH | AGGTCGGTGTGAACGGATTTG (SEQ ID NO: 21) | TGTAGACCATGTAGTTGAGGTCA (SEQ ID NO: 22) |
| qPCR β-actin | AGAGGGAAATCGTGCGTGAC (SEQ ID NO: 23) | CAATAGTGATGACCTGGCGT (SEQ ID NO: 24) |
| siRNA AdipoR1 | GACUUGGCUUGAGUGGUGU (SEQ ID NO: 25) | ACACCACUCAAGCCAAGUC (SEQ ID NO: 26) |
| siRNA AdipoR2 | AGAGUGAAGCCACCUGGUU (SEQ ID NO: 27) | AACCAGGUGGCUUCACUCU (SEQ ID NO: 28) |
| siRNA APPL1 | GGUCUUUACUUGGUGUAUUU (SEQ ID NO: 29) | AAUACACCAAGUAAAGACCUU (SEQ ID NO: 30) |
| siRNA APPL2 | GCACUUUGAAGGAUCUCUUU (SEQ ID NO: 31) | AAGAGAUCCUUCAAAGUGCUG (SEQ ID NO: 32) |

TABLE 1-continued

Primers used in the qRT-PCR experiments

| Gene | Forward primer | Reverse primer |
| --- | --- | --- |
| siRNA MyD88 | CUAUAUGCGACUAUACCAAUU (SEQ ID NO: 33) | UUGGUAUAGUCGCAUAUAGUG (SEQ ID NO: 34) |
| siRNA c-Maf | GUUAAUGACUUCGAUCUGAUU (SEQ ID NO: 35) | UCAGAUCGAAGUCAUUAACAU (SEQ ID NO: 36) | mRNA Microarray Analysis

Raw264.7 cells were stimulated with AdipoAI for 24 h followed by incubation with 100 ng/mL LPS (*Escherichia coli* 0111: B4, Sigma-Aldrich, St. Louis, Mo., USA) for an additional 6 h. Detailed information of the 4 groups are shown in the figure legends. Total RNA of cells was extracted, and 5 µg total RNA from each cell sample was sent to Arraystar Inc. (Rockville, Md., USA) for microarray analysis. Image processing and data extraction and analysis also were performed by Arraystar Inc. using their established protocols.

Enzyme-Linked Immunosorbent Assay (ELISA)

Cell culture media and mouse serum were collected and used for the measurement of cytokines secretion using ELISA kits (Abcam), according to the manufacturer's instructions.

Preparation of Protein Extracts and Western Blot Analysis

Total cellular extracts were prepared using RIPA Lysis and Extraction Buffer containing three Protease Inhibitors (Thermo Scientific). Cytoplasmic and nuclear extracts were purified using NE-PER™ Nuclear and Cytoplasmic Extraction Reagents (Thermo Scientific). Experimental details of western blotting are in accordance with British Journal of Pharmacology guidelines (Alexander et al., 2018) and western blot analyses were performed as previously described (J. Zhang et al., 2017). Briefly, the total protein concentration was quantified using BCA kit (P1511; Applygen Technologies Inc., Beijing, China). The samples were separated by SDS-PAGE and electrophoretically transferred to a polyvinylidene difluoride membrane (Merck Millipore, Darmstadt, Germany). The membranes were blocked with 5% skim milk for 1 to 2 hr at room temperature. Then the blots were incubated with primary antibodies against AdipoR1 (1:1000), AdipoR2 (1:1000), APPL1 (1:1000), APPL2 (1:1000), MyD88 (1:1000), phospho-NF-κB p65 (1:1000), NF-κB p65 (1:1000), phosphor-IRAK4 (1:500), IRAK4 (1:1000), phosphor-p38 MAPK (1:1000), p38 MAPK (1:1000), phosphor-AKT (1:1000), AKT (1:500), phosphor-ERK (1:500), ERK (1:500), phosphor-JNK (1:500), JNK (1:500), PI3K p85 α (1:1000), β-catenin (1:1000), Lamin B1 (1:5000), TLR4 (1:500), c-Maf (1: 2000) and β-actin (1:20, 000) overnight at 4° C. After washed with Tris-buffered saline with Tween (TBST) buffer three times for 5 min, the blots were incubated with HRP-conjugated anti-rabbit (1:10, 000) at room temperature for 45 min. Finally, the protein bands were visualized using ECL chemiluminescence reagents from Thermo Scientific. All bands were quantification analyzed using Image J (ImageJ, RRID: SCR 003070).

Immunoprecipitation (IP) Assays

The RAW 264.7 macrophages were seeded at a density of 6×106 cells per 100 mm dish. After overnight culture, the cells were stimulated with APR or AdipoAI for 24 h followed by incubation with LPS (100 ng/mL) for an additional 6 h. Cells were then lysed on ice with lysis buffer (25 mM Tris, 150 mM NaCl, 1 mM EDTA, 1% NP-40, 5% glycerol, 45 Mm octyl glucoside) supplemented with protease and phosphatase inhibitors cocktails. IP was performed with Protein A/G Magnetic Beads (EMD Millipore) and 1 µg of specified antibodies (APPL1 or MyD88) at 4° C. overnight. The immunoprecipitates were washed with lysis buffer and further analyzed by polyacrylamide gel electrophoresis and Western blot analyses. The Clean-Blot IP Detection Kit (Thermo Scientific) was used as the secondary antibody. Normal Rabbit IgG (EMD Millipore) was used as a negative control in all IP experiments.

Hematoxylin and Eosin (H&E) and Immunohistochemical (IHC) Staining

Mouse soft tissue samples were prepared for H&E staining as previously described (Lian et al., 2019). IHC was performed using a Histostain-SP Kit (Life Technologies) following the manufacturer's recommendations and British Journal of Pharmacology guidelines (Alexander et al., 2018). Primary antibodies for F4/80 (1:250) and c-Maf (1:250) were purchased from Cell Signaling Technology and Abcam, respectively. Digital images of stained tissues were taken with an Olympus BX53 microscope and quantification analyzed by a blinded operator using ImageJ software (ImageJ, RRID: SCR_003070).

Transient Transfection with siRNAs

Macrophages were seeded at a density of $5 \times 10^5$ cells/well in 12-well plates. After overnight incubation, the cells were transfected for 24 h with siRNAs targeting specific genes or scrambled control siRNAs using HiPerFect Transfection Reagent (Qiagen, Hilden, Germany) according to the manufacturer's guidelines. Gene silencing efficiency was monitored by qPCR or Western blot analysis. The siRNA duplexes used in this study were chemically synthesized by Thermo Scientific. The sequences of the siRNAs are listed in Table 1.

In Vivo Investigation in Mouse Models

The Ethics Committee on the Use and Care of Animals at Tufts University approved the study protocol (Boston, Mass., USA). The animals received humane care according to the criteria outlined in the Guide for the Care and Use of Laboratory Animals prepared by the National Academy of Sciences and published by the National Institutes of Health. All experiments involving animals or animal tissue are reported in compliance with the guidelines of ARRIVE and BJP (Kilkenny et al., 2010; McGrath and Lilley, 2015). Experimental protocols and design adhere to BJP guidelines (Curtis et al., 2015). Wild-type (WT, C57BL/6J, Jax #000664), DIO (Jax #380050), and APN KO (Jax #008195) mice were purchased from the Jackson Laboratory. The DIO mice were fed with a high-fat diet (containing 60% kcal from fat; Jackson Laboratory) at 6 weeks of age and later. The WT mice were fed with ordinary diet as normal chow (NC)-fed mice, and APN KO mice were maintained and fed with an NC diet as previously described (Tu et al., 2011). For the LPS-induced endotoxemia model, male C57BL/6 mice aged 8 weeks received oral gavage with APR (50 mg/kg body weight) or AdipoAI (25 mg/kg body weight) for 24 h before by LPS (20 mg/kg body weight) treatment which was administered intraperitoneally whereas control animals were treated with equivalent volumes of normal PBS. Mouse survival in each group was monitored and recorded up to 84 h. All mice were killed at 1 h for detection of activation of inflammatory genes, at 6 h for determination of inflammatory factors in serum, and at 24 h for histological evaluation. The detailed groups and the number of mice included are shown in the figure legends. Animal data were excluded from experiments based on pre-established criteria of visible abnormal tissue structure during sample harvest or other health issues, including fighting wounds.

Statistical Analysis

All studies were designed to generate groups of equal size, using randomisation and blinded analysis. Group size is the number of independent values, and that statistical analysis was done using these independent values. Sample size of each protocol was determined on the basis of similar previous studies (Gu et al., 2017; Wang et al., 2017). The data and statistical analysis comply with the recommendations on experimental design and analysis in pharmacology (Curtis et al., 2018). Data are expressed as the mean±SEM and GraphPad Prism software (GraphPad Software Inc., La Jolla, Calif., USA) was used for statistical analyses. Statistical analysis was undertaken only for studies where each group size was at least n=5, and not subjected to statistical analysis where each group sizes was n<5. Statistical significance was calculated using two-tailed Student's t-tests for comparisons between two groups and one-way ANOVA (Analysis Of Variance) with post-hoc Tukey HSD (Honestly Significant Difference) test using correction for comparisons among more than two groups. Post-hoc tests were run only if F achieved P<0.05 and there was no significant variance inhomogeneity. P<0.05 was considered statistically significant. To control for unwanted sources of variation, normalization of the data was carried out. The mean values of the control group were normalized to 1. In the figures, the Y-axis shows the ratio of the experimental group to that of the corresponding matched control values. When outliers are included or excluded in analysis, it is declared within the figure legend. For animal survival analysis, the Kaplan-Meier method was employed to generate graphs, and the survival curves were analyzed using log-rank analysis. Band intensity in western blot images was quantified with Image J Software.

Results

Design of AdipoR Agonists and Evaluation of the Anti-Inflammatory Properties

To develop orally-active small molecule compounds with potent anti-inflammatory effects, agonists of APR were designed and synthesized and compared them with APR. Firstly, their ability to inhibit the mRNA expression of proinflammatory cytokines IL-6 and IL1-β in LPS-stimulated RAW 264.7 macrophages was investigated. Compounds 3 and 5 (at 5 µM) were found to exhibit stronger inhibitory effects than APR (at 20 µM) (FIG. 1a), particularly the compound 3. Therefore, compound 3 is designated as AdipoAnti-Inflammation Agonist (AdipoAI).

Treatment of RAW264.7 macrophages with increasing concentrations of AdipoAI decreased LPS-stimulated IL-6 and IL-10 mRNA expression in a dose-dependent fashion (FIG. 1b). To determine whether AdipoAI, compound 5, or APR could be mediating their anti-inflammatory effects by decreasing Raw264.7 cell number, a CCK-8 cytotoxicity assay was conducted. Results revealed that neither of the 3 small molecules mediated significant cytotoxic effects at 40 µM or lower concentrations (FIG. 1c).

Because AdipoAI exhibited the strongest inhibitory effects on LPS-stimulated IL-6 and IL-1β expression in BMMs (FIG. 1d) comparing with compound 5 and APR, AdipoAI was chosen to perform the remaining experiments in this study.

AdipoAI Inhibits LPS-Stimulated Inflammatory Responses in Macrophages

Figure 2:
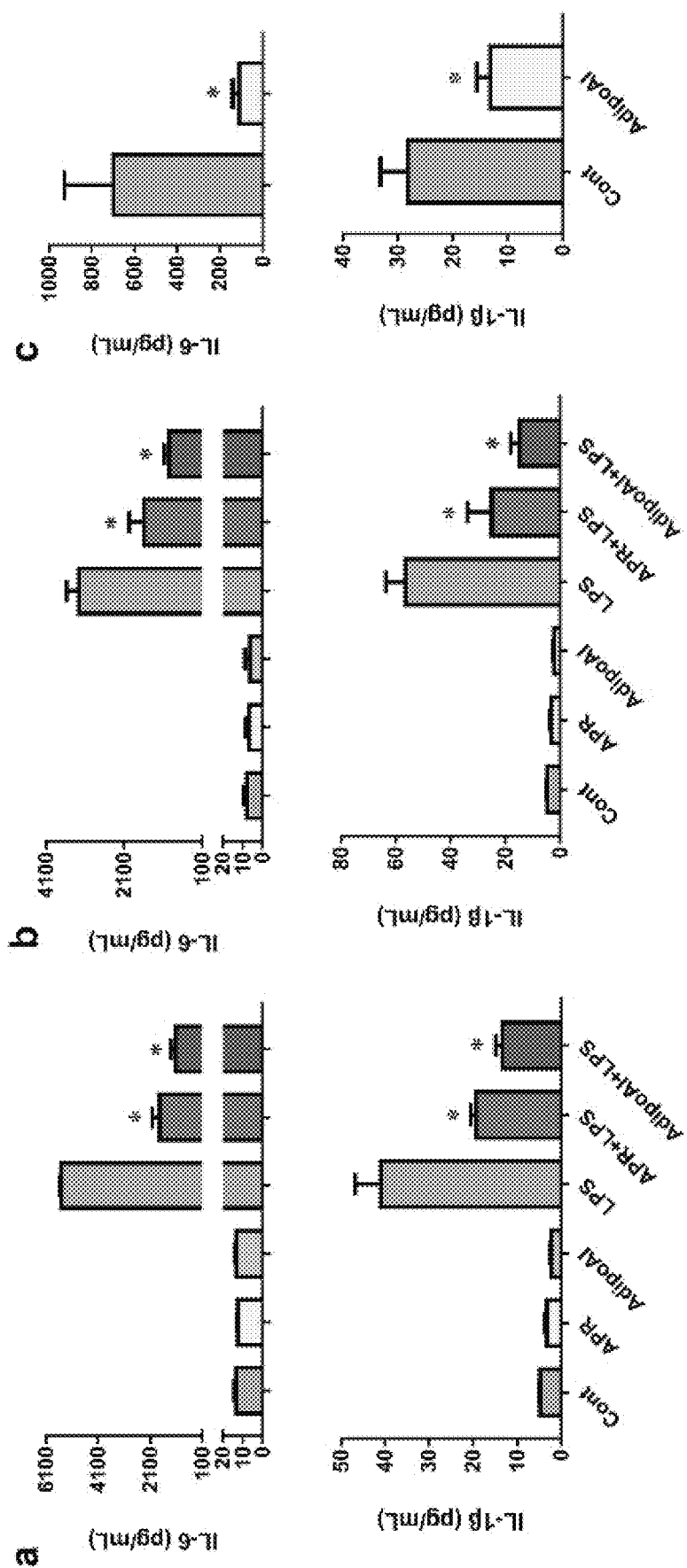
FIG. 2 AdipoAI suppresses LPS-stimulated inflammatory responses in macrophages. (a) Raw264.7 cells or (b) BMMs were pretreated with APR (20 μM) or AdipoAI (5 μM) for 24 h followed by incubation with LPS (100 ng/mL) for additional 6 h for the measurement of IL-6 and IL-1β in supernatants by ELISA. Data were expressed as the mean±SEM at five biological independent experiments. One-way ANOVA test for multiple-group comparisons, * vs. LPS group, *P<0.05, significant differences between each indicated group. (c) PEMs were isolated from C57BL/6J mice (n=5 mice/group) were injected i.p. with 1 mL 4% thioglycolate solution or AdipoAI (25 mg/kg) for the measurement of IL-6 and IL-1β. The amounts of IL-6 and IL-1β in supernatant were measured by ELISA. Data were expressed as the mean±SEM (n=5). Two-tailed Student's t-test for two groups, *P<0.05, significant differences between each indicated group. (d-f) Impact of AdipoAI on basal (d) and LPS-induced expression of an array of proinflammatory cytokines, chemokines, and receptors (e,f) in Raw264.7 cells (4 groups and 3 biological replicates/group). Data analyses were performed according to the manufacturer's instructions with their web-based software package (www.qiagen.com/us/shop/genes-and-pathways/data-analysis-center overview-page/). (g) Differentiated expressed genes annotated to a gene-ontology term and example genes by gene-ontology—enrichment analysis of each component. (brown: LPS vs control; black: AdipoAI+LPS vs LPS). (h) Differentially expressed M1 and M2 genes are shown according to the microarray databases. No statistical analysis for n=3.
Figure 2:
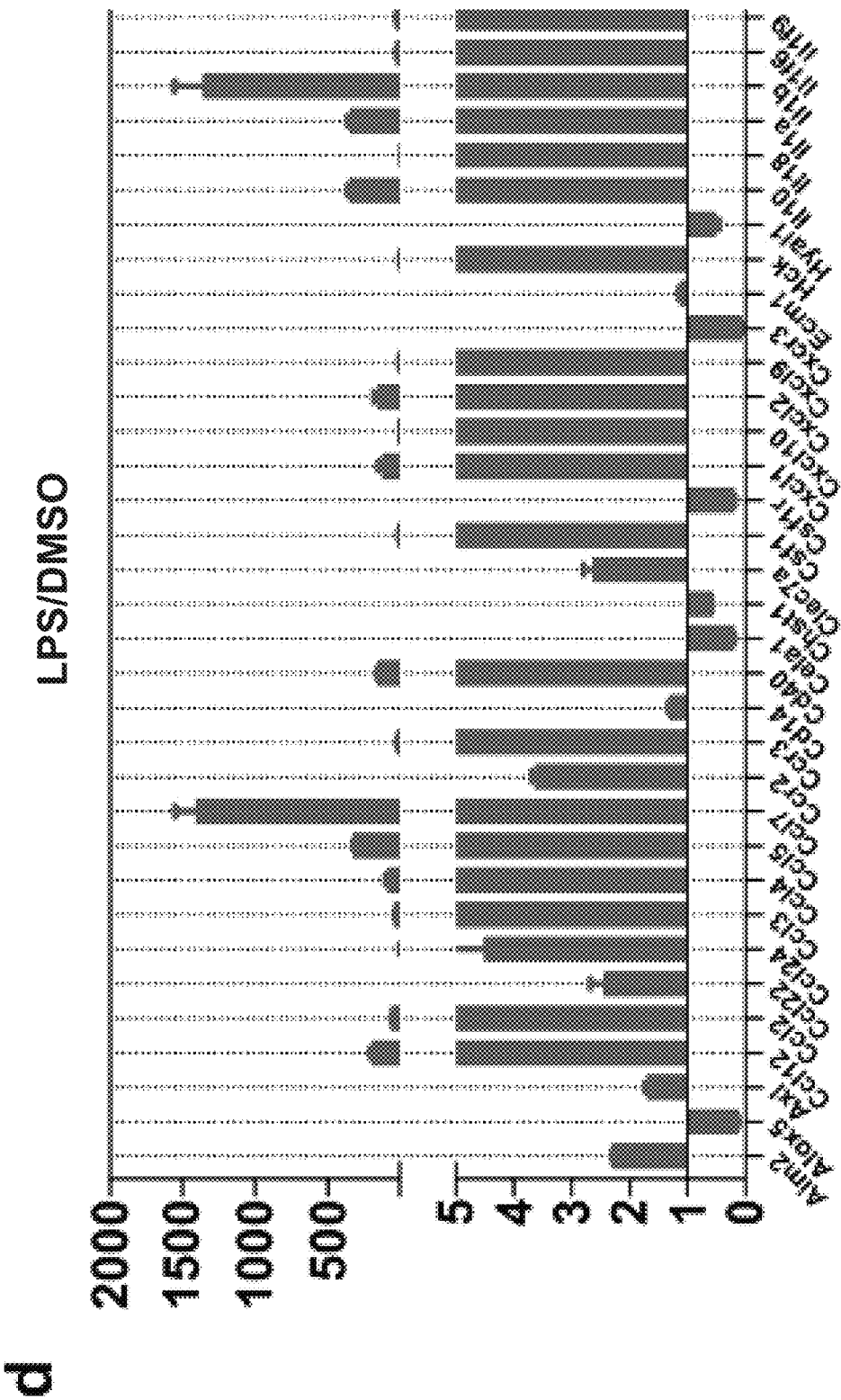
Figure 2:
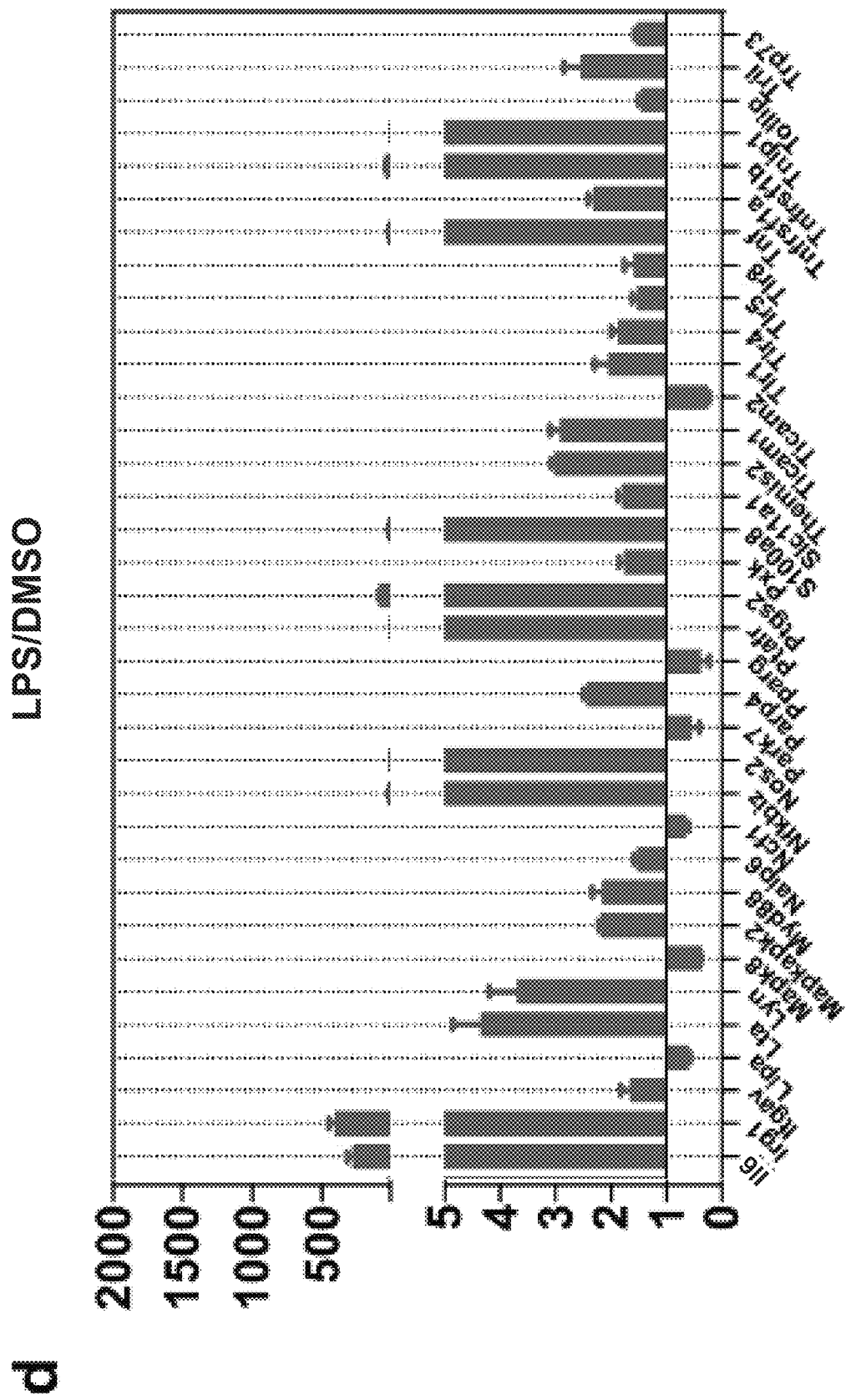
Figure 2:
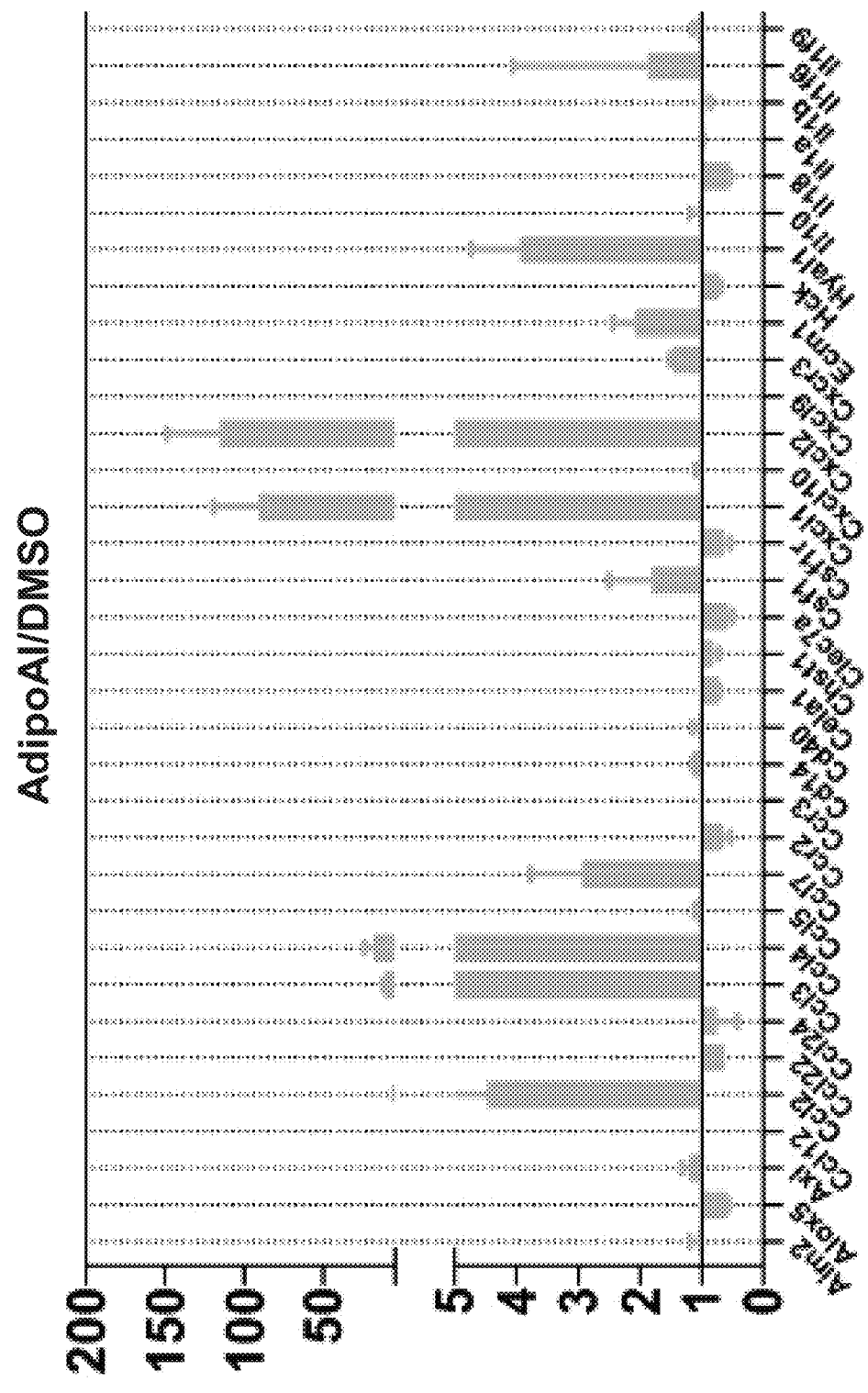
Figure 2:
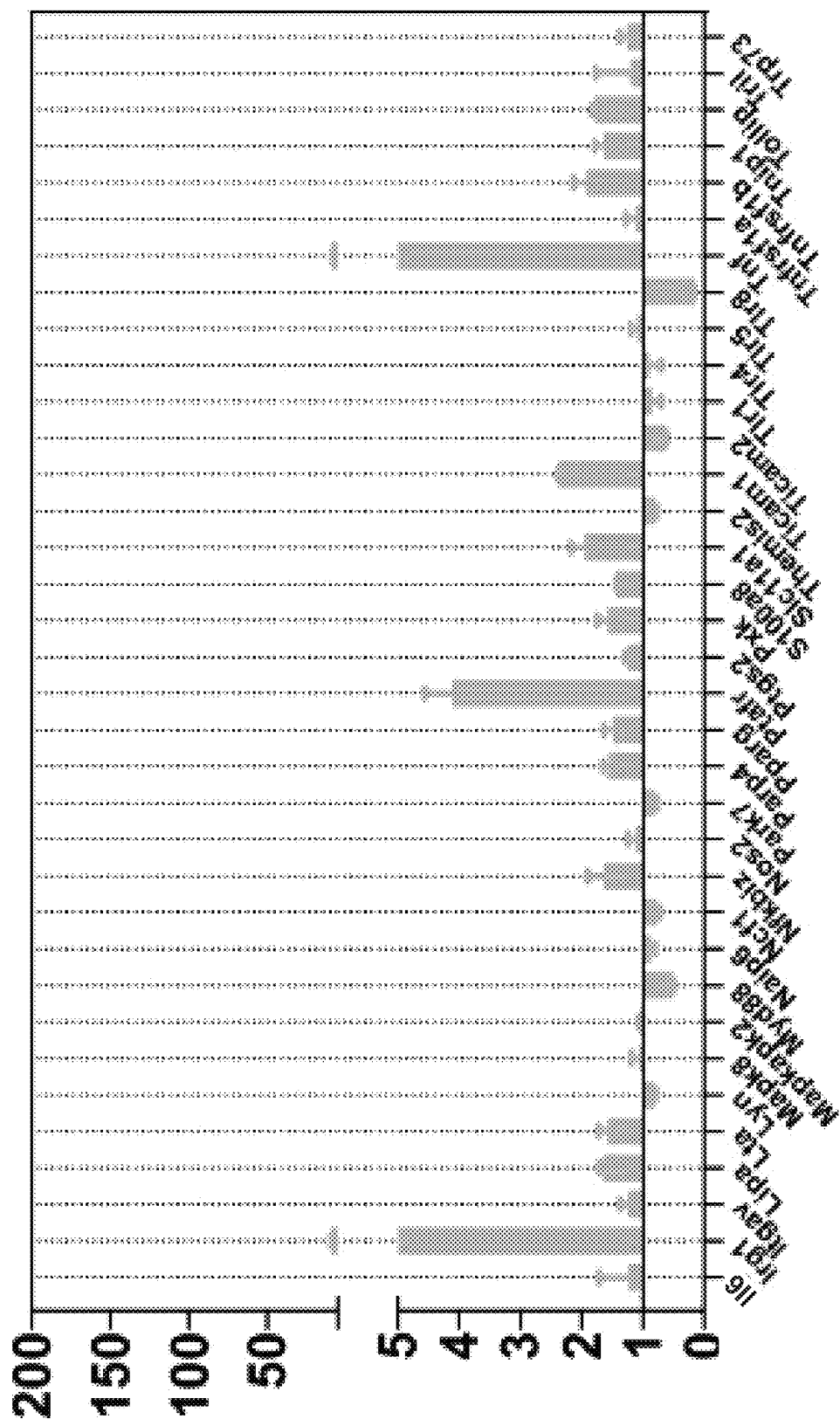
Figure 2:
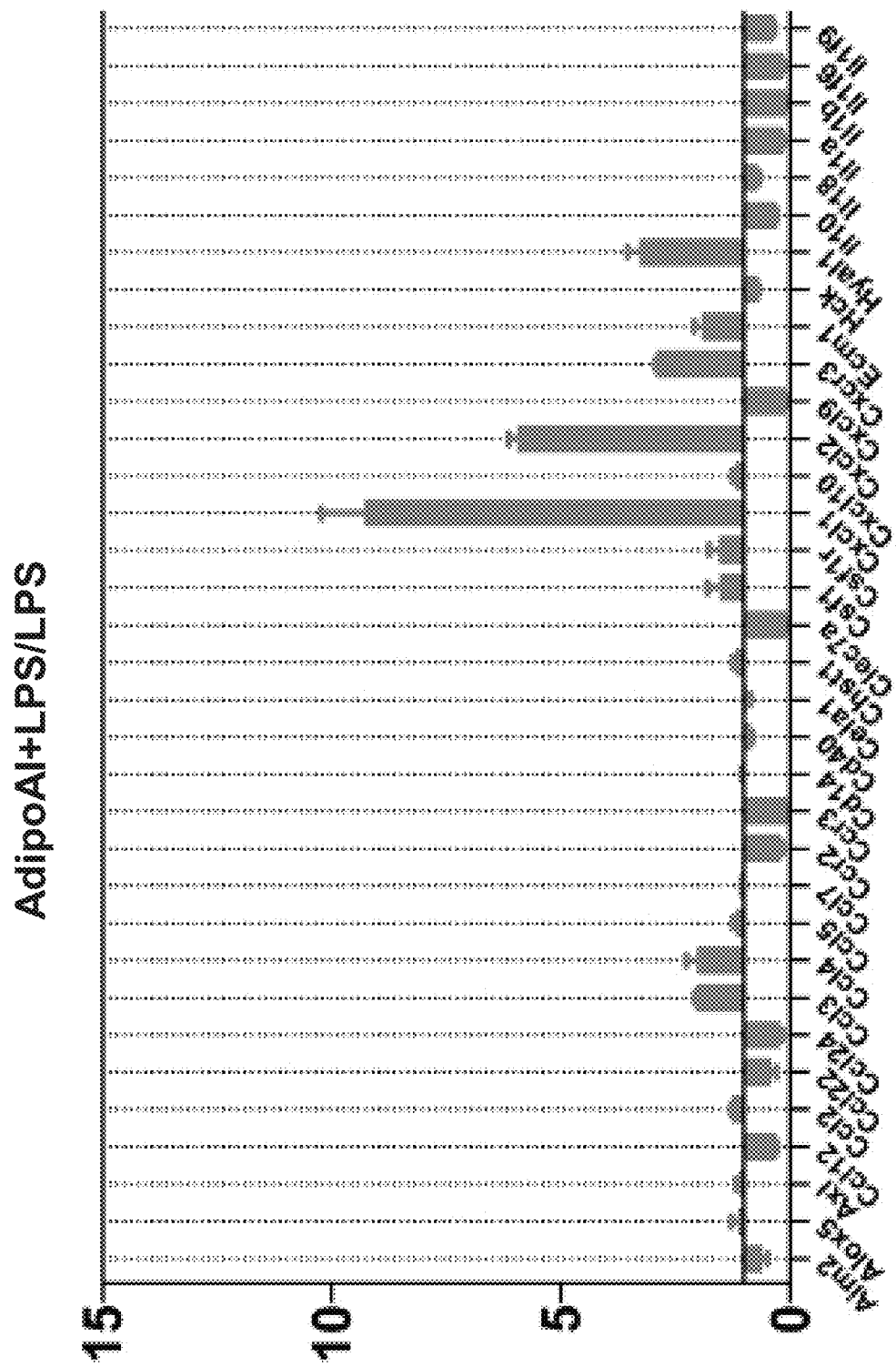
Figure 2:
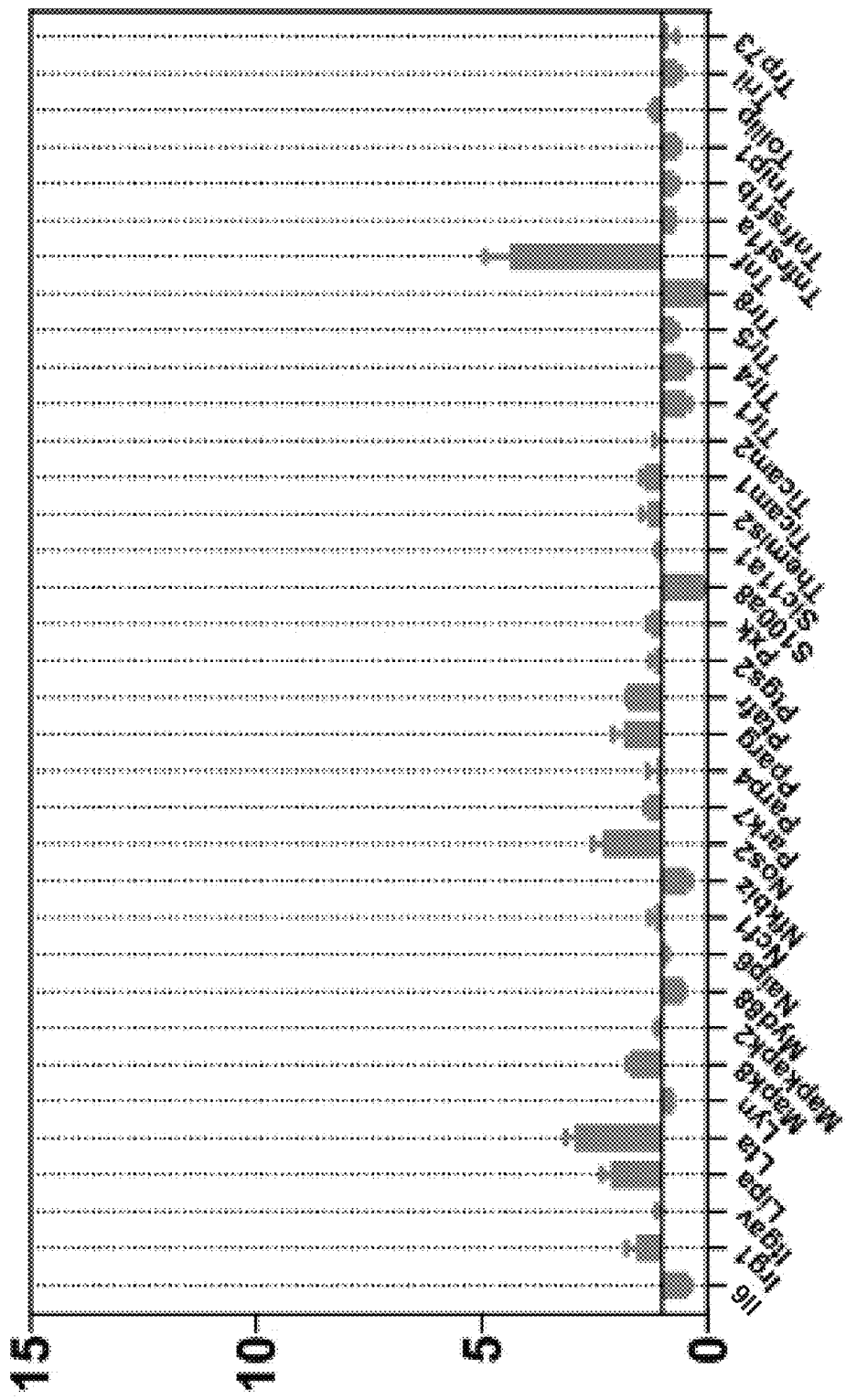
Figure 2:
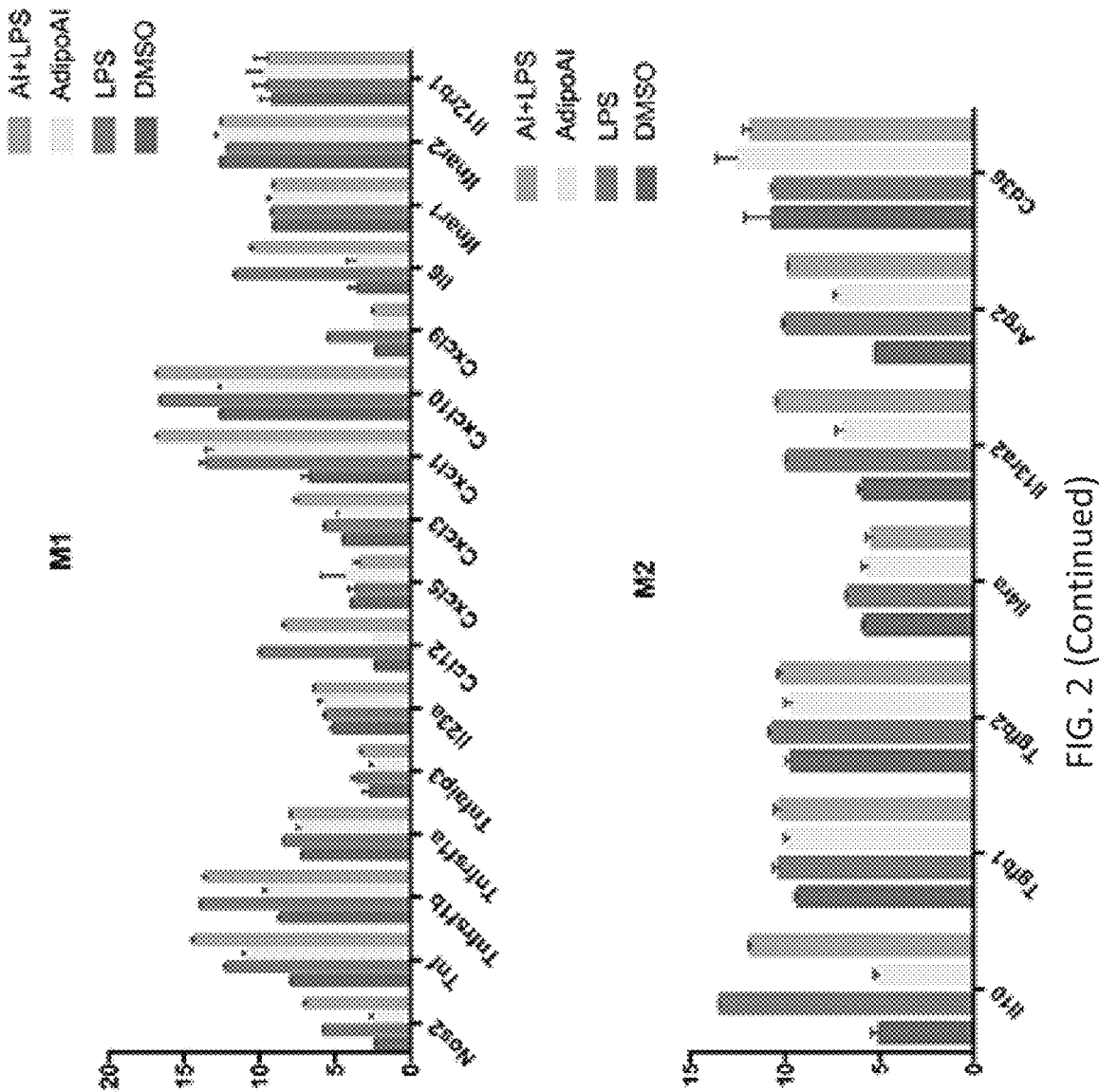

To further evaluate the anti-inflammatory impact of AdipoAI in LPS-induced macrophages, the secreted production of IL-6 and IL-1β by ELISA was measured. Results revealed that treatment with AdipoAI for 24 h followed by incubation with LPS for 6 h decreased IL-6 and IL-1β protein levels in Raw264.7 and BMMs (FIG. 2a, b). The production of IL-6 and IL-1β by peritoneal macrophages (PEMs) isolated from AdipoAI-treated mice (20 mg/kg body weight) was evaluated, and it was found that AdipoAI reduced IL-6 and IL-1β (FIG. 2c).

mRNA microarray profiles and patterns in LPS-stimulated Raw264.7 cells were evaluated, and it was found that LPS stimulated the expression of an array of proinflammatory cytokines, chemokines, and receptors (FIG. 2d), whereas AdipoAI decreased the expression of the same genes to near basal levels (FIGS. 2e, f, and g).

M1 macrophages are known to be involved in host defense and pathogen removal, while M2 macrophages participate in tissue repair (Xuan et al., 2016). Moreover, APN can contribute to M2 macrophage induction (Lovren et al., 2010; Mandal, Pratt, Barnes, McMullen, & Nagy, 2011; Ohashi et al., 2010). However, AdipoAI treatment in LPS-induced Raw264.7 cells did not alter the expression of M1 or M2 macrophage-related genes (FIG. 2h).

AdipoAI Decreases Systemic Inflammation in DIO Mice

Figure 13:
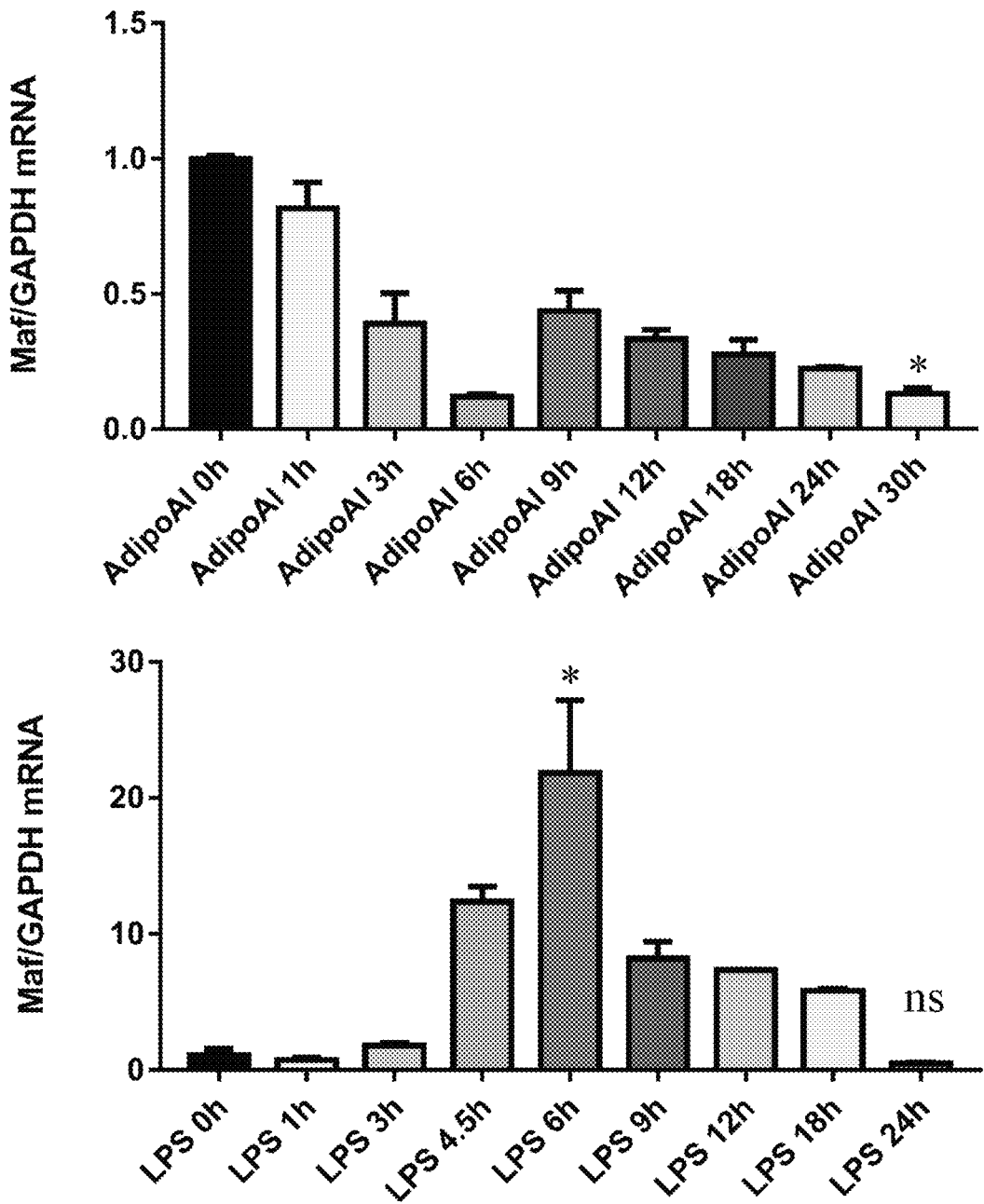
FIG. 13 Raw264.7 cells were treated with AdipoAI (5 μM) or LPS (100 ng/mL) for different times to measure c-Maf mRNA expression by qRT-PCR. Data were expressed as the mean±SEM at five biological independent experiments. One-way ANOVA test for multiple-group comparisons, * $P<0.05$, significant differences between each indicated group. ns: not significant.

Low-grade systemic inflammation is a significant characteristic of obesity (Ouchi & Walsh, 2007). To investigate the impact of AdipoAI in systemic inflammation, a DIO mouse model was chosen, which has been used by other investigators to study and research prediabetes and diabetes-related metabolic syndrome (Wu et al., 2019), as well as chronic systemic inflammatory response (Ohashi, Shibata, Murohara, & Ouchi, 2014). In the present work, DIO and WT mice were treated with APR or AdipoAI via oral gavage for 14 days, and then the expression of proinflammatory and anti-inflammatory cytokine expression was evaluated. It was found that AdipoAI inhibited mRNA expression of IL-6 (Il6) and IL-1β (Il1β) but not that of TNF-α or IL-10 in the white adipose tissue (WAT), spleen, or bone marrow of DIO mice (FIGS. 3a, b, and c). Furthermore, AdipoAI reduced IL-6 and IL-1β levels in the serum of AdipoAI-treated DIO mice (FIG. 3d). In agreement with AdipoAI anti-inflammatory potential, a decreased quantity of megakaryocytes and macrophages in the spleen of AdipoAI-treated DIO mice by H&E and IHC (F4/80) staining was detected (FIG. 3e, f and FIG. 13).

AdipoAI Protects Against LPS-Induced Endotoxemia and Organ Dysfunction

Systemic inflammatory states, namely, sepsis, septic shock, and endotoxemia, influence most body organs, including the lung, spleen, liver, and white adipose tissue (WAT) (Salomao et al., 2012). The effects of AdipoAI in WT mice with LPS-induced endotoxemia was investigated by treating mice with AdipoAI via oral gavage for 24 h before LPS challenge. Treatment with AdipoAI decreased mRNA levels of proinflammatory genes in various tissues, with lung exhibiting the sharpest drop, followed by the spleen, WAT, and liver (FIG. 4a). Whereas only 12.5% of the vehicle-treated mice survived 84 h post-LPS challenge, the survival rate of AdipoAI-treated group was 40% (FIG. 4b). AdipoAI treatment also reduced serum levels of pro-inflammatory cytokines IL-6 and IL-1β at 6 h post-LPS administration (FIG. 4c).

Figure 14:
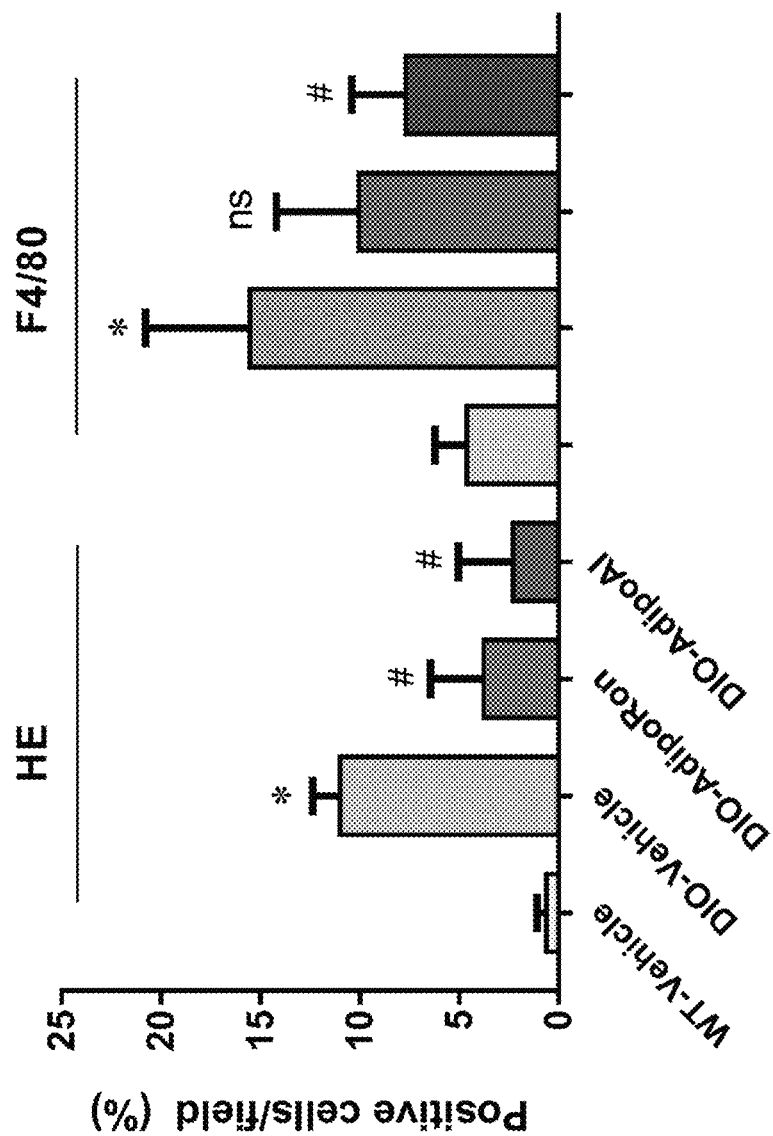
FIG. 14 Quantitative analysis of positive cells of HE staining and F4/80 positive cells in FIG. 3e, f. Data are expressed as mean±SEM (n=6). One-way ANOVA test for multiple-group comparisons, * vs. WT-Vehicle group, #vs. DIO-Vehicle group. */#$P<0.05$, significant differences between each indicated group. ns: not significant.

Mice challenged with LPS have been reported to exhibit varying degrees of acute inflammation in the lung, spleen, liver, and WAT tissues (Du et al., 2017). LPS-treated mice showed exacerbated lung inflammation, hemorrhage, and alveolar septal thickening, whereas AdipoAI-treated mice had fewer lung lesions and decreased inflammatory cell infiltration (FIG. 4d). Furthermore, the LPS-induced spleen, liver, and WAT injury and activation of inflammatory responses were also alleviated in AdipoAI-treated mice (FIG. 4d and FIG. 14).

Figure 5:
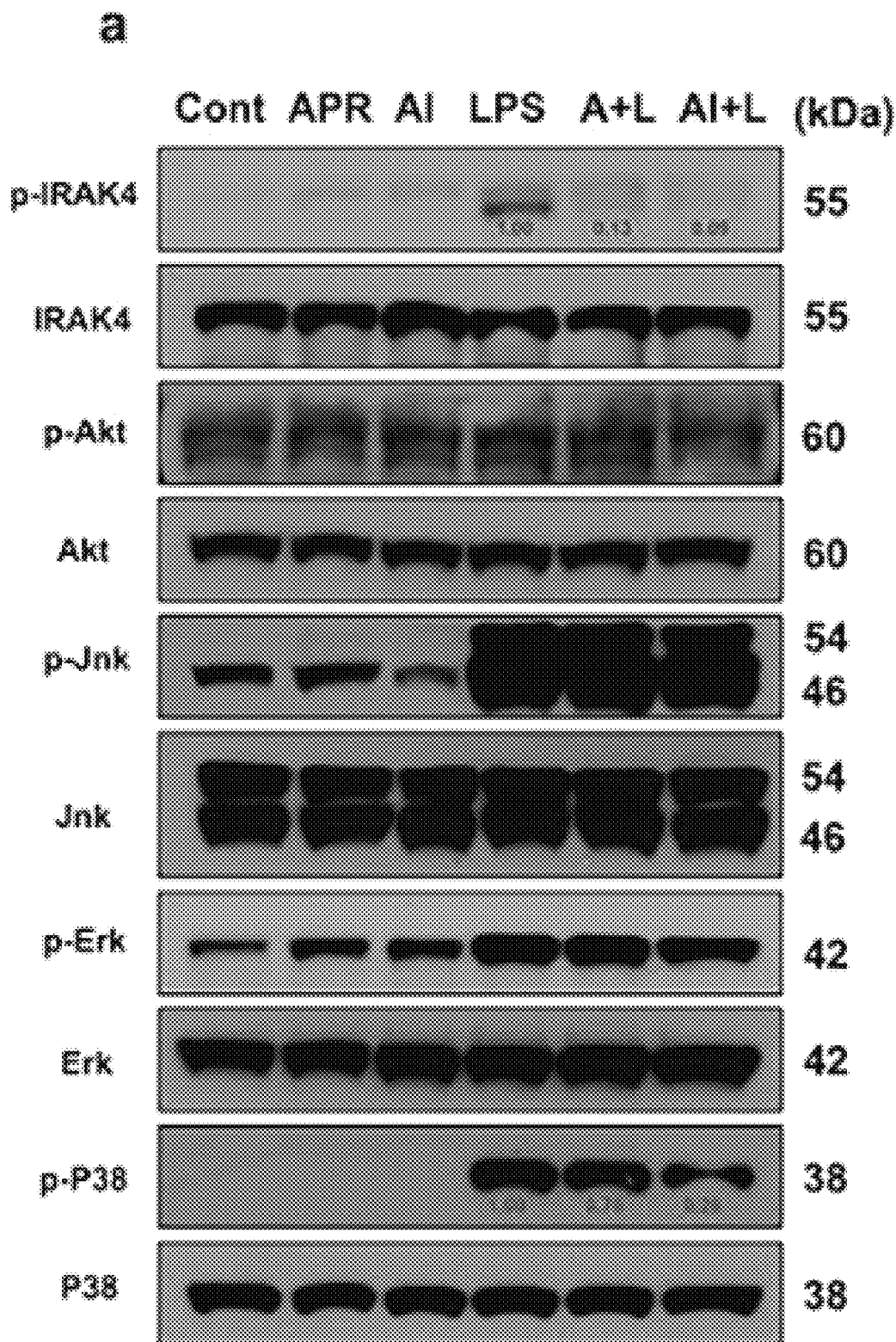
FIG. 5 AdipoAI inhibition of NF-κB and p38 MAPK signaling pathways is dependent of AdipoR1/APPL1 axis in LPS-induced macrophages. (a) Impact of AdipoAI in the phosphorylation of related signaling proteins by western blotting. Raw264.7 cells were pretreated with APR (20 μM) or AdipoAI (5 μM) for 24 h followed by incubation with LPS (100 ng/mL) for an additional 30 min. Representative images are shown, and quantitative analysis of protein expression was performed by densitometric analysis (see lower panel), densitometry values- p-IRAK4:1.00, 0.13, 0.09; p-P38: 1.00, 0.76, 0.26. (b) Expression of p65 protein in cytoplasmic and nuclear extracts of Raw264.7 cells. Representative images of p65 expression are presented along with Lamin B1 and β-actin expression which were used as internal loading controls. Quantitative analysis of protein expression was performed by densitometric analysis (lower panel), Densitometry values- p-P65: 0.53, 1.00, 0.38, 0.76; P65: 0.32, 1.00, 0.21, 0.53. (c) RAW 264.7 cells were transfected with siRNA targeting either AdipoR1, AdipoR2, APPL1, APPL2 or scrambled control siRNA for 24 h, followed by stimulation with AdipoAI or APR for 24 h, then incubation with LPS for additional 6 h. Transfection efficiency of siRNA and mRNA expression levels of IL-6, IL-1β were measured by qPCR and normalized with GAPDH mRNA levels. Data were expressed as the mean±SEM at five biological independent experiments. One-way ANOVA test for multiple-group comparisons, *P<0.05, significant differences between each indicated group. ns, not significant. (d) RAW 264.7 cells were stimulated with LPS, AdipoAI, or APR for different times and proteins levels determined by western blotting. Representative western blotting images are shown along with β-actin used as an internal loading control and densitometric analysis. Densitometry values-Panel 1: APPL1: 1.00, 0.48, 0.44; Panel 2: APPL1: 1.00, 2.17, 5.38; Panel 3: APPL1: 1.00, 2.11, 4.82. (e) Raw264.7 cells were pretreated with APR (20 μM) or AdipoAI (5 μM) for 24 h followed by incubation with LPS (100 ng/mL) for additional 6 h for the measurement of related proteins by WB. Representative images are shown along with β-actin as an internal loading control and densitometric analysis. Densitometry values- APPL1: 1.00, 1.53, 1.58, 0.32, 0.45, 0.67. (f) Raw264.7 cells and (g) BMMs were transfected with siRNA targeting APPL1 or scrambled control siRNA for 24 h, followed by stimulation with AdipoAI for 24 h, then incubation with LPS for additional 6 h for western blotting analysis. Densitometry values for f- APPL1: 1.00, 0.43; p-IRAK4: 1.00, 1.31; p-P-38: 1.00, 1.47. Densitometry values for g- APPL1: 1.00, 0.38; p-IRAK4: 1.00, 1.30; p-P38: 1.00, 1.67. Representative images are shown along with β-actin as an internal loading control, and densitometric analysis. No statistical analysis of western blotting for n=3.
Figure 5:
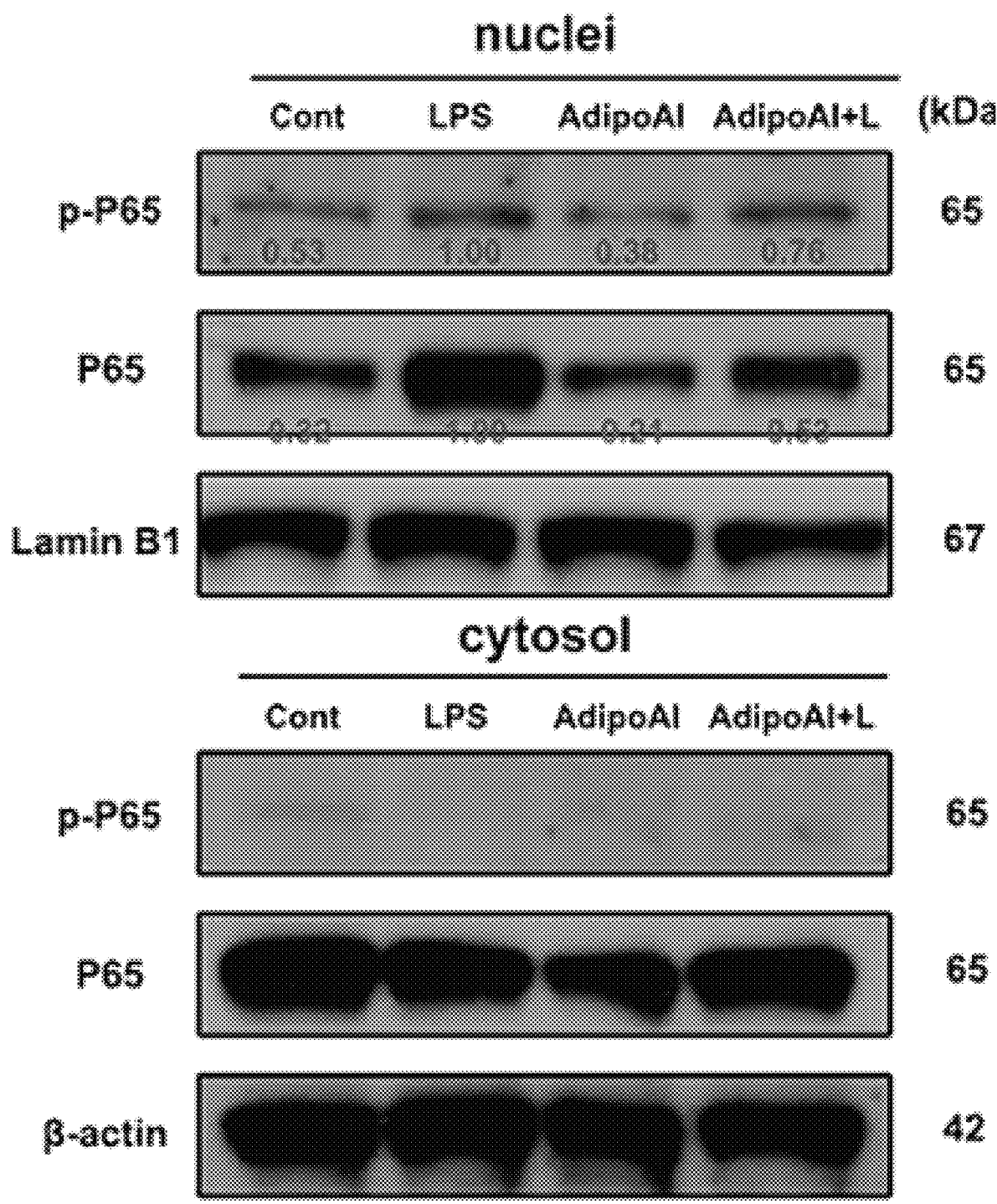
Figure 5:
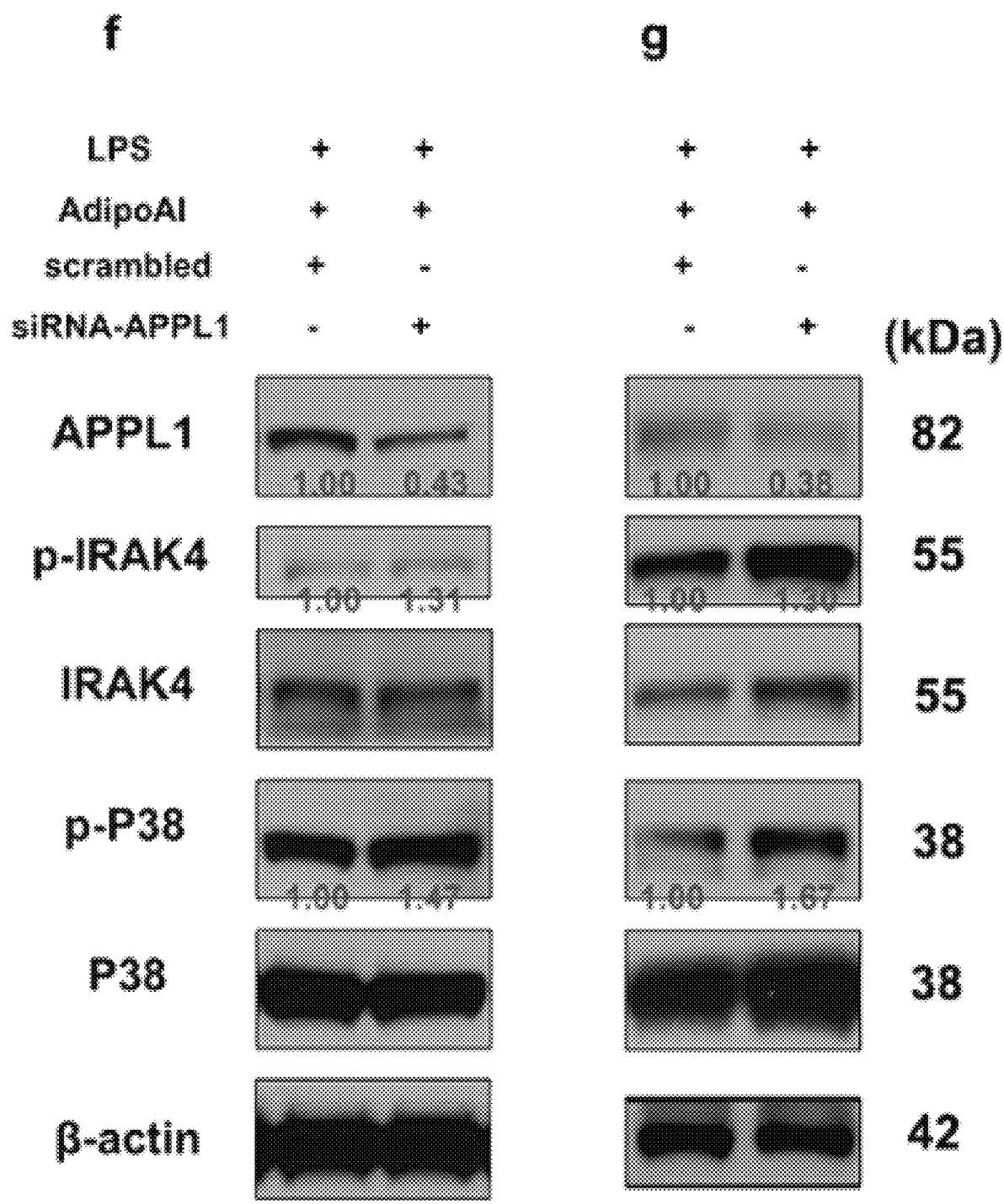
Figure 5:
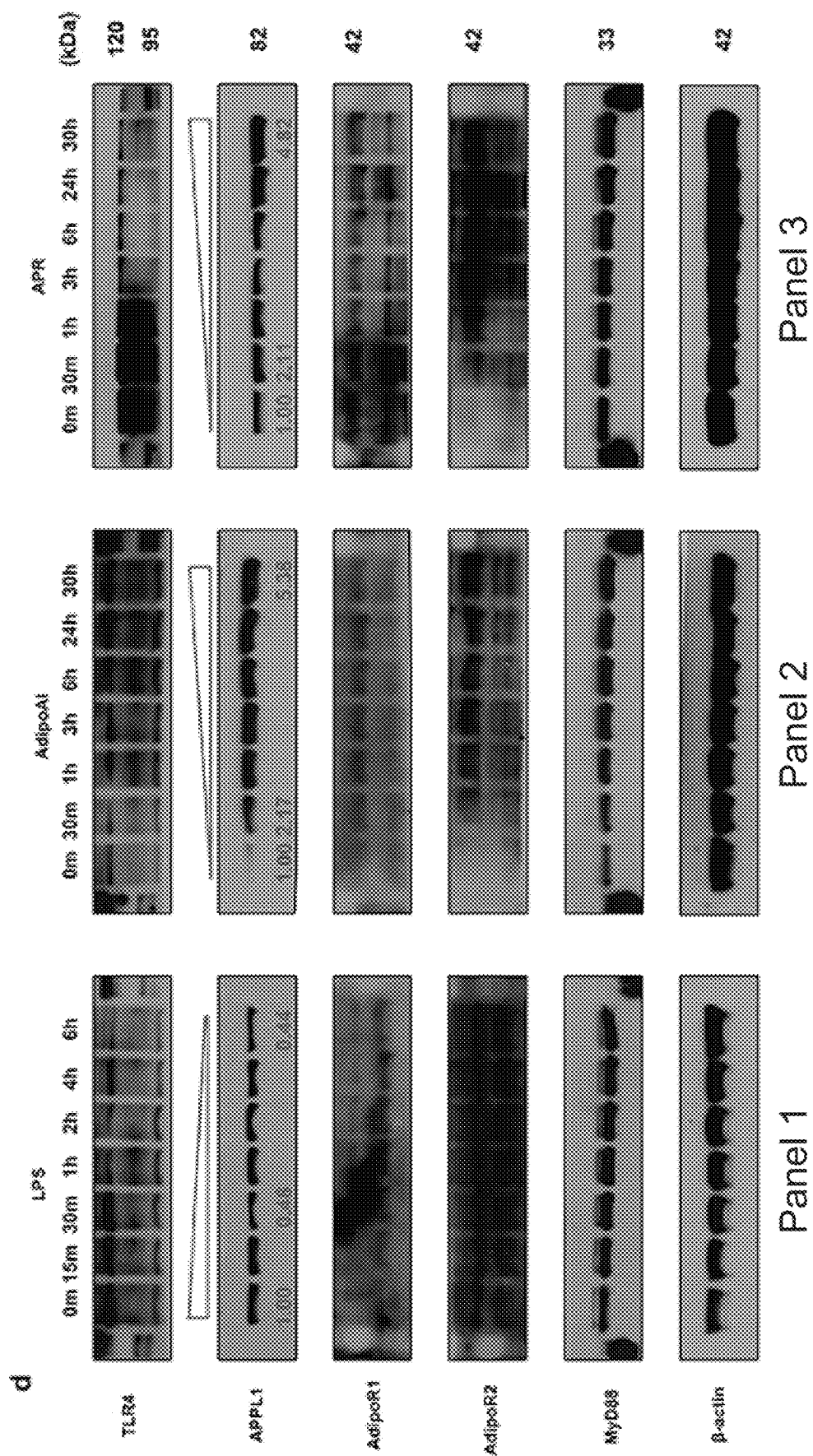
Figure 5:
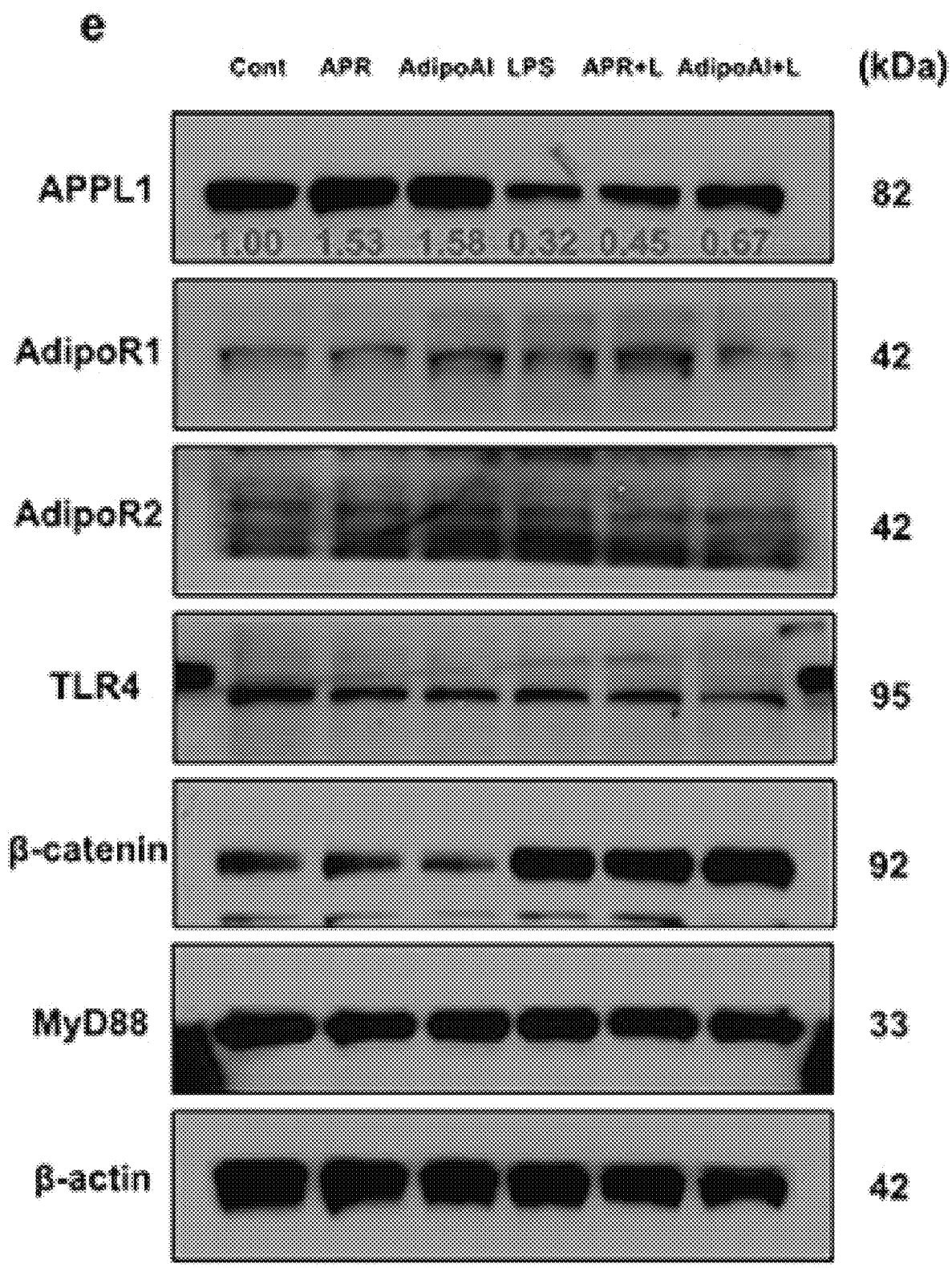
Figure 5:
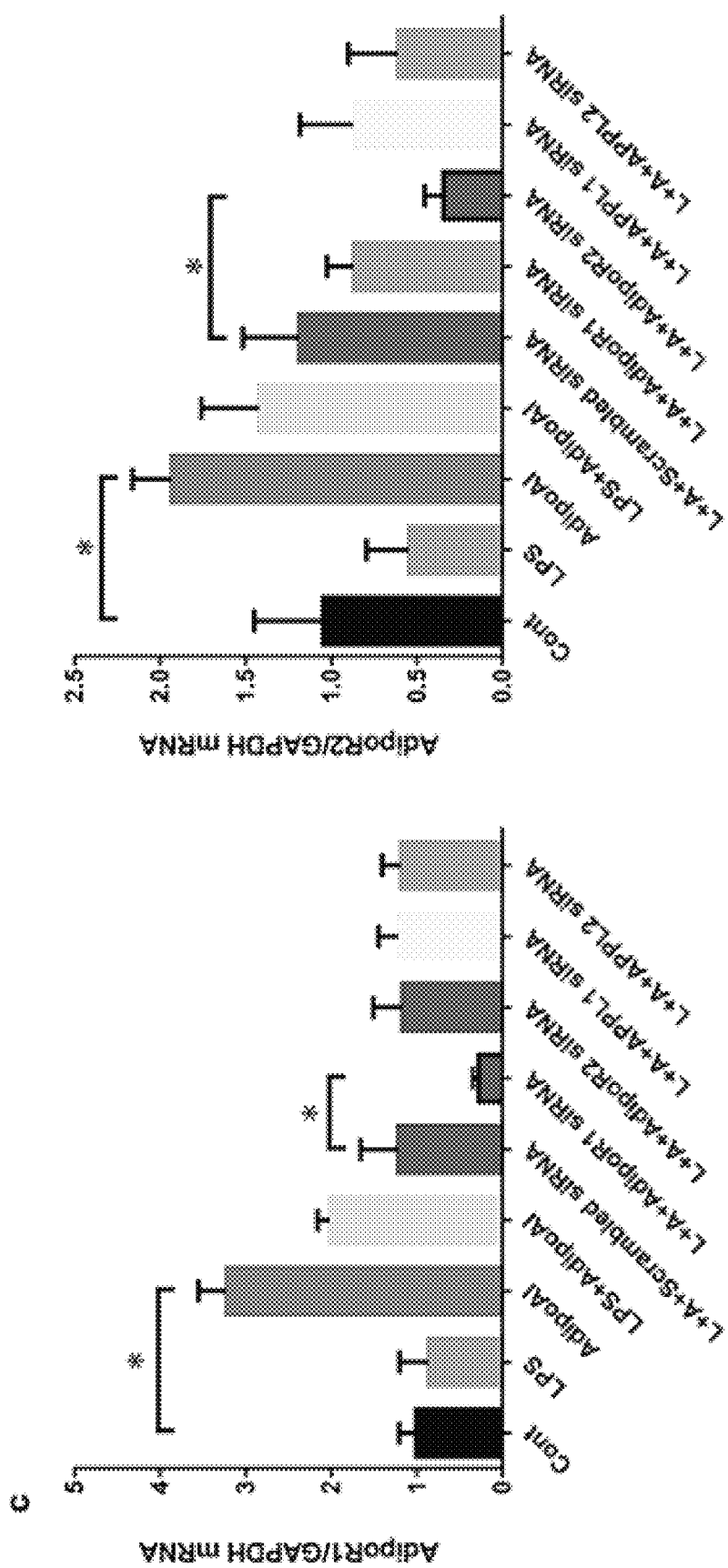
Figure 5:
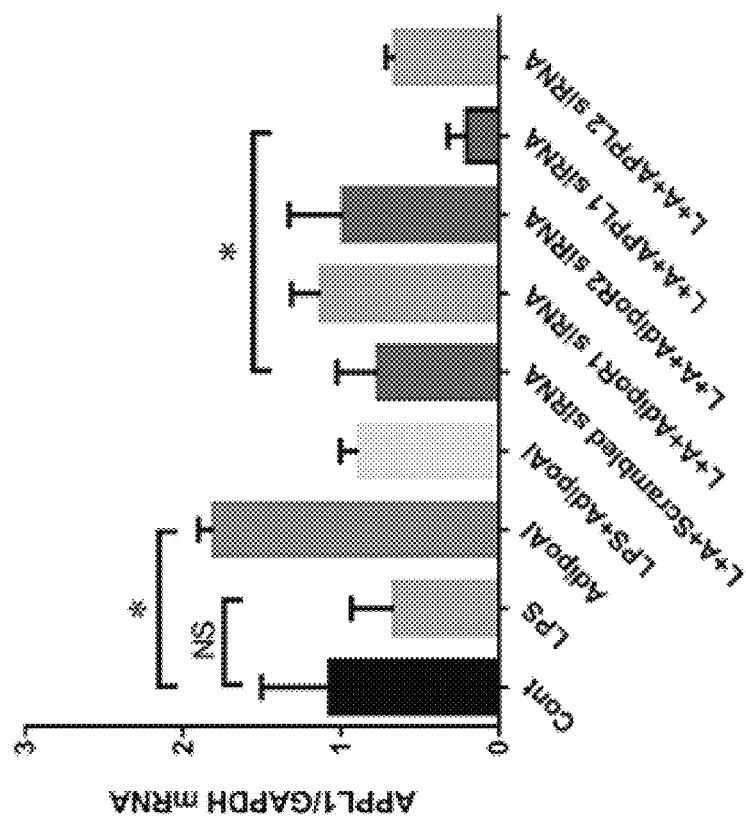
Figure 5:
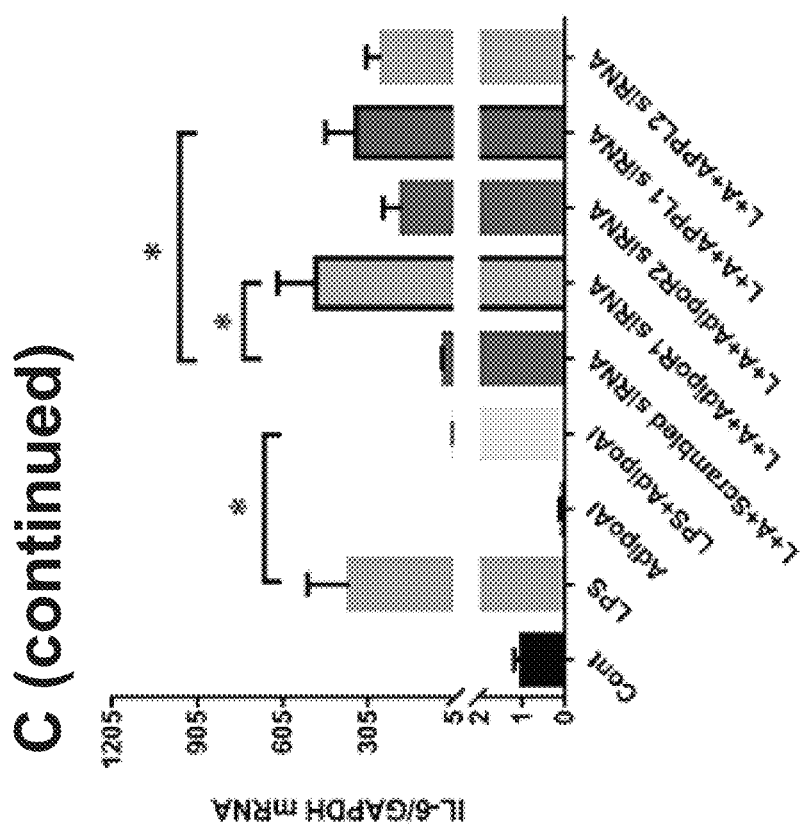
Figure 5:
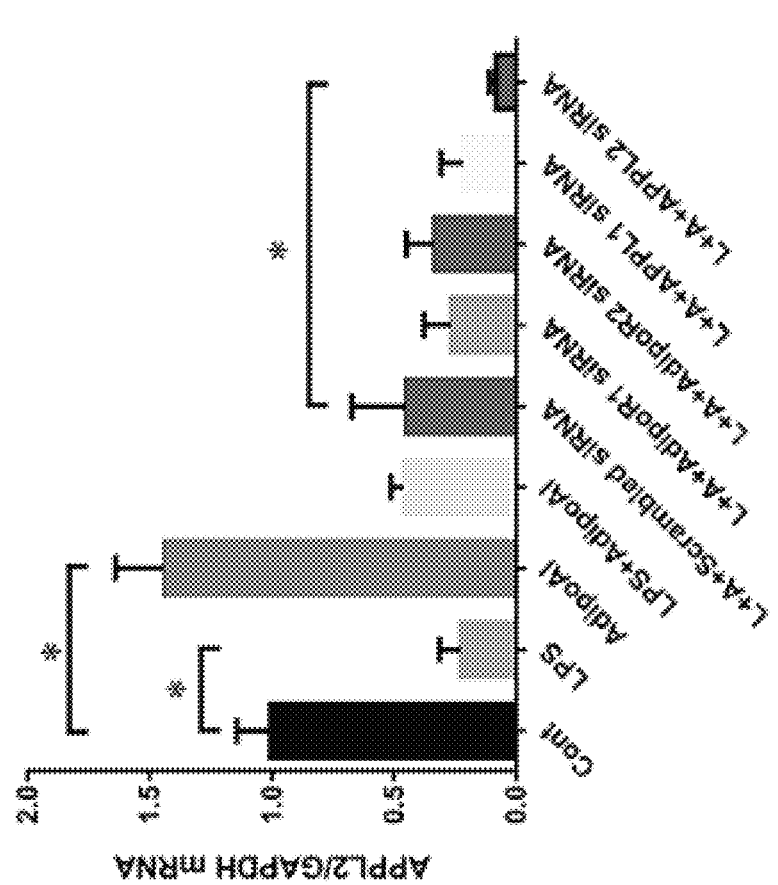
Figure 5:
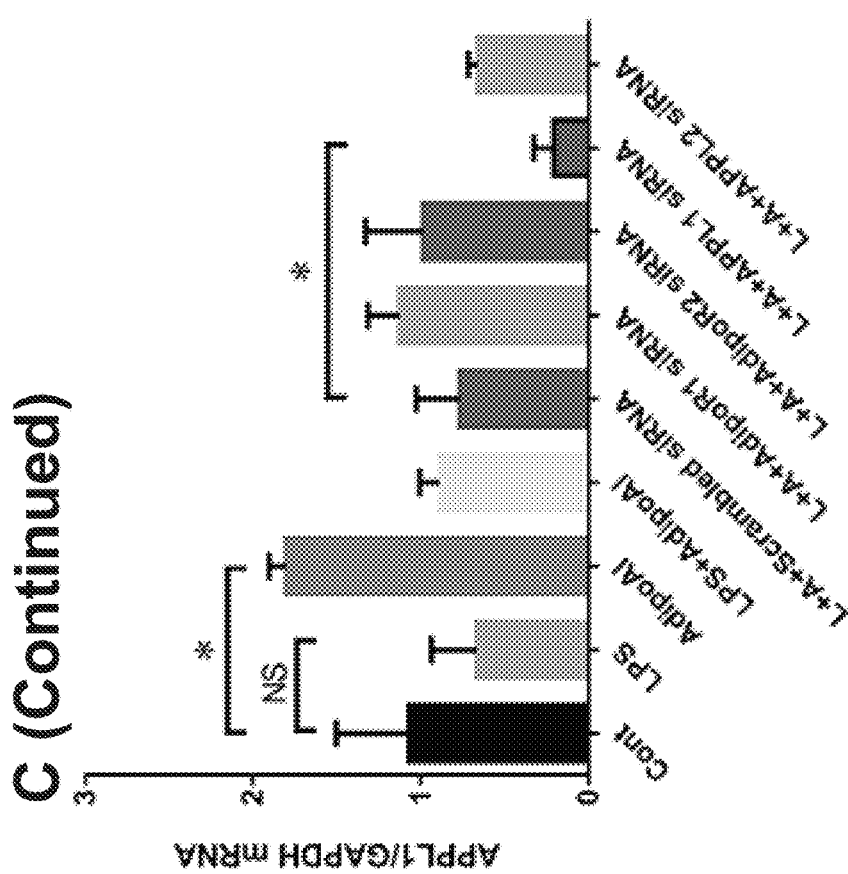
Figure 5:
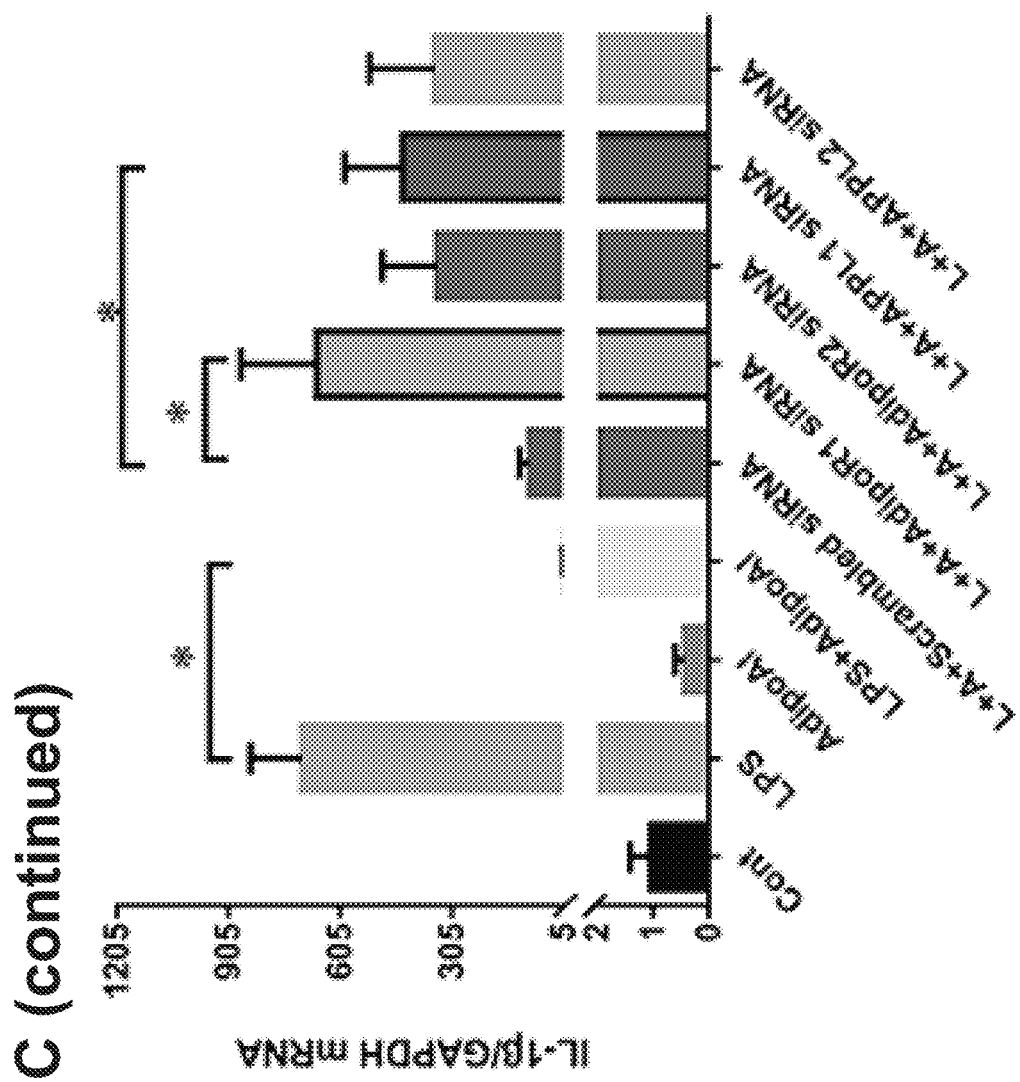
Figure 15:
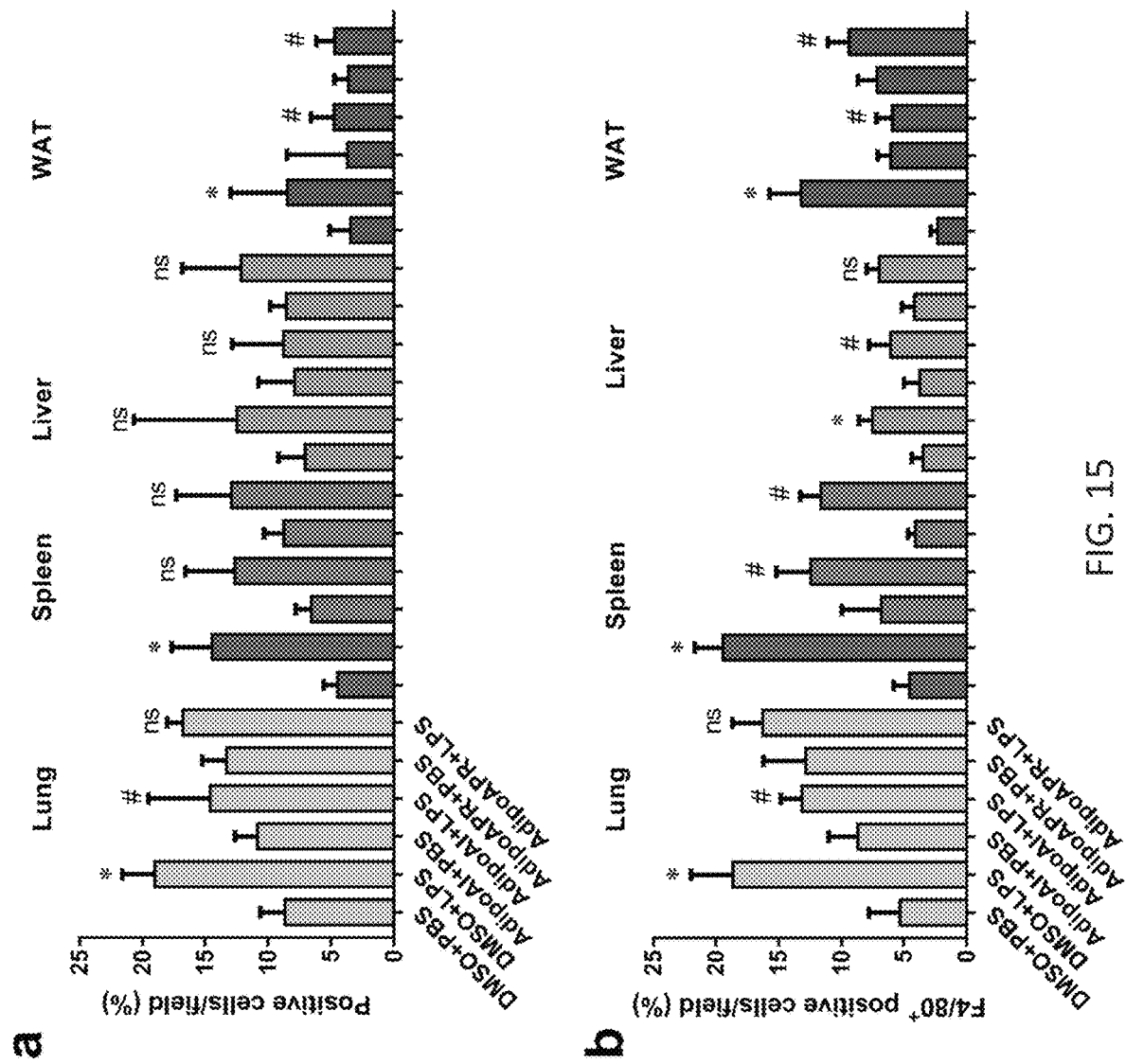
FIG. 15 Quantitative analysis of positive cells of HE staining and F4/80 positive cells in FIG. 4d. Data are expressed as mean±SEM (n=6). One-way ANOVA test for multiple-group comparisons, * vs. DMSO+PBS group, #vs. DMSO+LPS group. */#$P<0.05$, significant differences between each indicated group. ns: not significant.

AdipoAI Inhibits NF-κB and p38 MAPK Signaling Pathways in LPS-Induced Macrophages The potential inhibitory effects of AdipoAI on LPS-induced NF-κB and MAPK signaling pathways in macrophages was investigated. To that end, the phosphorylation of MAPK signaling related protein factors including IRAK4, AKT, JNK, ERK and p38 MAPK in response to LPS in the presence and absence of AdipoAI was evaluated. Whereas treatment of AdipoAI in LPS-induced Raw264.7 cells decreased phosphorylation of IRAK4 and p38 by 70% (FIG. 5a), it did not significantly alter phosphorylation of AKT, JNK or ERK. To assess the effects of AdipoAI on NF-κB signaling, AdipoAI's ability to regulate LPS-induced phosphorylation and nuclear translocation of p65 in Raw264.7 cells was evaluated, and it was found that AdipoAI suppressed LPS-induced p65 phosphorylation and nuclear translocation (FIG. 5b). Quantitative analysis of bands is shown in FIG. 15a, b.

AdipoR1 and APPL1 are Involved in the Anti-Inflammatory Effects of AdipoAI in Macrophages To evaluate whether the anti-inflammatory effects of AdipoAI in macrophages were dependent of AdipoRs and APPLs, Raw264.7 cells stably transfected with AdipoRs and APPLs siRNA or siRNA scrambled control were used to evaluate mRNA levels of IL-6 and IL-1β in response to AdipoAI. Results showed that AdipoAI-mediated inhibition of mRNA expression of proinflammatory cytokines was prevented by AdipoR1 and APPL1 suppression, but not AdipoR2 or APPL2 (FIG. 5c). Moreover, detection of AdipoRs and APPLs protein expression in AdipoAI and LPS treated Raw264.7 cells revealed that AdipoAI increased APPL1 expression, whereas LPS decreased APPL1 (FIG. 5d, e and FIG. 15c, d). Nevertheless, AdipoAI or LPS did not influence AdipoR1 or AdipoR2 protein levels in Raw264.7 cells. To further characterize the requirement of APPL1 for the anti-inflammatory effects of AdipoAI in LPS-induced macrophages, phosphorylation of IRAK4 and p38 MAPK in Raw264.7 cells and BMMs transfected with APPL1 siRNA or scrambled control was assessed. Results demonstrate that AdipoAI and LPS inhibited phosphorylation of IRAK4 and p38 MAPK (FIG. 5f, g and FIG. 15e, f).

Figure 6:
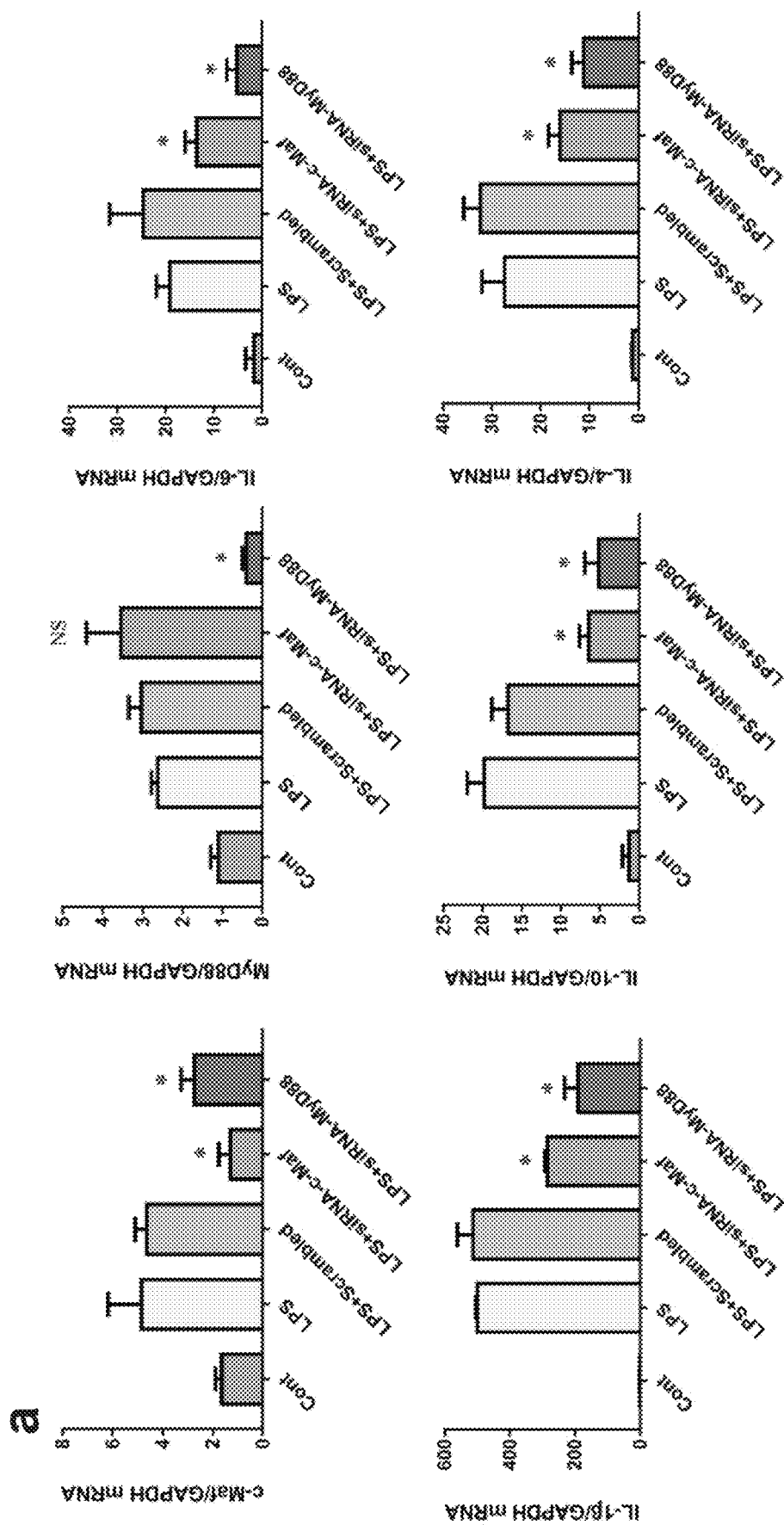
FIG. 6 Involvement of APPL1/MyD88 interaction in the anti-inflammatory effects of AdipoAI in macrophages. (a) RAW 264.7 cells were transfected with siRNA targeting MyD88, c-Maf or scrambled control siRNA for 24 h, followed by stimulation with LPS for 6 h. Transfection efficiency of siRNA and mRNA expression levels of proinflammatory cytokines were measured by qPCR and normalized with GAPDH mRNA levels. Data were expressed as the mean±SEM at five biological independent experiments. One-way ANOVA test for multiple-group comparisons, * vs. LPS+Scrambled group, *P<0.05, significant differences between each indicated group. ns, not significant. (b) Raw264.7 cells were transfected with siRNA targeting MyD88 or scrambled control siRNA for 24 h, followed by stimulation with LPS for 30 min for measurement of related proteins. Representative images are shown along with β-actin as an internal loading control and densitometric analysis. Densitometry values- MyD88: 1.00, 0.24, 1.20, 0.33; pIRAK4: 1.00, 0.00; p-P38: 1.00, 0.11. No statistical analysis of western blotting for n=3. (c) Raw264.7 cells were pretreated with AdipoAI (5 μM) for 24 h followed by incubation with LPS (100 ng/mL) for additional 6 h to analyze interactions of AdipoR1, APPL1 and MyD88 by Co-IP experiments. Proteins immunoprecipitated with the anti-APPL1 antibody were subjected to immunoblotting with antibodies to detect APPL1, AdipoR1 and MyD88. Proteins immunoprecipitated with the anti-MyD88 antibody were analyzed by immunoblotting with antibodies for MyD88, APPL1, and AdipoR1. IB, immunoblotting; IP, immunoprecipitation; Input, whole protein lysis as positive control; IgG: rabbit IgG as negative control.
Figure 6:
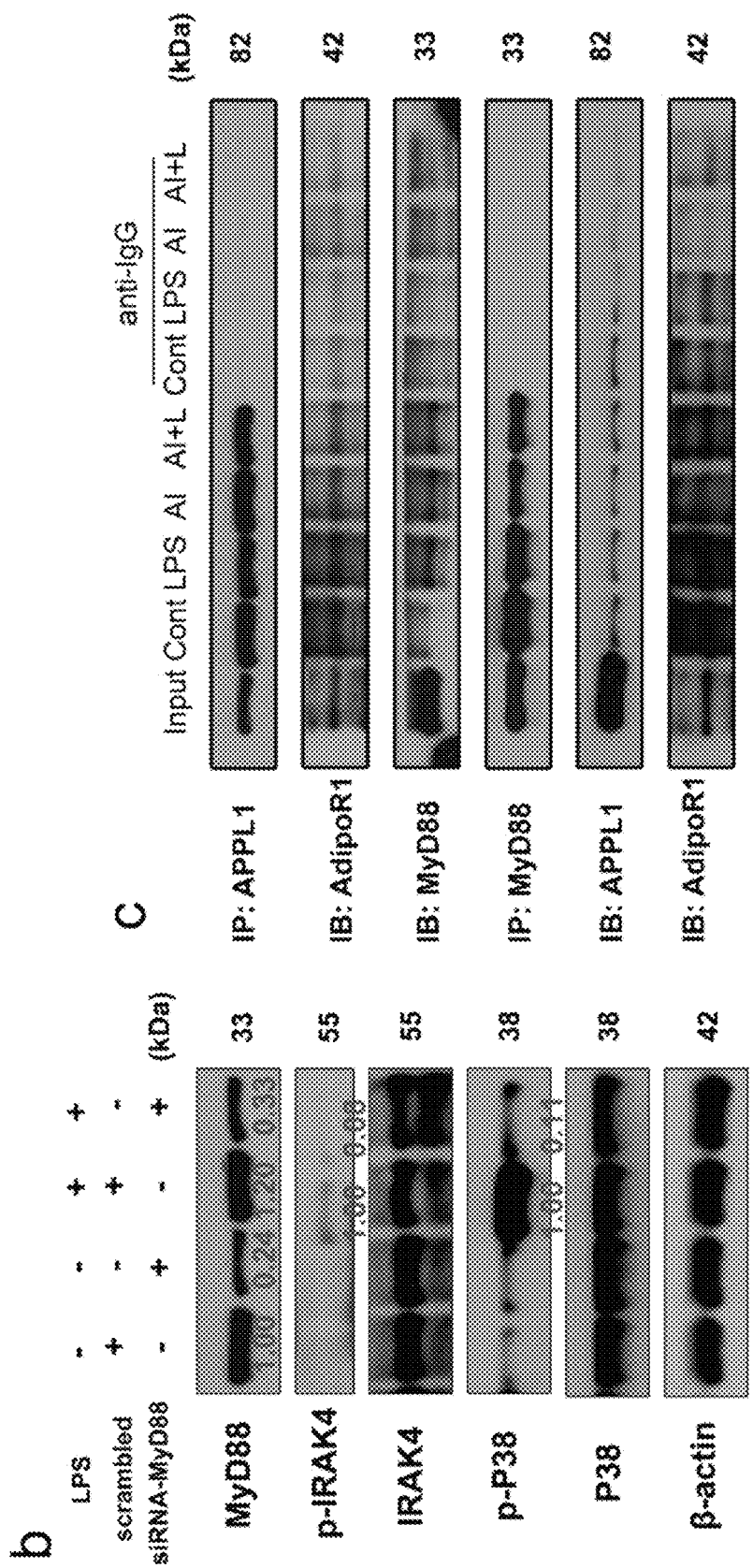

The Anti-Inflammatory Effects of AdipoAI require APPL1/MyD88 Interaction in Macrophages The activated TLR4 signaling by LPS stimulated pro-inflammatory signaling pathways which involve adapter proteins MyD88 and c-Maf. The involvement of MyD88 and c-Maf in LPS-induced macrophage response was investigated. LPS-induced macrophages transfected with c-Maf siRNA or MyD88 siRNA were used to assess the mRNA levels of IL-6, IL-1β, IL-10, and IL-4 (FIG. 6a). Suppressed expression of either c-Maf or MyD88 by specific siRNAs decreased LPS-induced cytokine expression (FIG. 6a) and phosphorylation of IRAK4 and p38 MAPK (FIG. 6b and FIG. 15g) was found. To explore whether the interaction between APPL1 and MyD88 was involved in the AdipoAI suppressed inflammation in LPS-induced macrophages, co-immunoprecipitation studies with protein extracts from control cells were conducted, and cells treated with LPS, AdipoAI or both. APPL1 interacted with AdipoR1 in all groups investigated, and the interaction of APPL1 with MyD88 was increased in AdipoAI and LPS-treated cells as compared to control cells (FIG. 6c). When anti-MyD88 was used as the primary antibody in co-immunoprecipitation studies, similar interactions of APPL1 with AdipoR1 and MyD88 were detected in AdipoAI and LPS-treated cells (FIG. 6c). These data suggest that AdipoR1, APPL1 and MyD88 formed a protein complex which could potentially be critical for the anti-inflammatory effects of AdipoAI in LPS-induced macrophages.

AdipoAI Decreased c-Maf Activation Directly in LPS-Induced Macrophages

Figure 7:
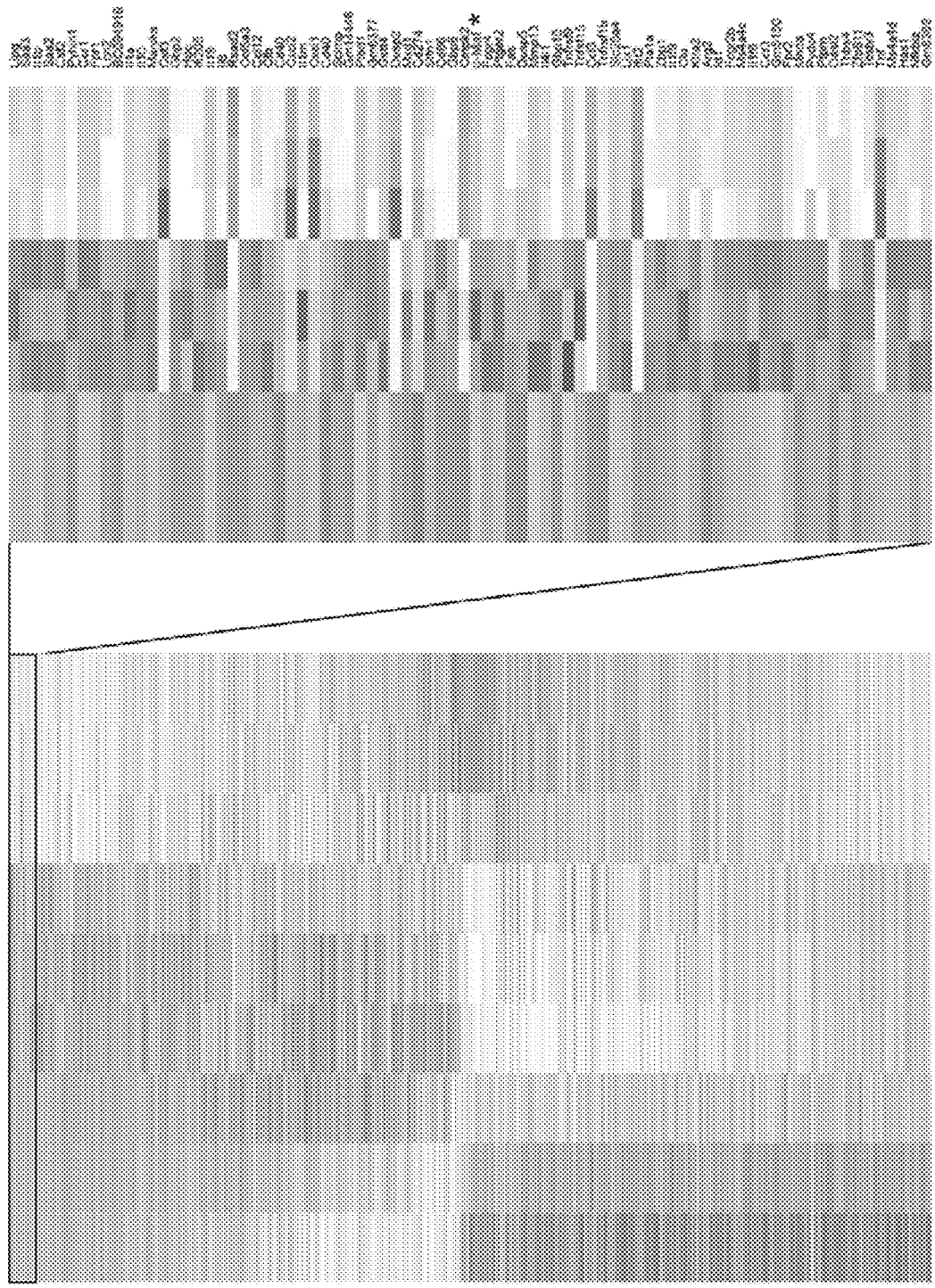
FIG. 7 AdipoAI regulated methylation level of the c-Maf gene promoter to suppress c-Maf activation in LPS-induced macrophages. (a) The cluster heatmap shows mRNAs with expression change of more than 2-fold from microarray data, mRNAs listed from top to bottom are: Lipg, Saa3, Il1b, Saa2, Csf2, Pyhin1, Ccr1, Fpr1, Lcn2, BC094916, Il1a, Il 10, Marcks, Csf3, Gbp2, Hdc, Ifi205, Il19, Il6, Rsad2, Col5a3, Ccl12, Cfb, Cd40, Cxcl2, Il1m, Cxcl1, Cd40, Scimp, Gm14446, Plbd1, Gm6377, Gstt4, Dusp2, Mxd1, Cd274, Slfn1, Cd86, Gbp6, Cmpk2, c-Maf, Fcgr4, Ptger2, Fas, Dusp5, Mmp13, Il4i1, Gbp10, Tnfrsf9, Tnfsf15, Ccl3, Tnfrsf1b, Slc26a4, Lix1, Ifit2, Pla1a, Zbp1, Il1f9, Clu, Klra2, Arg2, Idf, Fcgr2b, Ms4a4c, Il1f6, Ccr3, Gm5150, Fpr2, Mnda, Pydc4, Ptprn, Oasl2, Thbs4, Zfp811, Tcstv3, Tnf, Ms4a4d, Has1, Nfkbiz, Gm8369, asterisk=c-Maf (3 biological replicates/group, $P<0.05$). (b) mRNA levels of c-Maf were determined by qPCR in Raw264.7 cells, BMMs and PEMs treated with AdiopoAI or LPS. Data were expressed as the mean±SEM at five three biological independent experiments. One-way ANOVA test for multiple-group comparisons, * vs. control group, #vs. LPS group. */#$P<0.05$, significant differences between each indicated group. (c) c-MafmRNA expression levels in lung, spleen, liver and WAT of LPS-induced endotoxemia mice were measured by qRT-PCR and normalized with GAPDH mRNA levels. Data are expressed as mean±SEM (n=6). One-way ANOVA test for multiple-group comparisons, * vs. DMSO+PBS group, #vs. DMSO+LPS group. */#$P<0.05$, significant differences between each indicated group. ns, not significant. (d) Immunohistochemical staining for c-Maf in lung, spleen, liver and WAT of APR or AdipoAI treated mice 24 h before LPS challenge (n=6). Red arrow points at c-Maf positive cells.
Figure 7:
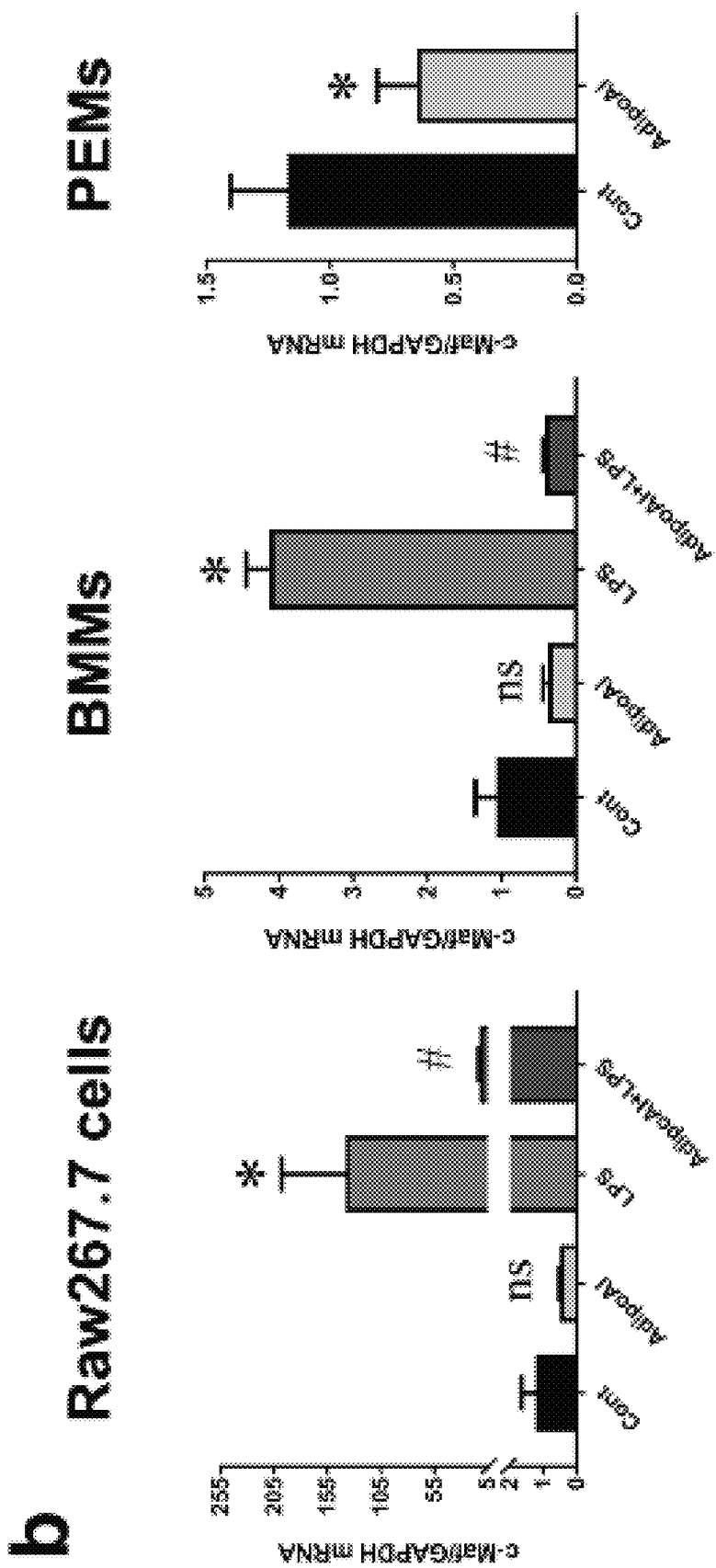
Figure 7:
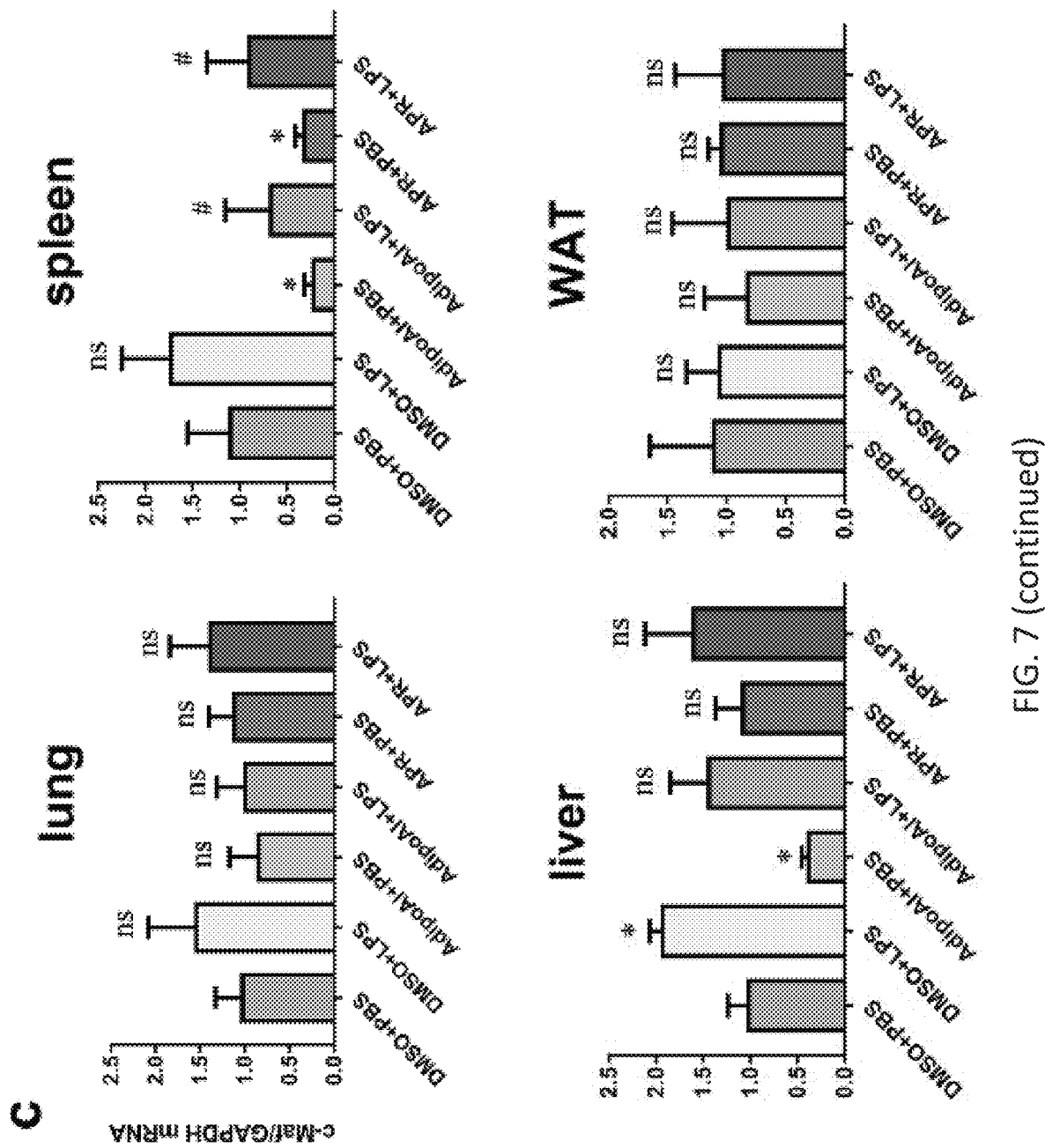
Figure 7:
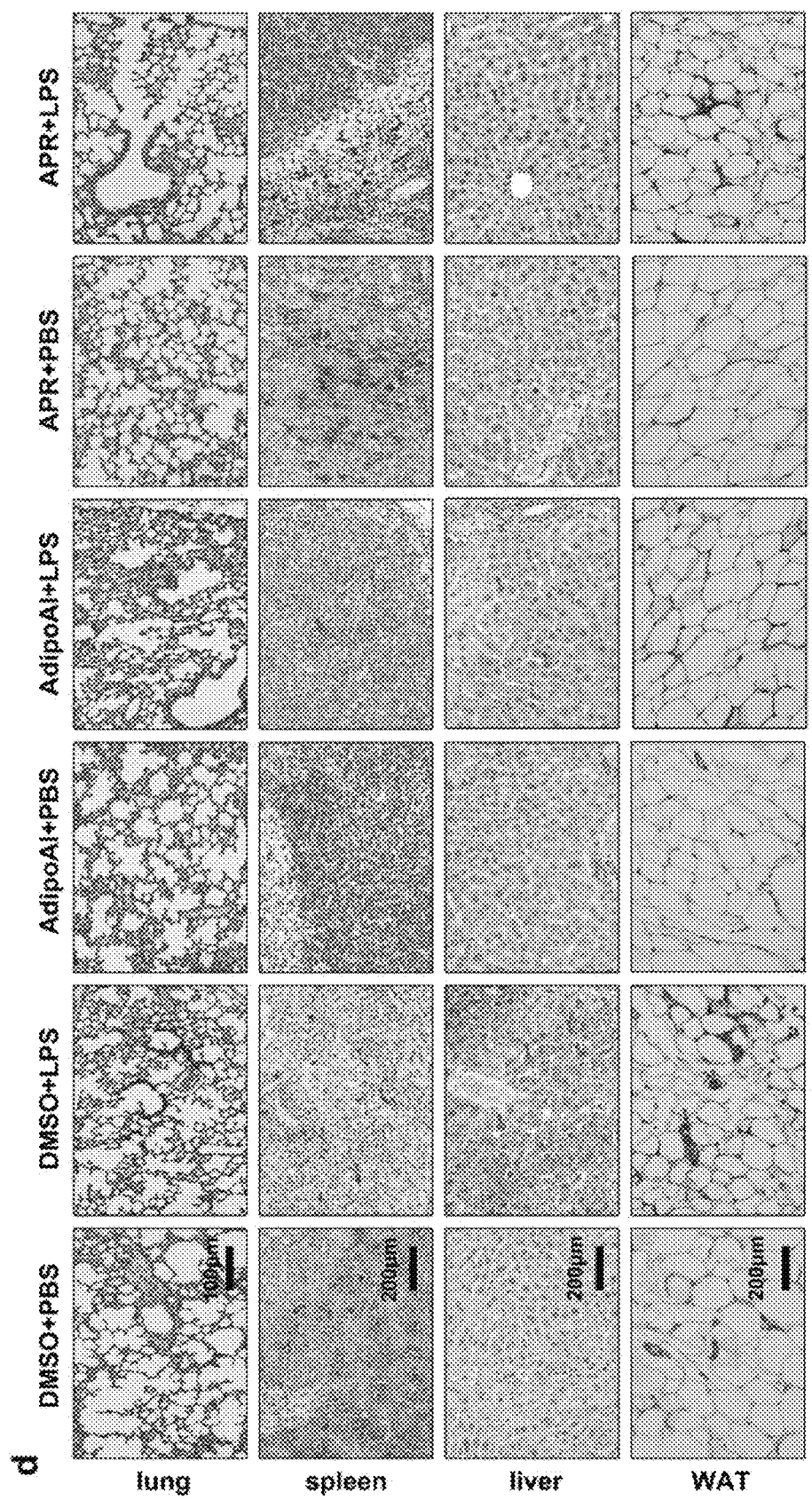
Figure 16:
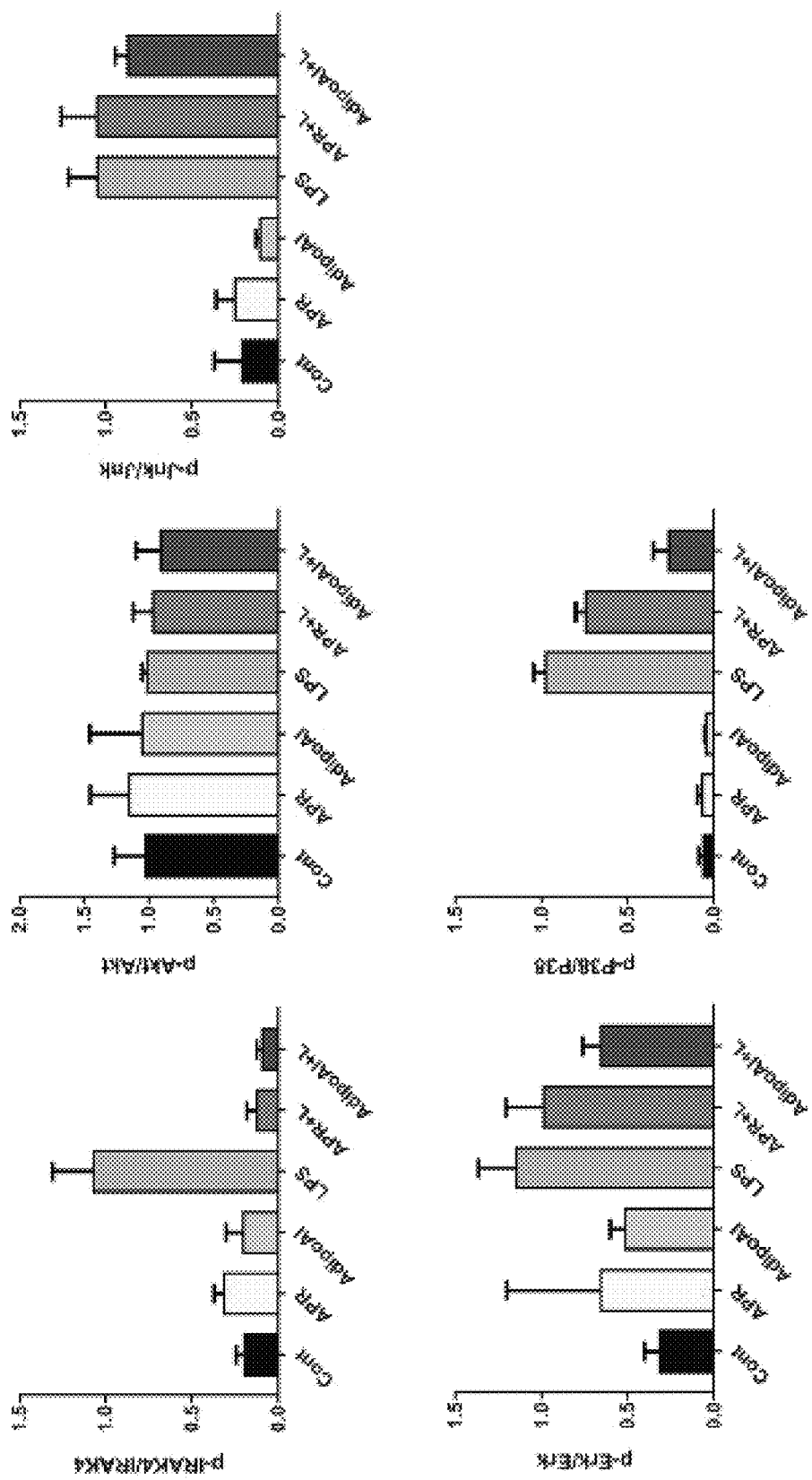
FIG. 16 Quantitative analysis of western blotting. (a) Quantification of bands density of p-IRAK4, p-Akt, p-Jnk, p-Erk and p-p38 in FIG. 5a. (b) Quantification of bands density of p-p65 and p65 distributed in nuclei or cytosol in FIG. 5b. (c) Quantification of bands density of APPL1 in FIG. 5d. (d) Quantification of bands density of APPL1 in FIG. 5e. (e) Quantification of bands density of APPL1, p-IRAK4 and p-p38 in FIG. 5f. (f) Quantification of bands density of APPL1, p-IRAK4 and p-p38 in FIG. 5g. (g) Quantification of bands density of MyD88, p-IRAK4 and p-p38 in FIG. 6b. No statistical analysis of western blotting for n=3.
Figure 16:
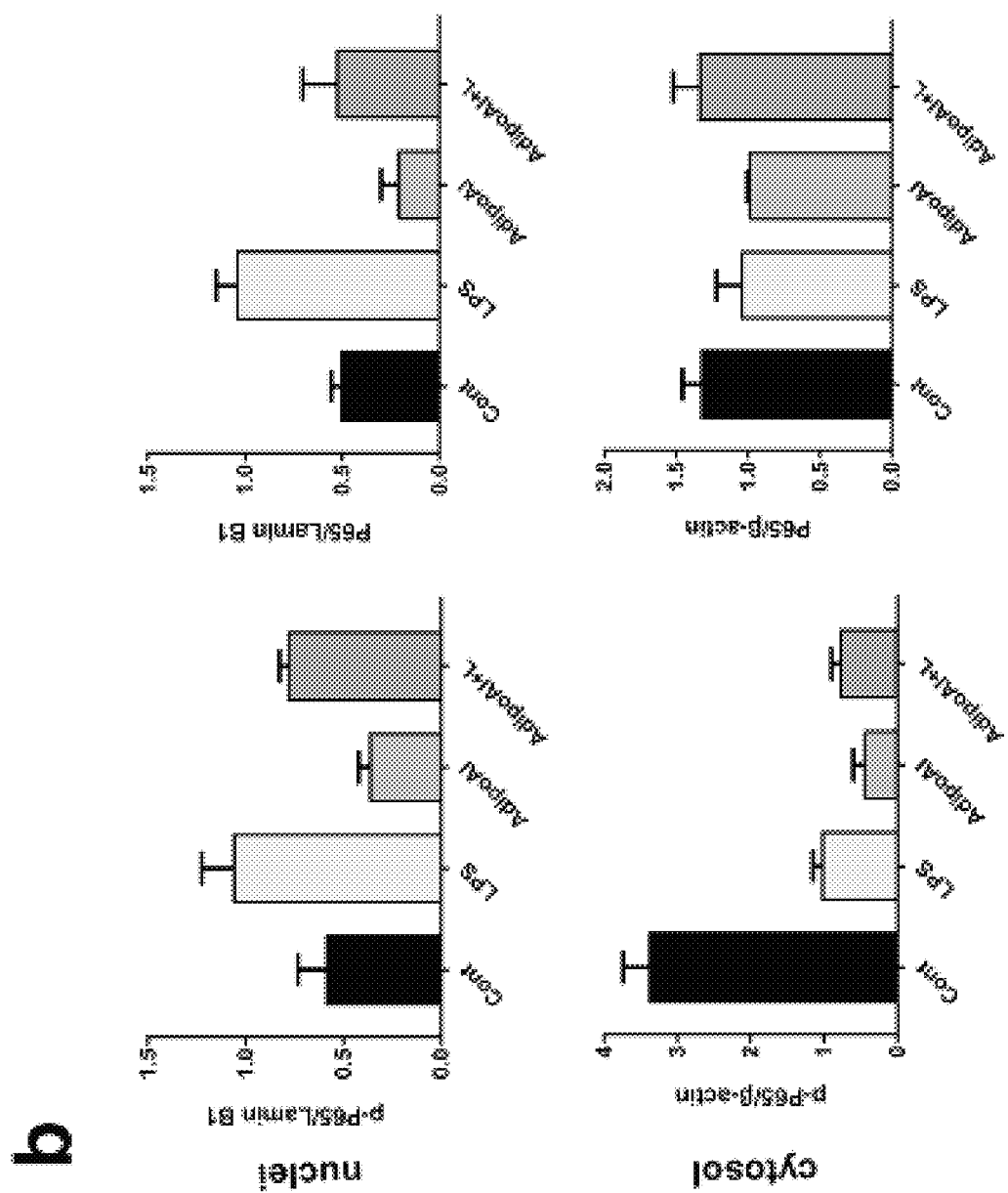
Figure 16:
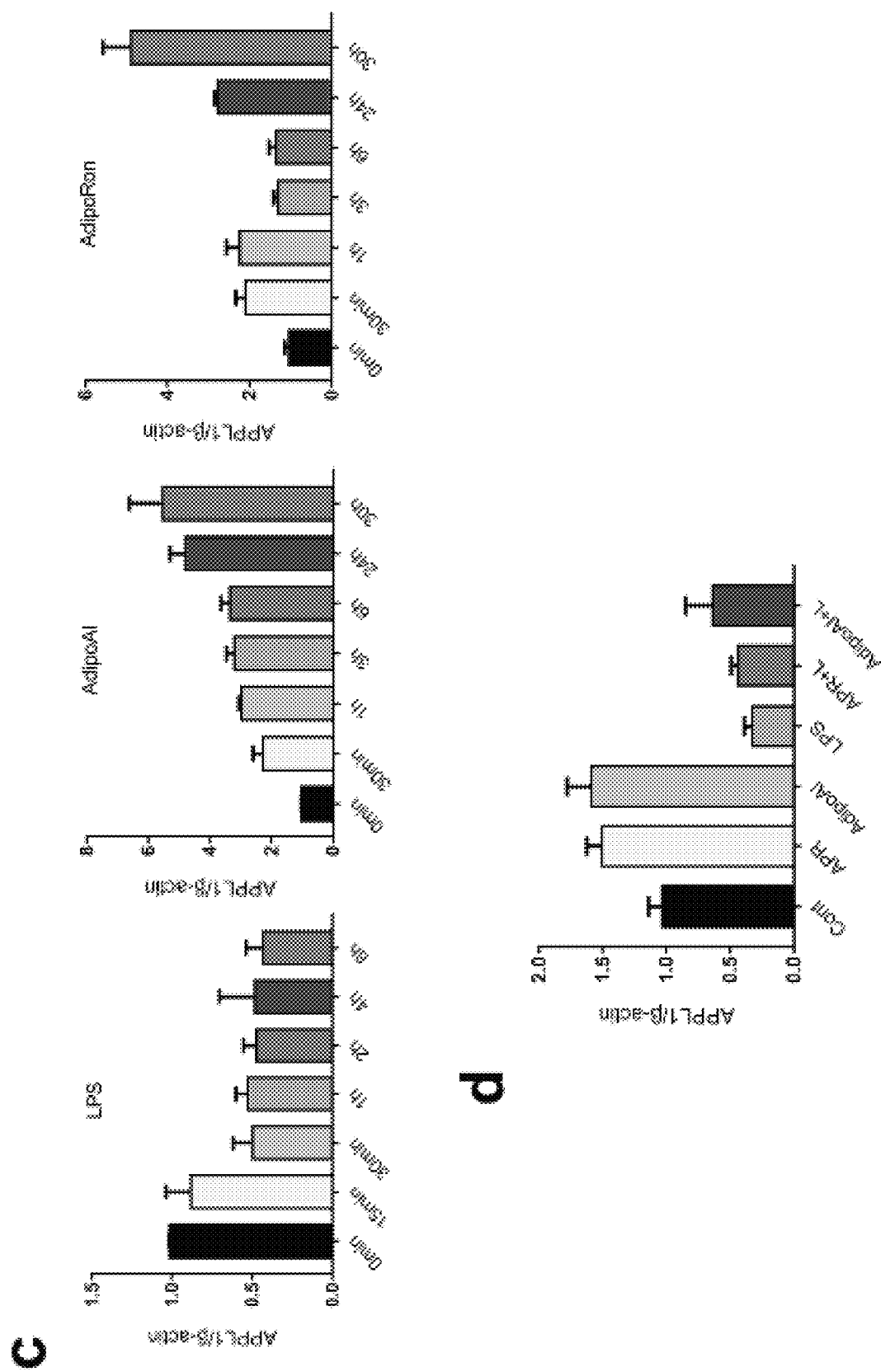
Figure 16:
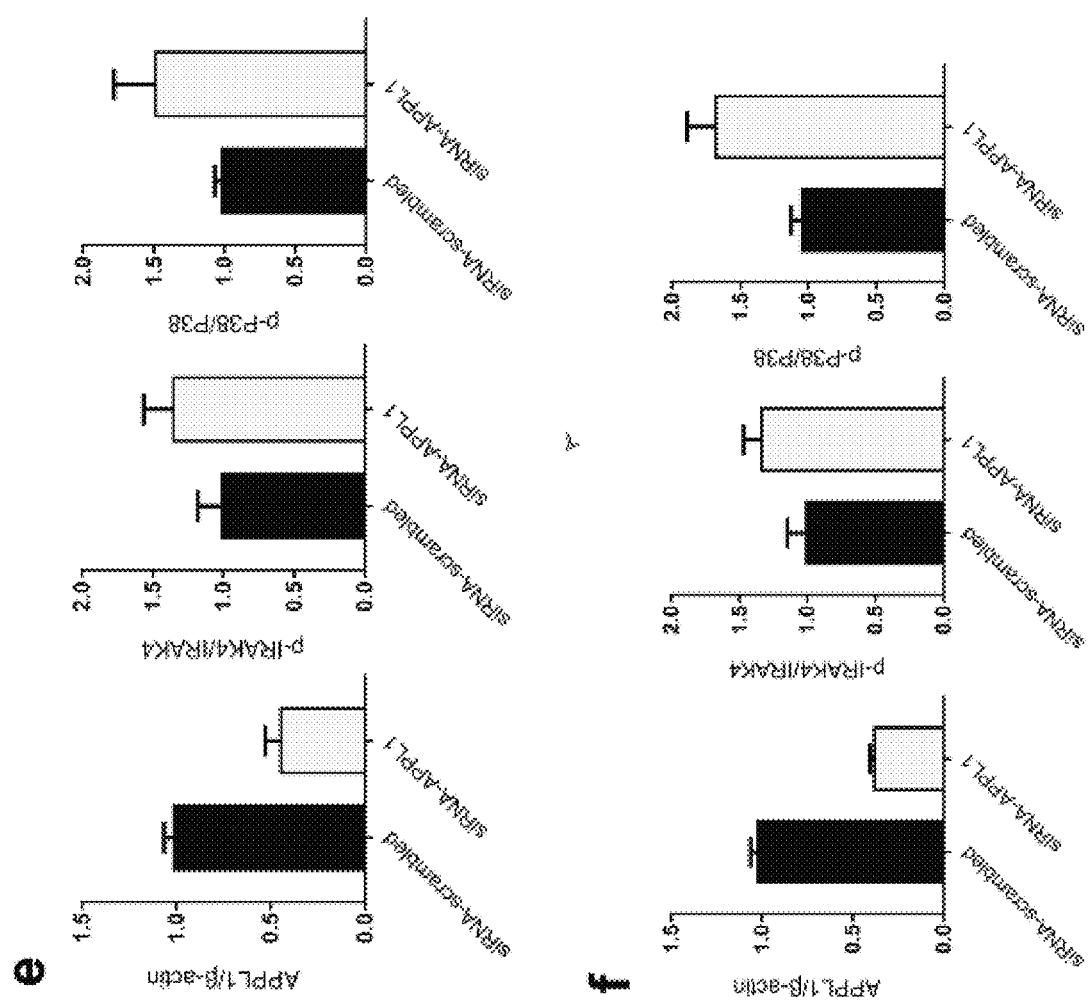
Figure 16:
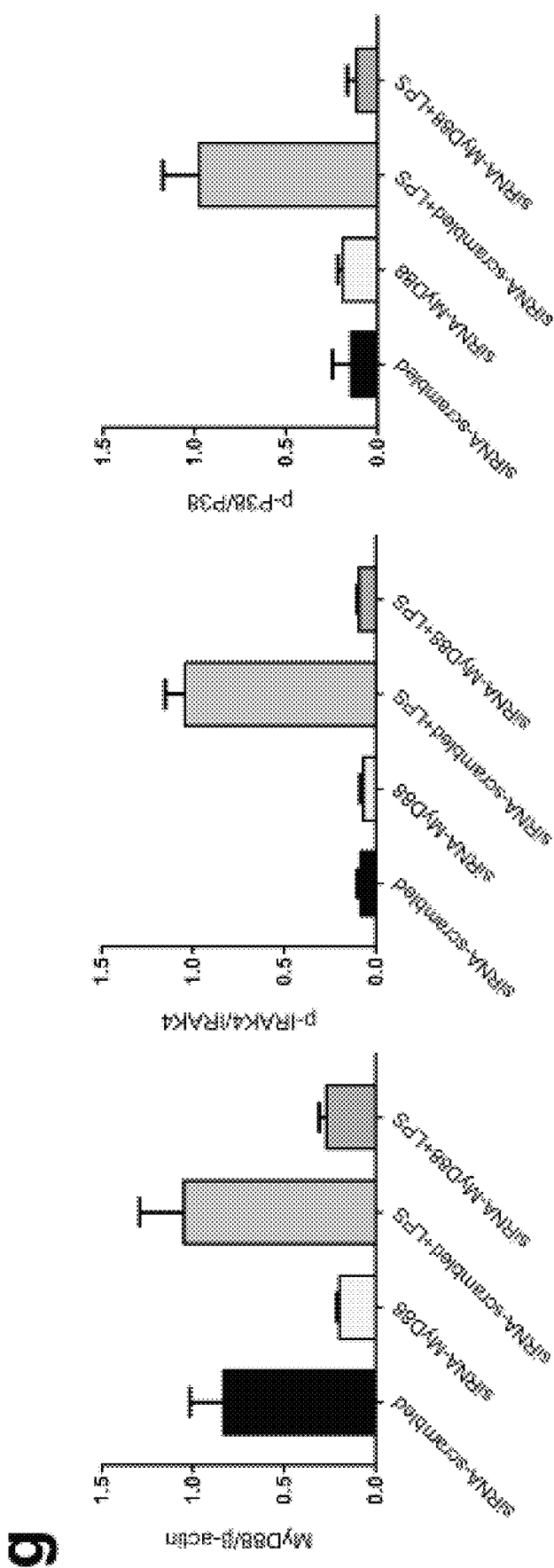
Figure 17:
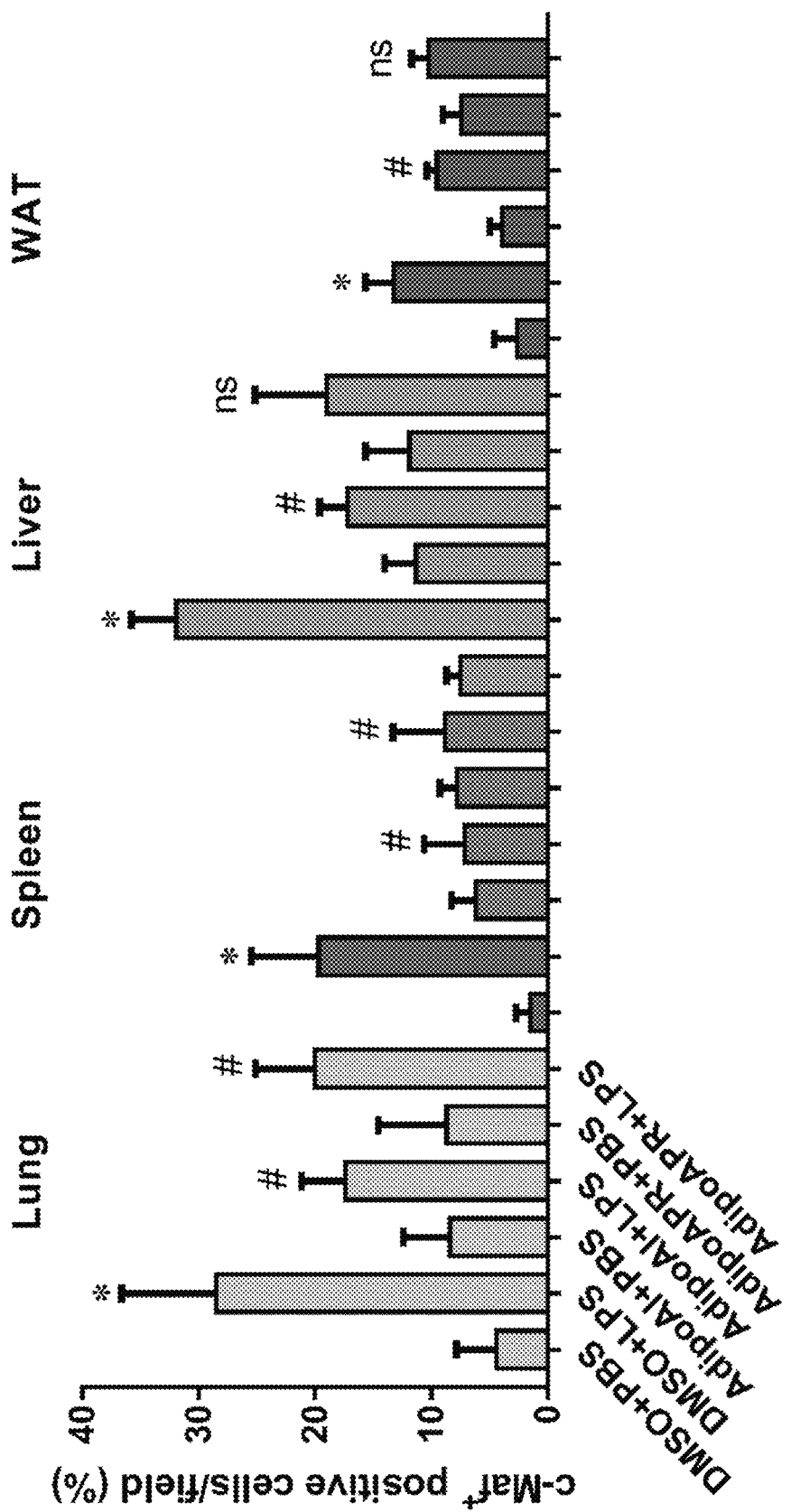
FIG. 17 Quantitative analysis of c-Maf positive cells in FIG. 7d. Data are expressed as mean±SEM (n=6). One-way ANOVA test for multiple-group comparisons, * vs. DMSO+PBS group, #vs. DMSO+LPS group. */#$P<0.05$, significant differences between each indicated group. ns: not significant.

Transcription factor c-Maf is the cellular homolog of the avian viral oncogene v-maf, which belongs to the activator protein 1 (AP-1) superfamily of basic region/leucine zipper factors. It can regulate disease-specific gene networks such as IL-4, IL-7, and IL-10 so that immune responses are elicited in immune cells and macrophages (Cao, Liu, Song, & Ma, 2005; J. I. Kim, Ho Ic Fau-Grusby, Grusby Mj Fau-Glimcher, & Glimcher, 1999; Xie et al., 2016).

mRNA microarray results revealed that c-Maf mRNA levels were induced by LPS treatment and inhibited by AdipoAI in Raw264.7 cells (FIG. 7a). Using qPCR assays it was confirmed the expression pattern of c-Maf as regulated by LPS treatment and/or AdipoAI in Raw264.7 cells, BMMs, and PEMs (FIG. 7b). Additional qPCR and IHC staining experiments with lung, spleen, liver and WAT tissues revealed that c-Maf mRNA and protein levels were induced in LPS-challenged mice but decreased in AdipoAI-treated mice (FIG. 7c, d and FIG. 16).

DISCUSSION

Figure 9:
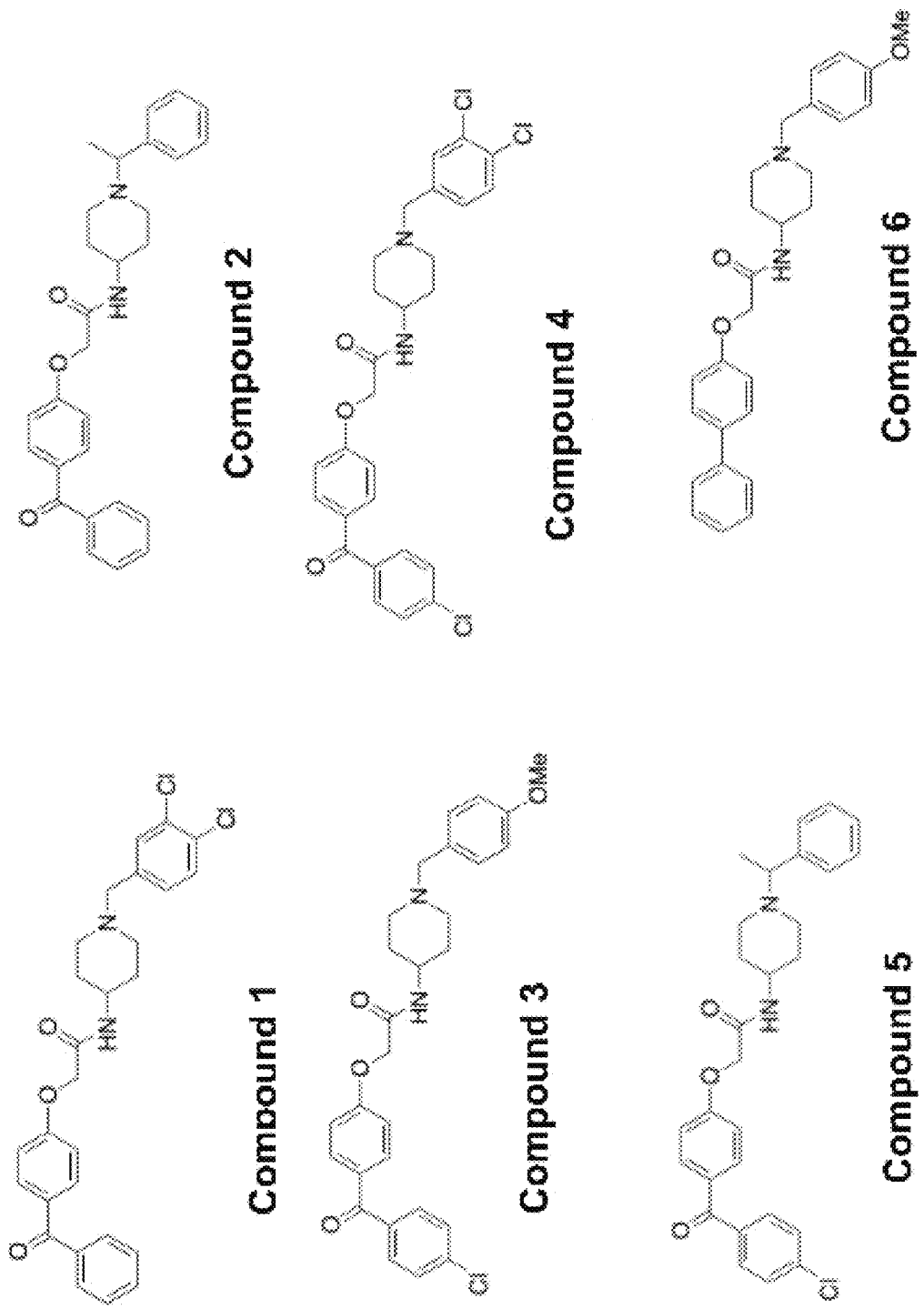
FIG. 9 Chemical structures of 10 small-molecule compounds.
Figure 9:
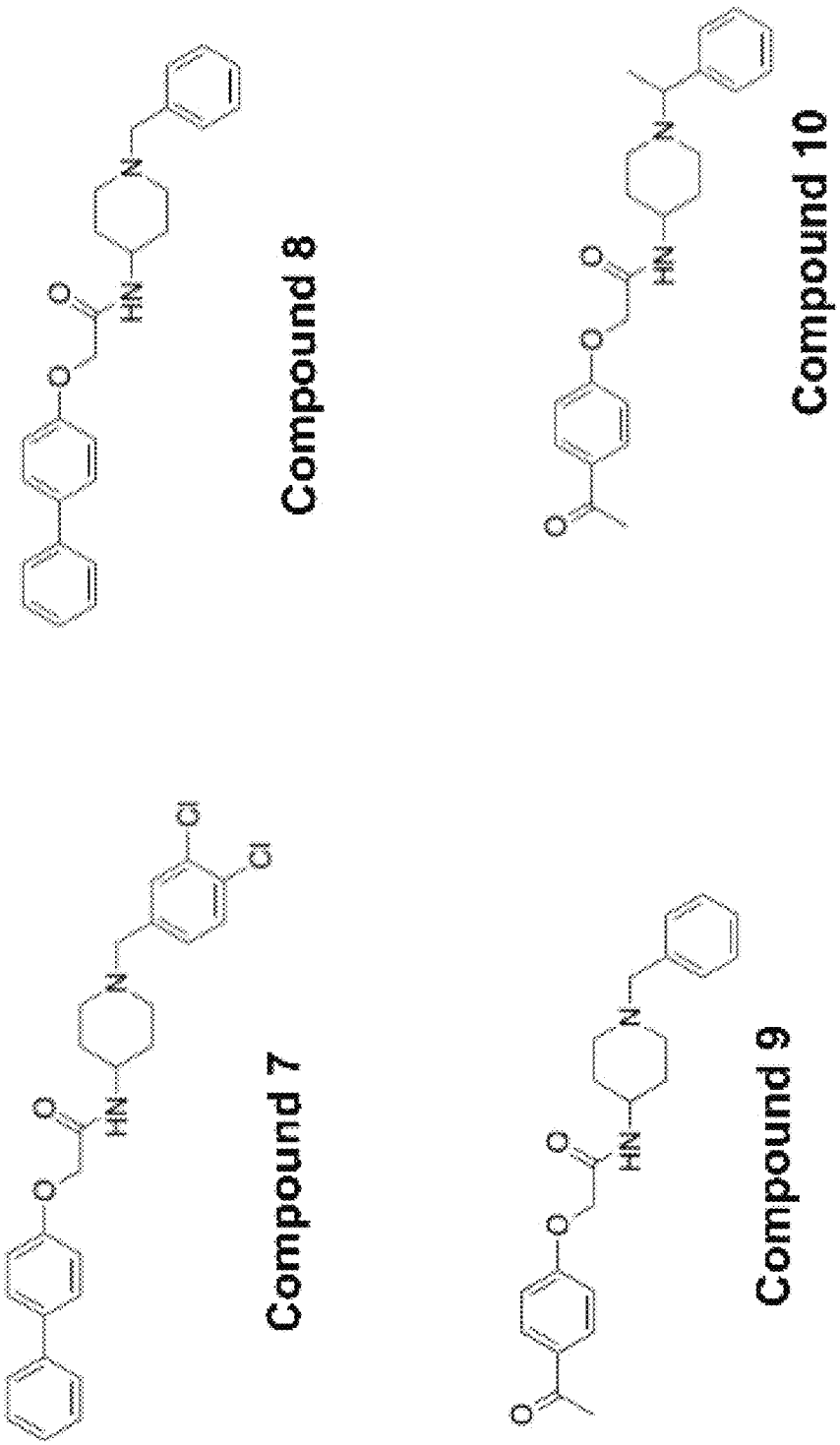
Figure 10:
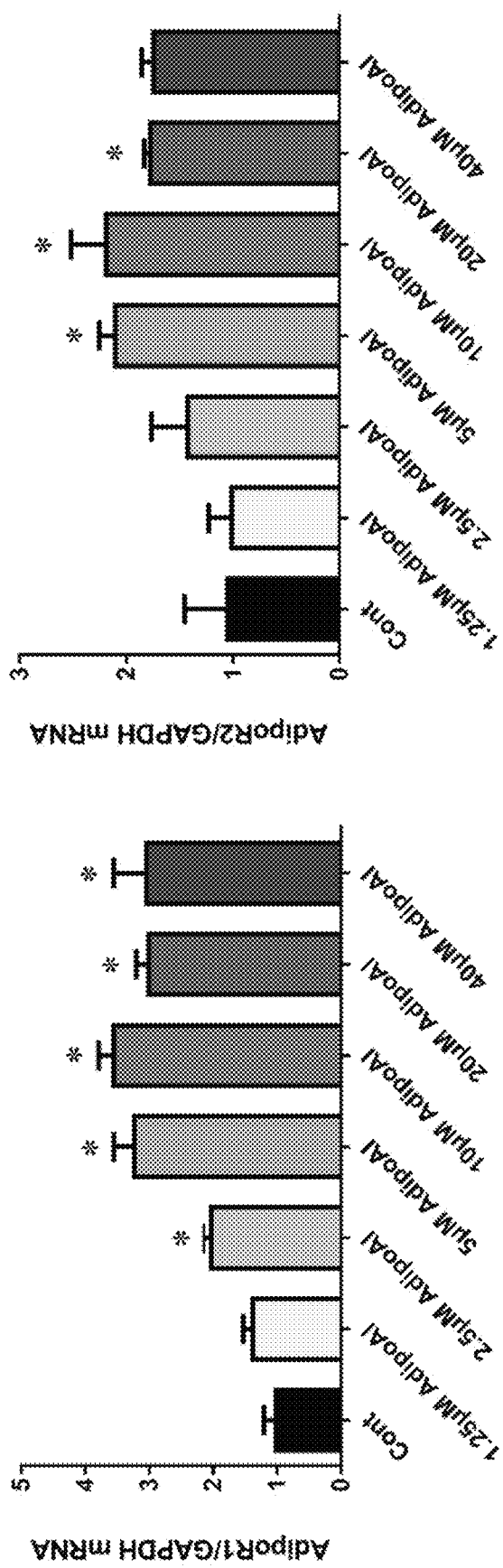
FIG. 10 Raw264.7 cells were treated with different doses of AdipoAI for 24 h to measure AdipoR1/2 mRNA expression by qRT-PCR. Data were expressed as the mean±SEM at five biological independent experiments. One-way ANOVA test for multiple-group comparisons, * vs. control group. * $P<0.05$, significant differences between each indicated group.

APN has been reported to exhibit potent anti-inflammatory properties in vitro and in vivo (Nicolas et al., 2018). Thus, APN treatment can inhibit LPS-induced expression of pro-inflammatory cytokines in macrophages from various sources (Wulster-Radcliffe, Ajuwon, Wang, Christian, & Spurlock, 2004; Yamaguchi et al., 2005; Yokota et al., 2000) and suppress bone marrow inflammation, thereby enhancing the antibacterial activity of hematopoietic cells (Masamoto et al., 2016). Despite the therapeutic potential of APN as an anti-inflammatory and antidiabetic agent, there are potential challenges of using APN in the clinic for the treatment of inflammation and various metabolic diseases, including the high possibility of adverse immunoreactions, the need for constant intravenous (i.v.) injection of high doses of APN to mediate therapeutic effects, and the difficulty and cost of producing APN protein in large quantities (Wu et al., 2019). AdipoR agonists (FIG. 1a, FIG. 9) were designed and experimental evidence is presented that AdipoAI (compound 3) exhibited the most potent anti-inflammatory ability (FIG. 1, 2) and increased the mRNA levels of AdipoRs (FIG. 10) in LPS-induced Raw264.7 cells, LPS-induced BMMs, and murine PEMs. Notably, the anti-inflammatory efficacy of AdipoAI was estimated to be about 8 times higher than that of APR in macrophages.

Figure 11:
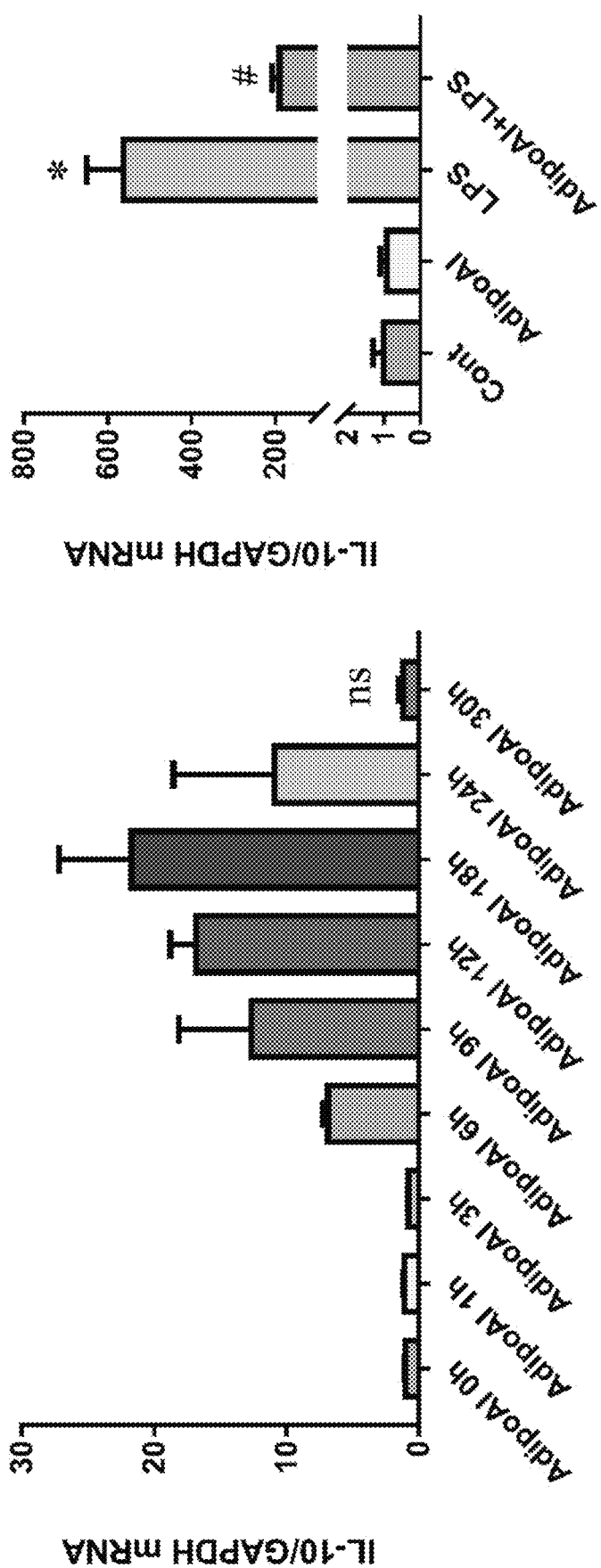
FIG. 11 AdipoAI suppresses LPS-stimulated IL-10 in Raw264.7 cells. (Left panel) Raw264.7 cells were pretreated with AdipoAI (5 μM) for different times and IL-10 mRNA expression level measured by qRT-PCR and normalized with GAPDH mRNA levels. (Right panel) Raw264.7 cells were pretreated with AdipoAI (5 μM) for 24 h followed by incubation with LPS (100 ng/mL) for additional 6 h for measurement of IL-10 mRNA expression level by qRT-PCR and normalized with GAPDH mRNA levels. Data were expressed as the mean±SEM at five biological independent experiments. One-way ANOVA test for multiple-group comparisons, * vs. control group, #vs. LPS group. */#$P<0.05$, significant differences between each indicated group. ns, not significant.

AdipoAI and APR inhibited expression of proinflammatory cytokines such as IL-6 and IL-1β, but also downregulated expression of the anti-inflammatory cytokine IL-10 in LPS-induced macrophages. IL-10 expression was stimulated in macrophages by full-length APN to mediate the anti-inflammatory response (Kumada et al., 2004; Wolf, Wolf, Rumpold, Enrich, & Tilg, 2004). In a different report, APN inhibited pro-inflammatory signaling in human macrophages in an IL-10-independent fashion (Folco et al., 2009). Treatment of microphages with AdipoAI or APR for 18 h or less increased IL-10 mRNA expression, but longer treatments resulted in decreased IL-10 expression (FIG. 11). As a pro-inflammatory factor similar to IL-6 and IL-1β, the mRNA level of TNF-α in macrophages treated with AdipoAI or APR was also examined by qRT-PCR and mRNA array analysis. However, the result showed that AdipoAI pretreatment did not inhibit TNF-α expression levels in LPS-induced Raw264.7 macrophage, BMMs or PEMs (data not shown). It was found that AdipoAI did not inhibit the expression of TNF-α in white adipose tissue, spleen, or bone marrow of DIO mice (FIGS. 3a, b, and c) or LPS-induced endotoxemia mice (FIG. 4a). In addition to the different types of macrophages and the treatment time and ways the molecules were used by various laboratories, the complex synthetic and production pathways and metabolic mechanisms of TNF-α are all potential reasons for the different actions in different studies.

Macrophage activation presents two extremes of dynamic changing states that can be represented by classical M1 macrophages induced by LPS and alternative M2 macrophages induced by IL-4. M1-M2 polarization of macrophages is a tightly controlled process that entails a series of signaling pathways, transcriptional, and posttranscriptional regulatory networks (Murray et al., 2014; Wang, Liang, & Zen, 2014). Several recent studies analyzing the effect of APN on the expression of a limited number of macrophage polarization markers concluded that APN promoted the M2 phenotype in mouse peritoneal macrophages, RAW264.7 cells, and rat Kupffer cells (Lovren et al., 2010; Mandal et al., 2011; Ohashi et al., 2010). A comprehensive analysis of the relationship between AdipoAI-induced transcriptome and Raw264.7 macrophage polarization was conducted, revealing that AdipoAI could not significantly change the expression of M1 phenotype or M2 phenotype markers (FIG. 2h).

Figure 3:
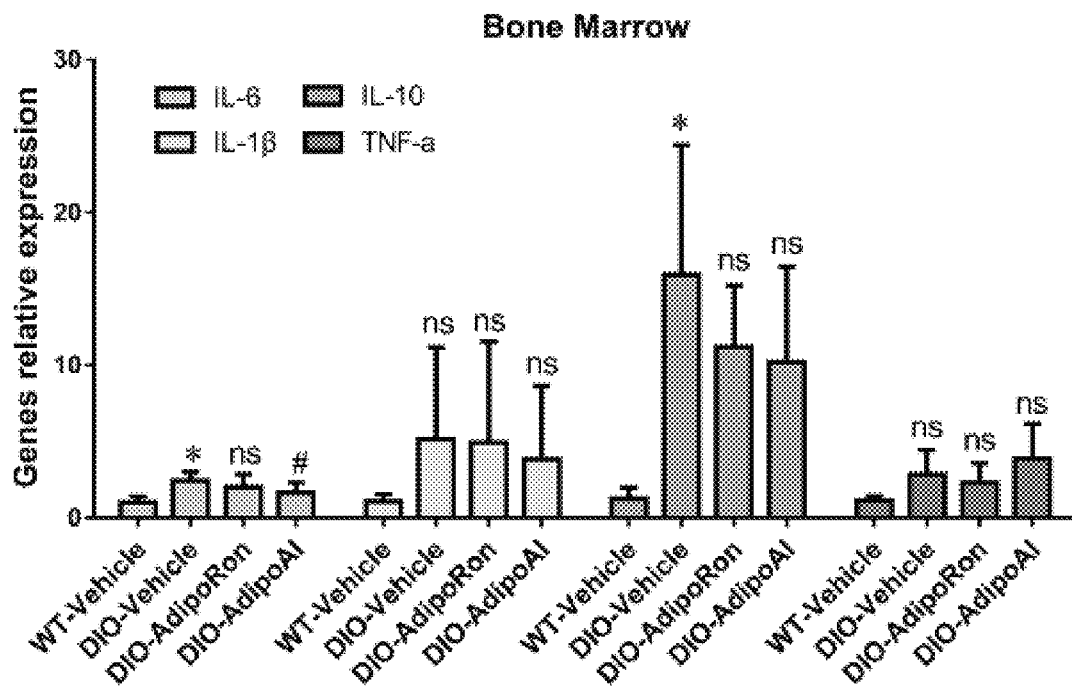
FIG. 3 AdipoAI decreases inflammation in DIO mice (n=6). DIO mice were orally gavaged with APR (50 mg/kg) or AdipoAI (25 mg/kg) for 14 days, and control animals (WT or DIO mice) were administered with equivalent volumes of DMSO. mRNA expression levels of pro-inflammatory cytokines in (a) WAT, (b) spleen and (c) bone marrow were measured by qRT-PCR and normalized to the level of β-actin mRNA. Data are expressed as mean±SEM. (d) Serum levels of IL-6 and IL-1β were measured by ELISA. Data are expressed as mean±SEM. Representative images of H&E (e) and IHC of F4/80 staining (f) of spleen tissue in DIO mice (n=6). Red arrow indicates multinucleated giant cells (megakaryocytes). One-way ANOVA test for multiple-group comparisons, * vs. WT-vehicle group, #vs. DIO-vehicle group. */#P<0.05, significant differences between each indicated group. ns, not significant.
Figure 3:
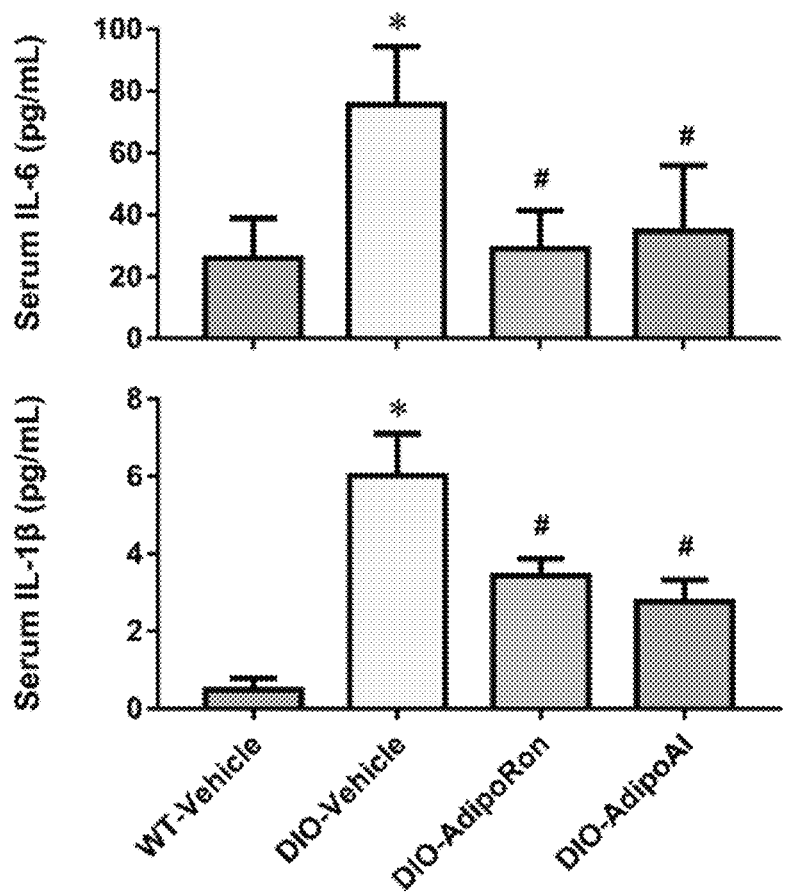
Figure 3:
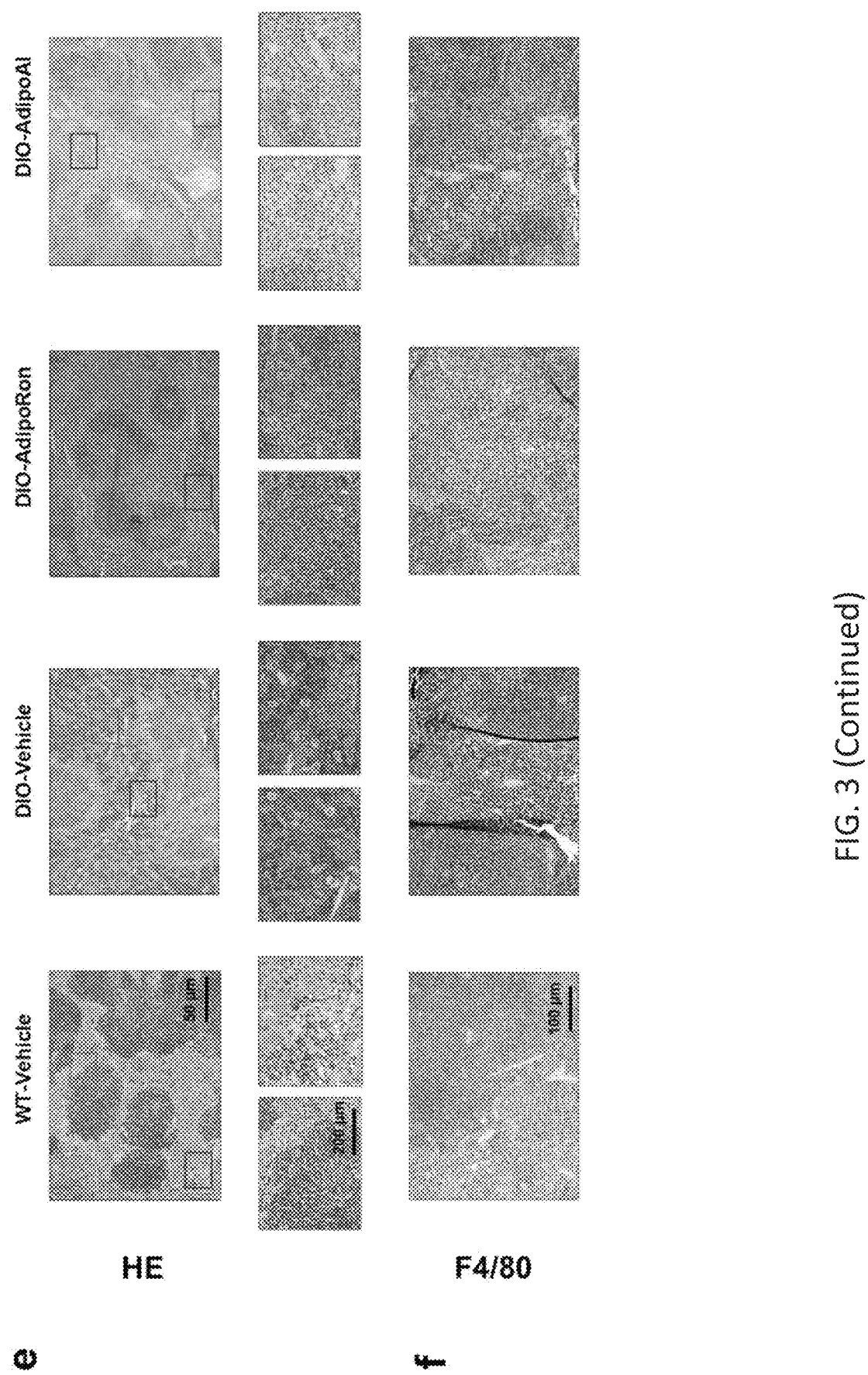

Obesity is frequently accompanied by chronic low-level inflammation over the whole body and may increase the morbidity of infections (Ouchi & Walsh, 2007). It has also been shown to cause a deficiency of APN in the bone marrow (BM), inflamed BM, and increased proinflammation cytokines production from bone marrow macrophages (Masamoto et al., 2016). In vivo studies were conducted with the DIO mouse model, which were previously used for metabolic studies with APN and APR (Okada-Iwabu et al., 2013; Wu et al., 2019). Treatment with AdipoAI and APR inhibited the expression levels of IL-6 and IL-1β in WAT, spleen, and bone marrow as well as the IL-6 and IL-1β serum levels in DIO mice (FIG. 3).

Figure 4:
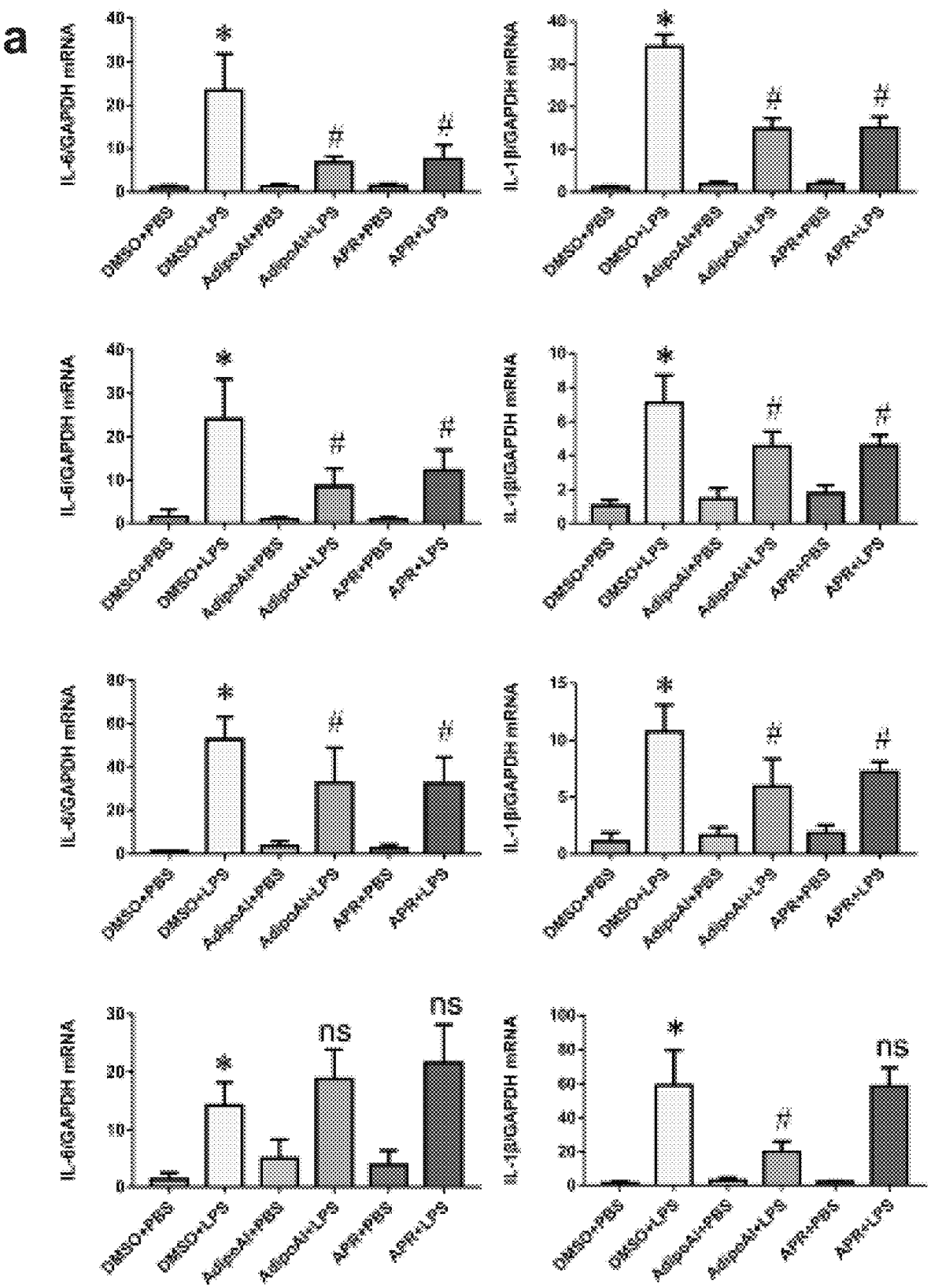
FIG. 4 AdipoAI protects against LPS-induced endotoxemia. Endotoxemia was induced in WT mice by intraperitoneal injection with LPS (25 mg/kg), and control littermates were administered with equivalent volumes of PBS. APR or AdipoAI were orally gavaged into mice for 24 hours before LPS challenge and control animals were administered with equivalent volumes of DMSO. (a) mRNA expression levels of pro-inflammatory cytokines in lung, spleen, liver and WAT were measured by qRT-PCR and normalized with GAPDH mRNA levels. Data are shown as mean±SEM (n=6). (b) Survival curve of mice with endotoxemia (n=12). (c) Serum levels of IL-6 and IL-1β were measured by ELISA. Data are expressed as mean±SEM (n=6). (d) Histopathology for lung, spleen, liver and WAT tissues isolated from APR- or AdipoAI-treated mice 24 h before LPS challenge (n=6). Upper panel: Hematoxylin and eosin staining; Lower panel: Immunohistochemical staining for macrophage marker F4/80. Red arrow indicates F4/80 positive cells. One-way ANOVA test for multiple-group comparisons, * vs. DMSO+PBS group, #vs. DMSO+LPS group. */#P<0.05, significant differences between each indicated group. ns, not significant.
Figure 4:
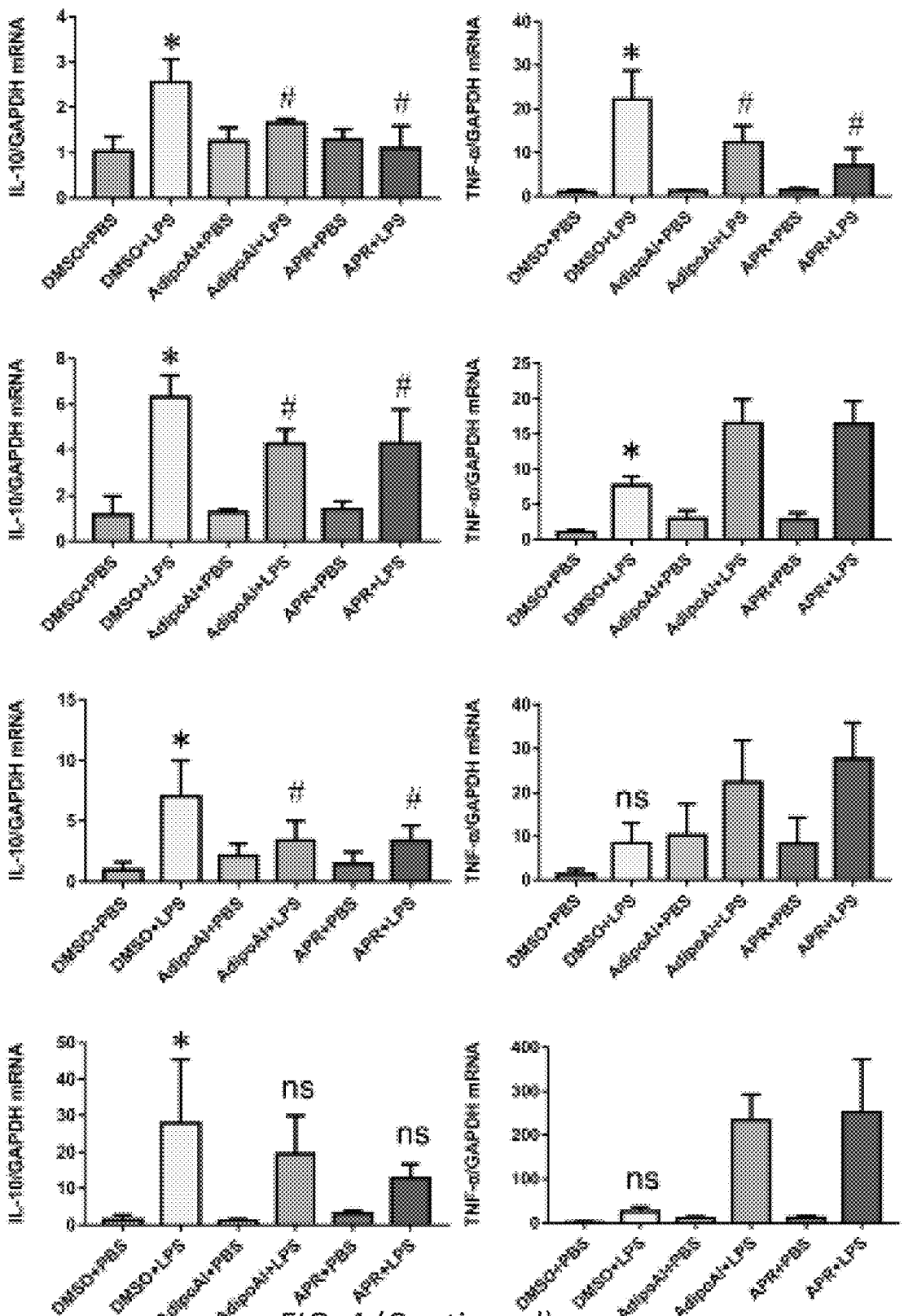
Figure 4:
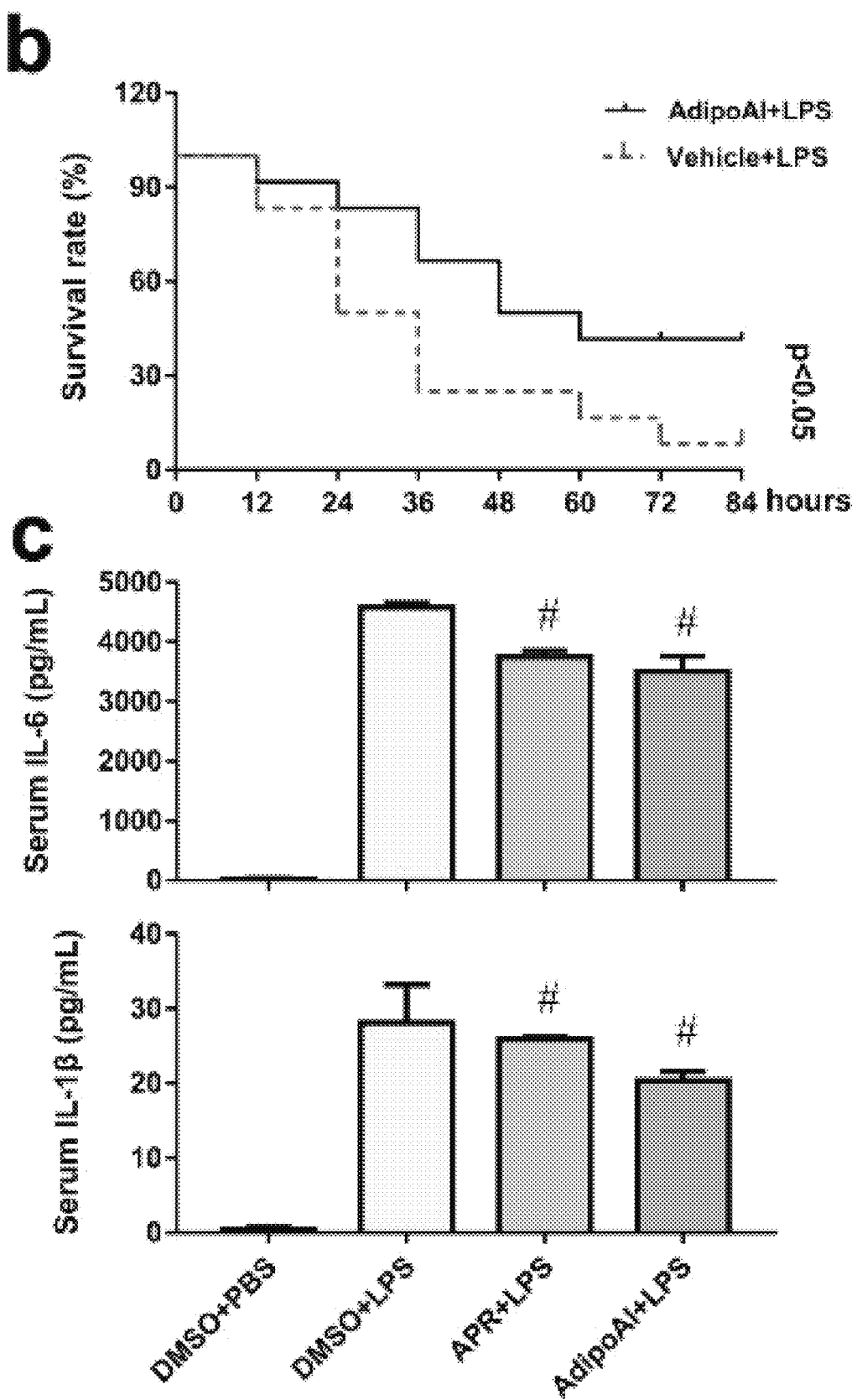
Figure 4:
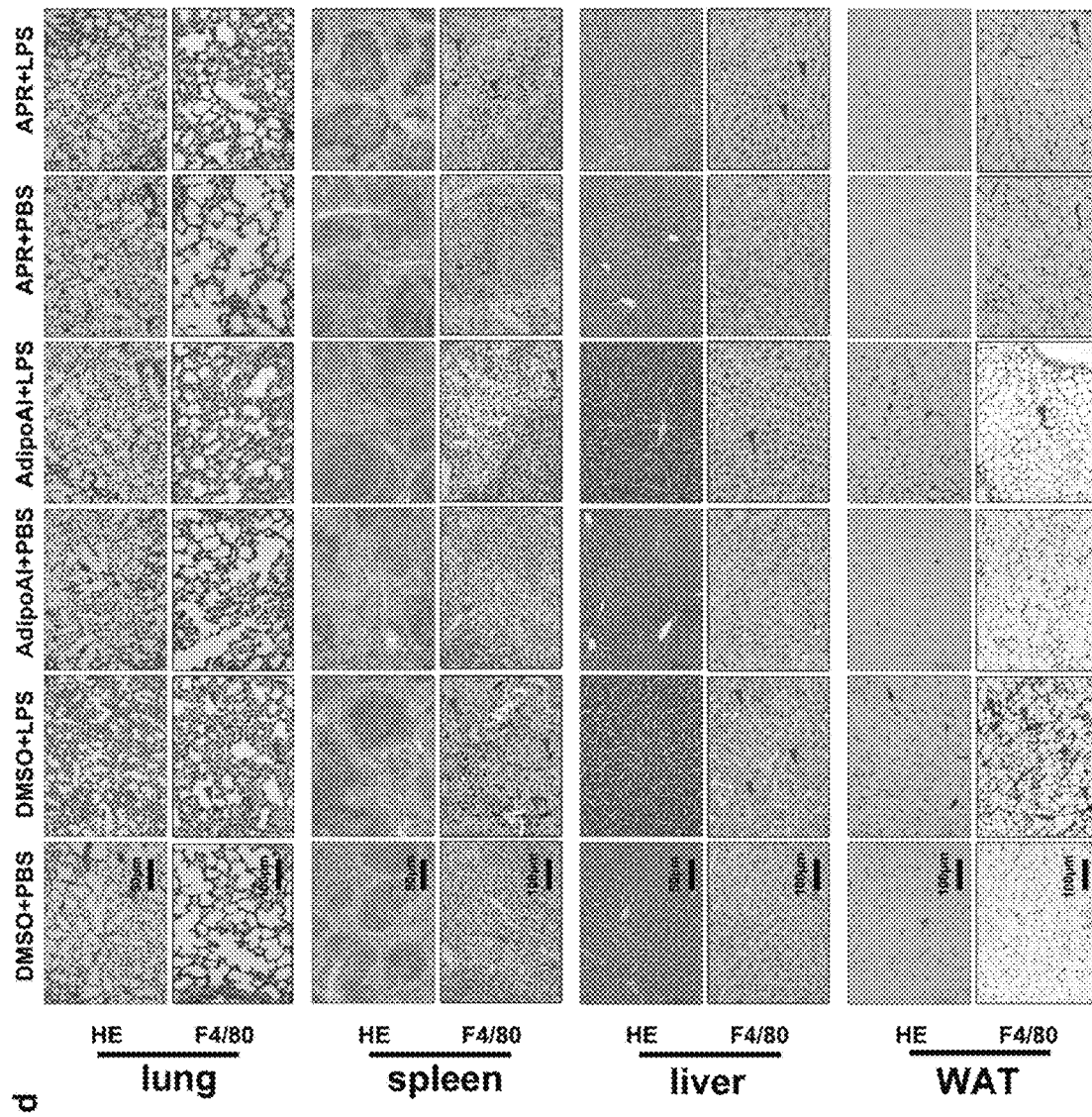
Figure 12:
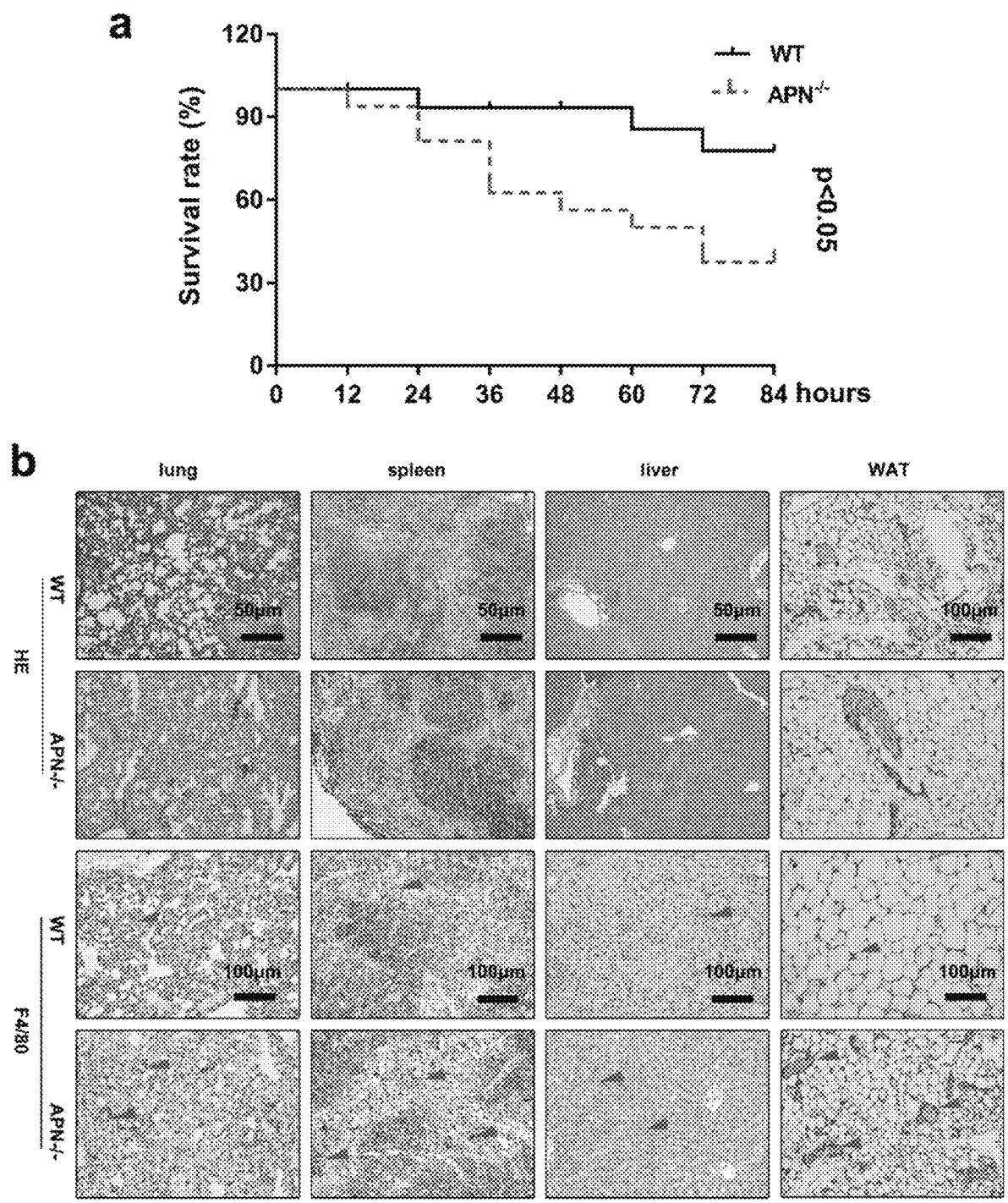
FIG. 12 APN−/− mice show a more severe endotoxemia that WT mice. Endotoxemia was induced in WT and APN−/− mice by intraperitoneal injection of LPS (15 mg/kg). (a) Survival curve of mice with endotoxemia (n=16). (b) Histopathology in lung, spleen, liver, and WAT of WT or APN−/− mice with LPS challenge (n=6). Upper panel: Hematoxylin and eosin staining; Lower panel: Immunohistochemical staining for macrophage marker F4/80. Red arrow indicates F4/80 positive cells. Quantitative analysis of positive cells of HE staining (c) and F4/80 positive cells (d) in (b). Data are expressed as mean±SEM (n=6). Two-tailed Student's t-test for two groups. *$P<0.05$, significant differences between each indicated group. ns: not significant.
Figure 12:
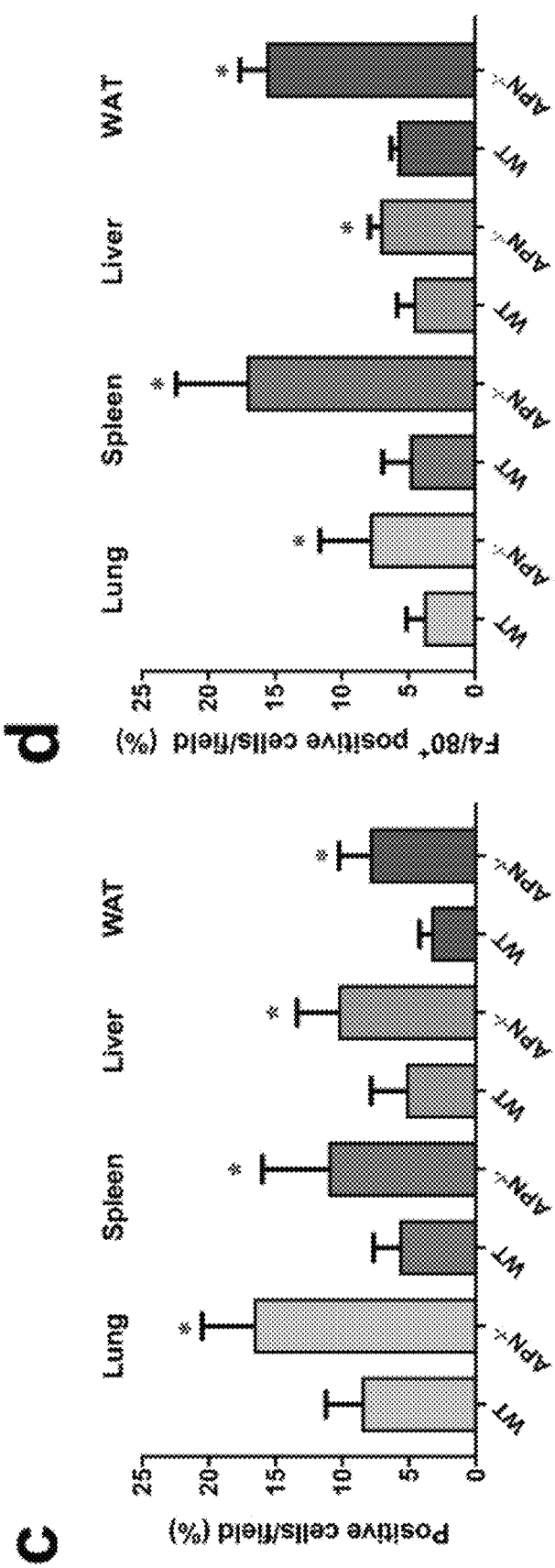

The function of APN in LPS-induced endotoxemia in vivo is not well known. APN$^{-/-}$ mice treated with LPS exhibited more severe tissue damage and lower survival rate than LPS-induced WT mice (FIG. 12). In addition, AdipoAI played a protective role against LPS-induced endotoxemia in mice (FIG. 4). Others have shown that inflammatory reaction in atherosclerosis and ethanol-induced liver injury were also influenced by APN (Folco et al., 2009; Thakur et al., 2006). These results support the notion that compounds activating APN signaling could be used in the future in the prevention of acute infections such as sepsis and septic shock.

APN mediates anti-inflammatory properties in macrophages via diverse signaling mechanisms. On one hand, treatment of APN alone was reported to drive sustained levels of phosphorylation of IκB, JNK, p38, and STAT3, but prevented further activation of these signaling molecules in the presence of LPS (Folco et al., 2009). Those findings provided a mechanistic basis for previous observations suggesting that APN could induce inflammatory activation to some extent, that is likely to mediate tolerance to further treatment with pro-inflammatory stimuli (Sattar et al., 2006; Yamaguchi et al., 2005). However, it was found that phosphorylation levels of JNK, Erk, and Akt were not significantly different in AdipoAI-stimulated or AdipoAI and LPS-stimulated macrophages (FIG. 5a). Furthermore, AdipoAI inhibited the phosphorylation of upstream kinase IRAK4 and subsequently suppressed the NF-κB and p38 MAPK signaling pathways in LPS-induced macrophages. The transcription factors NF-κB and p38 are known to contribute to LPS-stimulated inflammatory response, and IL-6 and IL-1β are their target genes in macrophages.

Activation of APN receptor AdipoR1 and AdipoR2 by APN leads to activation of AMPK and/or PPAR-α40 in vivo (Okada-Iwabu et al., 2013) as well as binding of adapter proteins APPL1 and APPL2 to APN receptors (Mao et al., 2006).These results suggested that AdipoR1 and APPL1 but not AdipoR2 and APPL2 (FIGS. 5c, f and g) participated in the anti-inflammatory effects of AdipoAI in Raw264.7 cells. Furthermore, APPL1 protein expression was increased by AdipoAI and APR but decreased by LPS (FIG. 5d). Other researchers have reported that APPLs KO mice are more prone to endotoxic shock when challenged by LPS (Mao et al., 2014) and that TLR3/4 ligands trigger APPL1 degradation in LPS-induced murine BMMs (Chau et al., 2015). Taken together these results (FIG. 5e) and prior reports (Chau et al., 2015; Mao et al., 2014), it is tempting to speculate that a crosstalk between APN and LPS signaling pathways may exist that involves APPL1 to regulate inflammatory responses in macrophages. In agreement with the involvement of APPL1 in the anti-inflammatory effects of AdipoAI in LPS-induced inflammatory response in macrophages, it was found that APPL1 suppression by APPL1 siRNA affected phosphorylation of IRAK4 and p38 MAPK in response to AdipoAI and LPS (FIG. 5f, g).

Adapter protein MyD88 plays a pivotal role in LPS stimulating proinflammatory signaling pathways (Hirotani et al., 2005; Skaug et al., 2009) and it was demonstrated that MyD88 is involved in the expression of proinflammatory cytokines and the activation of downstream signaling pathways in LPS-stimulated macrophages (FIG. 6a, b). Furthermore, it was found AdipoR1, APPL1 and MyD88 formed a protein complex which is expected to contribute to the anti-inflammatory effects of AdipoAI in LPS-induced Raw264.7 cells (FIG. 6c). APPL1 is recognized as a multifunctional endosomal signaling adaptor protein that is capable of binding to many interacting proteins, such as AdipoR1, APPL2, Rab5, Rab21, DCC, Akt, TBK1 and IKK, and it can activate different signaling pathways (Chau et al., 2015; Diggins & Webb, 2017). The p85 subunit of PI3K, but not MyD88 was shown to be associated with APPL2 and APPL1 in LPS-induced murine BMMs (Mao et al., 2014). These differences are difficult to reconcile but may be related to the different macrophage types used by various laboratories.

c-Maf was previously shown to regulate disease-specific gene networks to mediate immune responses in immune cells and macrophages (Daassi et al., 2016; van den Bosch, Palsson-Mcdermott, Johnson, & O'Neill, 2014; Xu et al., 2018). It was found AdipoAI inhibited c-Maf mRNA expression in vitro and in vivo (FIG. 7 and FIG. 13) and gathered experimental evidence that supported a critical role of c-Maf in the activation of the inflammatory response in LPS-induced Raw264.7 cells through c-Maf siRNA experiments (FIG. 6a). Previously, investigators showed that LPS activated c-Maf transcription promotes IL-10 production in early-stage BMMs (van den Bosch et al., 2014). It is therefore likely that AdipoAI inhibited IL-10 production in this study partly because of the inhibited transcriptional activity of c-Maf in LPS-induced macrophages. And it was also found that MyD88 appeared to regulate the mRNA expression of c-Maf in Raw264.7 cells to some degree (FIG. 6a).

Figure 8:
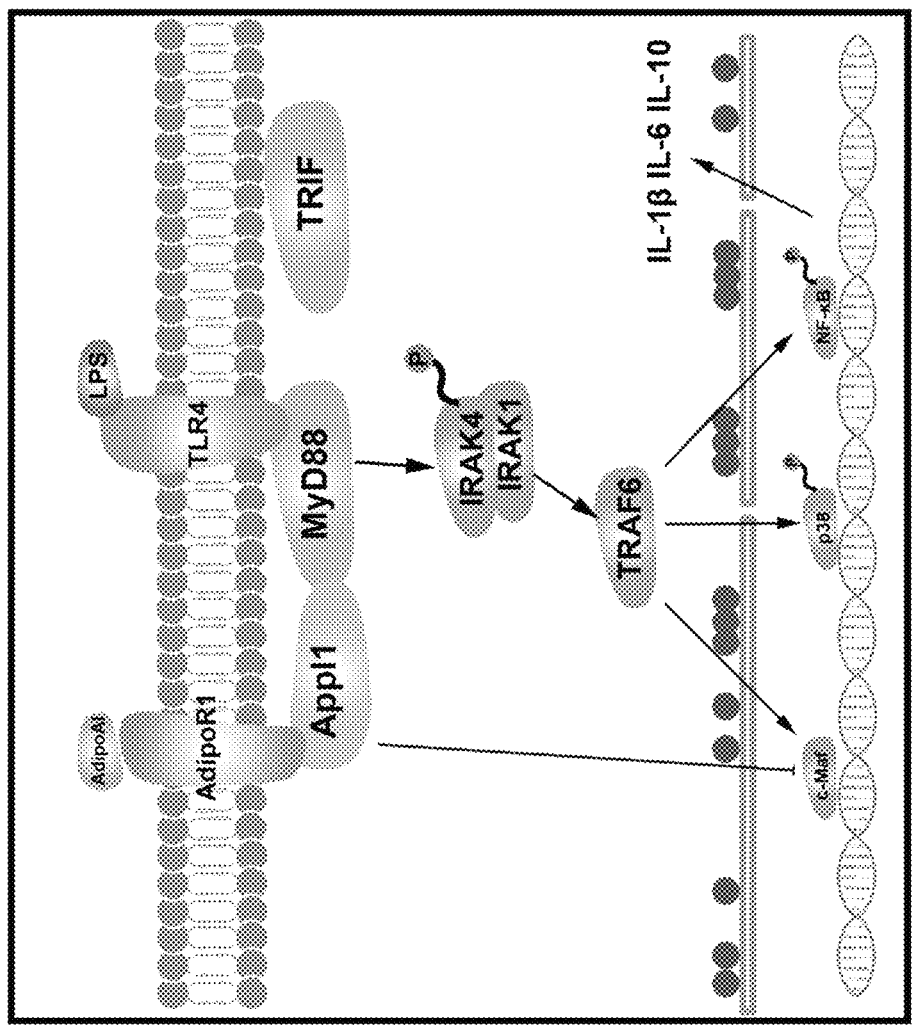
FIG. 8 Diagram of AdipoAI-elicited molecular mechanisms to inhibit inflammatory responses in LPS-induced macrophages. AdipoAI activates AdipoR1/APPL1 pathways, and MyD88 is recruited to form a protein complex with APPL1, inhibiting activation of IRAK4, NF-κB, MAPK, and c-Maf pathways and suppressing production of proinflammatory cytokines including IL-6 and IL-1β in LPS-induced macrophages. AdipoAI also inhibit transcriptional activation of c-maf directly, then suppressing production of IL-6 and IL-1β in macrophages.

In summary, this study characterized the strong ability of AdipoAI to attenuate inflammation in DIO and LPS-induced endotoxemia mice with low cytotoxicity. Regarding the underlying molecular mechanisms, these results suggested that AdipoR1/APPL1 and MyD88 formed a stable complex, which subsequently inhibited activation of NF-κB, MAPK and c-Maf pathways and limited production of proinflammatory cytokines in LPS-induced macrophages (FIG. 8). Additionally, AdipoAI also directly inhibited the activation of c-Maf. Taken together, the results presented illustrate the use of AdipoR agonists, such as AdipoAI, to target LPS-induced inflammatory disorders and other inflammatory diseases, particularly in diabetic patients.

REFERENCES

Aderem, A., & Ulevitch, R. J. (2000). Toll-like receptors in the induction of the innate immune response. *Nature*, 406(6797), 782-787. doi: 10.1038/35021228

Alexander S P H, Roberts R E, Broughton B R S, Sobey C G, George C H, Stanford S C et al. (2018). Goals and practicalities of immunoblotting and immunohistochemistry: A guide for submission to the British Journal of Pharmacology. Br J Pharmacol 175: 407-411. doi: 10.1111/bph.14112

Alexander S P, Christopoulos A, Davenport A P, Kelly E, Mathie A, Peters J A, et al. (2019). THE CONCISE GUIDE TO PHARMACOLOGY 2019/20: G protein-coupled receptors. Br J Pharmacol 176: S21-S141. doi: 10.1111/bph.14748

Barton, G. M. (2008). A calculated response: control of inflammation by the innate immune system. *J Clin Invest*, 118(2), 413-420. doi: 10.1172/JCI34431

Brochu-Gaudreau, K., Rehfeldt, C., Blouin, R., Bordignon, V., Murphy, B. D., & Palin, M. F. (2010). Adiponectin action from head to toe. *Endocrine*, 37(1), 11-32. doi: 10.1007/s12020-009-9278-8

Bruce, C. R., Mertz, V. A., Heigenhauser, G. J., & Dyck, D. J. (2005). The stimulatory effect of globular adiponectin on insulin-stimulated glucose uptake and fatty acid oxidation is impaired in skeletal muscle from obese subjects. *Diabetes*, 54(11), 3154-3160. doi: 10.2337/diabetes.54.11.3154

Cao, S., Liu, J., Song, L., & Ma, X. (2005). The proto-oncogene c-Maf is an essential transcription factor for IL-10 gene expression in macrophages. *J Immunol*, 174(6), 3484-3492. doi: 10.4049/jimmunol.174.6.3484

Chau, T. L., Goktuna, S. I., Rammal, A., Casanova, T., Duong, H. Q., Gatot, J. S., Chariot, A. (2015). A role for APPL1 in TLR3/4-dependent TBK1 and IKKepsilon activation in macrophages. *J Immunol*, 194(8), 3970-3983. doi: 10.4049/jimmunol.1401614

Chen, L., Deng, H., Cui, H., Fang, J., Zuo, Z., Deng, J., Zhao, L. (2018). Inflammatory responses and inflammation-associated diseases in organs. *Oncotarget*, 9(6), 7204-7218. doi: 10.18632/oncotarget.23208

Cheng, X., Folco, E. J., Shimizu, K., & Libby, P. (2012). Adiponectin induces pro-inflammatory programs in human macrophages and CD4+ T cells. *J Biol Chem*, 287(44), 36896-36904. doi: 10.1074/jbc.M112.409516

Curtis M J, Bond R A, Spina D, Ahluwalia A, Alexander S P, Giembycz M A et al. (2015). Experimental design and analysis and their reporting: new guidance for publication in BJP. Br J Pharmacol 172: 3461-3471. doi: 10.1111/bph.12856

Curtis M J, Alexander S, Cirino G, Docherty J R, George C H, Giembycz M A et al. (2018). Experimental design and analysis and their reporting II: updated and simplified guidance for authors and peer reviewers. Br J Pharmacol, 175: 987-993. doi: 10.1111/bph.14153

Daassi, D., Hamada, M., Jeon, H., Imamura, Y., Nhu Tran, M. T., & Takahashi, S. (2016). Differential expression patterns of MafB and c-Maf in macrophages in vivo and in vitro. *Biochem Biophys Res Commun*, 473(1), 118-124. doi: 10.1016/j.bbrc.2016.03.063

Deepa, S. S., & Dong, L. Q. (2009). APPL1: role in adiponectin signaling and beyond. *Am J Physiol Endocrinol Metab*, 296(1), E22-36. doi: 10.1152/ajpendo.90731.2008

Diggins, N. L., & Webb, D. J. (2017). APPL1 is a multifunctional endosomal signaling adaptor protein. *Biochem Soc Trans*, 45(3), 771-779. doi: 10.1042/BST20160191

Du, M., Yuan, L., Tan, X., Huang, D., Wang, X., Zheng, Z., Huang, K. (2017). The LPS-inducible lncRNA Mirt2 is a negative regulator of inflammation. *Nat Commun*, 8(1), 2049. doi: 10.1038/s41467-017-02229-1

Folco, E. J., Rocha, V. Z., Lopez-Ilasaca, M., & Libby, P. (2009). Adiponectin inhibits pro-inflammatory signaling in human macrophages independent of interleukin-10. *J Biol Chem*, 284(38), 25569-25575. doi: 10.1074/jbc.M109.019786

Foster, S. L., & Medzhitov, R. (2009). Gene-specific control of the TLR-induced inflammatory response. *Clin Immunol*, 130(1), 7-15. doi: 10.1016/j.clim.2008.08.015

Hirotani, T., Yamamoto, M., Kumagai, Y., Uematsu, S., Kawase, I., Takeuchi, O., & Akira, S. (2005). Regulation of lipopolysaccharide-inducible genes by MyD88 and Toll/IL-1 domain containing adaptor inducing IFN-beta. *Biochem Biophys Res Commun*, 328(2), 383-392. doi: 10.1016/j.bbrc.2004.12.184

Kilkenny C, Browne W, Cuthill I C, Emerson M, Altman D G, Group NCRRGW (2010). Animal research: reporting in vivo experiments: the ARRIVE guidelines. Br J Pharmacol 160: 1577-1579. doi: 10.1111/j.1476-5381.2010.00872.x Kawai, T., & Akira, S. (2010). The role of pattern-recognition receptors in innate immunity: update on Toll-like receptors. *Nat Immunol*, 11(5), 373-384. doi: 10.1038/ni.1863

Kim, J. I., Ho Ic Fau-Grusby, M. J., Grusby Mj Fau-Glimcher, L. H., & Glimcher, L. H. (1999). The transcription factor c-Maf controls the production of interleukin-4 but not other Th2 cytokines. *Immunity*, 10(6), 745-751.

Kim, M. J., Kim, E. H., Pun, N. T., Chang, J. H., Kim, J. A., Jeong, J. H., Park, P. H. (2017). Globular Adiponectin Inhibits Lipopolysaccharide-Primed Inflammasomes Activation in Macrophages via Autophagy Induction: The Critical Role of AMPK Signaling. *Int J Mol Sci,* 18(6). doi: 10.3390/ijms18061275

Kishimoto, K., Matsumoto, K., & Ninomiya-Tsuji, J. (2000). TAK1 mitogen-activated protein kinase kinase kinase is activated by autophosphorylation within its activation loop. *J Biol Chem,* 275(10), 7359-7364. doi: 10.1074/jbc.275.10.7359

Kobashi, C., Urakaze, M., Kishida, M., Kibayashi, E., Kobayashi, H., Kihara, S., Kobayashi, M. (2005). Adiponectin inhibits endothelial synthesis of interleukin-8. *Circ Res,* 97(12), 1245-1252. doi: 10.1161/01.RES.0000194328.57164.36

Kumada, M., Kihara, S., Ouchi, N., Kobayashi, H., Okamoto, Y., Ohashi, K., Matsuzawa, Y. (2004). Adiponectin specifically increased tissue inhibitor of metalloproteinase-1 through interleukin-10 expression in human macrophages. *Circulation,* 109(17), 2046-2049. doi: 10.1161/01.CIR.0000127953.98131.ED Lamothe, B., Besse, A., Campos, A. D., Webster, W. K., Wu, H., & Darnay, B. G. (2007). Site-specific Lys-63-linked tumor necrosis factor receptor-associated factor 6 auto-ubiquitination is a critical determinant of I kappa B kinase activation. *J Biol Chem,* 282(6), 4102-4112. doi: 10.1074/jbc.M609503200

Lian, J., Wu, X., Liu, Y., Qiu, W., Zhu, X., Wang, X., Meng, S., Valverde, P., Steffensen, B., Tu, Q., Pan, J., Chen, J. (2019). Potential roles of miR-335-5p on pathogenesis of experimental periodontitis. *J Periodontal Res,* 21. doi: 10.1111/jre.12701

Lovren, F., Pan, Y., Quan, A., Szmitko, P. E., Singh, K. K., Shukla, P. C., Verma, S. (2010). Adiponectin primes human monocytes into alternative anti-inflammatory M2 macrophages. Am J Physiol Heart Circ Physiol, 299(3), H656-663. doi: 10.1152/ajpheart.00115.2010

Mandal, P., Park, P. H., McMullen, M. R., Pratt, B. T., & Nagy, L. E. (2010). The anti-inflammatory effects of adiponectin are mediated via a heme oxygenase-1-dependent pathway in rat Kupffer cells. *Hepatology,* 51(4), 1420-1429. doi: 10.1002/hep.23427

Mandal, P., Pratt, B. T., Barnes, M., McMullen, M. R., & Nagy, L. E. (2011). Molecular mechanism for adiponectin-dependent M2 macrophage polarization: link between the metabolic and innate immune activity of full-length adiponectin. J Biol Chem, 286(15), 13460-13469. doi: 10.1074/jbc.M110.204644

Mao, L., Lin, W., Nie, T., Hui, X., Gao, X., Li, K., Wu, D. (2014). Absence of Appl2 sensitizes endotoxin shock through activation of PI3K/Akt pathway. *Cell Biosci,* 4(1), 60. doi: 10.1186/2045-3701-4-60

Mao, X., Kikani, C. K., Riojas, R. A., Langlais, P., Wang, L., Ramos, F. J., Dong, L. Q. (2006). APPL1 binds to adiponectin receptors and mediates adiponectin signalling and function. *Nat Cell Biol,* 8(5), 516-523. doi: 10.1038/ncb1404

Masamoto, Y., Arai, S., Sato, T., Yoshimi, A., Kubota, N., Takamoto, I., Kurokawa, M. (2016). Adiponectin Enhances Antibacterial Activity of Hematopoietic Cells by Suppressing Bone Marrow Inflammation. *Immunity,* 44(6), 1422-1433. doi: 10.1016/j.immuni.2016.05.010

McGrath J C, Lilley E (2015). Implementing guidelines on reporting research using animals (ARRIVE etc.): new requirements for publication in BJP. Br J Pharmacol 172: 3189-3193

Medzhitov, R., & Horng, T. (2009). Transcriptional control of the inflammatory response. *Nat Rev Immunol,* 9(10), 692-703. doi: 10.1038/nri2634

Murray, P. J., Allen, J. E., Biswas, S. K., Fisher, E. A., Gilroy, D. W., Goerdt, S., Wynn, T. A. (2014). Macrophage activation and polarization: nomenclature and experimental guidelines. *Immunity,* 41(1), 14-20. doi: 10.1016/j.immuni.2014.06.008

Murray, P. J., & Smale, S. T. (2012). Restraint of inflammatory signaling by interdependent strata of negative regulatory pathways. *Nat Immunol,* 13(10), 916-924. doi: 10.1038/ni.2391

Nicolas, S., Chabry, J., Guyon, A., Zarif, H., Heurteaux, C., Petit-Paitel, A. (2018). Adiponectin: an endogenous molecule with anti-inflammatory and antidepressant properties? *Med Sci (Paris),* 34(5), 417-423. doi: 10.1051/medsci/20183405014

Harding S D, Sharman J L, Faccenda E, Southan C, Pawson A J, Ireland S, et al. (2018). The IUPHAR/BPS Guide to PHARMACOLOGY in 2018: updates and expansion to encompass the new guide to IMMUNOPHARMACOLOGY. Nucleic Acids Res 46: D1091-1106. doi: 10.1093/nar/gkx1121

Hashi, K., Parker, J. L., Ouchi, N., Higuchi, A., Vita, J. A., Gokce, N., Walsh, K. (2010). Adiponectin promotes macrophage polarization toward an anti-inflammatory phenotype. J Biol Chem, 285(9), 6153-6160. doi: 10.1074/jbc.M109.088708

Ohashi, K., Shibata, R., Murohara, T., & Ouchi, N. (2014). Role of anti-inflammatory adipokines in obesity-related diseases. *Trends Endocrinol Metab,* 25(7), 348-355. doi: 10.1016/j.tem.2014.03.009

Okada-Iwabu, M., Yamauchi, T., Iwabu, M., Honma, T., Hamagami, K., Matsuda, K., Kadowaki, T. (2013). A small-molecule AdipoR agonist for type 2 diabetes and short life in obesity. *Nature,* 503(7477), 493-499. doi: 10.1038/nature12656

Ouchi, N., & Walsh, K. (2007). Adiponectin as an anti-inflammatory factor. *Clin Chim Acta,* 380(1-2), 24-30. doi: 10.1016/j.cca.2007.01.026

Piao, W., Song, C., Chen, H., Diaz, M. A., Wahl, L. M., Fitzgerald, K. A., Medvedev, A. E. (2009). Endotoxin tolerance dysregulates MyD88- and Toll/IL-1R domain-containing adapter inducing IFN-beta-dependent pathways and increases expression of negative regulators of TLR signaling. *J Leukoc Biol,* 86(4), 863-875. doi: 10.1189/jlb.0309189

Pun, N. T., Subedi, A., Kim, M. J., & Park, P. H. (2015). Globular Adiponectin Causes Tolerance to LPS-Induced TNF-alpha Expression via Autophagy Induction in RAW 264.7 Macrophages: Involvement of SIRT1/FoxO3A Axis. *PLoS One,* 10(5), e0124636. doi: 10.1371/journal.pone.0124636

Salomao, R., Brunialti, M. K., Rapozo, M. M., Baggio-Zappia, G. L., Galanos, C., & Freudenberg, M. (2012). Bacterial sensing, cell signaling, and modulation of the immune response during sepsis. *Shock,* 38(3), 227-242. doi: 10.1097/SHK.0b013e318262c4b0

Sattar, N., Wannamethee, G., Sarwar, N., Tchernova, J., Cherry, L., Wallace, A. M., Whincup, P. H. (2006). Adiponectin and coronary heart disease: a prospective study and meta-analysis. *Circulation,* 114(7), 623-629. doi: 10.1161/CIRCULATIONAHA.106.618918

Skaug, B., Jiang, X., & Chen, Z. J. (2009). The role of ubiquitin in NF-kappaB regulatory pathways. *Annu Rev Biochem,* 78, 769-796. doi: 10.1146/annurev.biochem.78.070907.102750

Thakur, V., Pritchard, M. T., McMullen, M. R., & Nagy, L. E. (2006). Adiponectin normalizes LPS-stimulated TNF-alpha production by rat Kupffer cells after chronic ethanol feeding. *Am J Physiol Gastrointest Liver Physiol,* 290(5), G998-1007. doi: 10.1152/ajpgi.00553.2005

Tilija Pun, N., & Park, P. H. (2018). Adiponectin inhibits inflammatory cytokines production by Beclin-1 phosphorylation and B-cell lymphoma 2 mRNA destabilization: role for autophagy induction. *Br J Pharmacol,* 175(7), 1066-1084. doi: 10.1111/bph.14144

Tu, Q., Zhang, J., Dong, L. Q., Saunders, E., Luo, E., Tang, J., & Chen, J. (2011). Adiponectin inhibits osteoclastogenesis and bone resorption via APPL1-mediated suppression of Aktl. *J Biol Chem,* 286(14), 12542-12553. doi: 10.1074/jbc.M110.152405 van den Bosch, M. W., Palsson-Mcdermott, E., Johnson, D. S., & O'Neill, L. A. (2014). LPS induces the degradation of programmed cell death protein 4 (PDCD4) to release Twist2, activating c-Maf transcription to promote interleukin-10 production. *J Biol Chem,* 289(33), 22980-22990. doi: 10.1074/jbc.M114.573089

Wang, N., Liang, H., & Zen, K. (2014). Molecular mechanisms that influence the macrophage m1-m2 polarization balance. *Front Immunol,* 5, 614. doi: 10.3389/fimmu.2014.00614

Wess, J. (1997). G-protein-coupled receptors: molecular mechanisms involved in receptor activation and selectivity of G-protein recognition. *FASEB J,* 11(5), 346-354.

Wolf, A. M., Wolf, D., Rumpold, H., Enrich, B., & Tilg, H. (2004). Adiponectin induces the anti-inflammatory cytokines IL-10 and IL-1RA in human leukocytes. *Biochem Biophys Res Commun,* 323(2), 630-635. doi: 10.1016/j.bbrc.2004.08.145

Wu, X., Qiu, W., Hu, Z., Lian, J., Liu, Y., Zhu, X., Chen, J. (2019). An Adiponectin Receptor Agonist Reduces Type 2 Diabetic Periodontitis. *J Dent Res,* 98(3), 313-321. doi: 10.1177/0022034518818449

Wulster-Radcliffe, M. C., Ajuwon, K. M., Wang, J., Christian, J. A., & Spurlock, M. E. (2004). Adiponectin differentially regulates cytokines in porcine macrophages. *Biochem Biophys Res Commun,* 316(3), 924-929. doi: 10.1016/j.bbrc.2004.02.130

Xie, Q., McGreal, R., Harris, R., Gao, C. Y., Liu, W., Reneker, L. W., Cvekl, A. (2016). Regulation of c-Maf and alphaA-Crystallin in Ocular Lens by Fibroblast Growth Factor Signaling. *J Biol Chem,* 291(8), 3947-3958. doi: 10.1074/jbc.M115.705103

Xu, M., Pokrovskii, M., Ding, Y., Yi, R., Au, C., Harrison, O. J., Littman, D. R. (2018). c-MAF-dependent regulatory T cells mediate immunological tolerance to a gut pathobiont. *Nature,* 554(7692), 373-377. doi: 10.1038/nature25500

Xuan, D., Han, Q., Tu, Q., Zhang, L., Yu, L., Murry, D., Chen, J. (2016). Epigenetic Modulation in Periodontitis: Interaction of Adiponectin and JMJD3-IRF4 Axis in Macrophages. J Cell Physiol, 231(5), 1090-1096. doi: 10.1002/jcp.25201

Yamaguchi, N., Argueta, J. G., Masuhiro, Y., Kagishita, M., Nonaka, K., Saito, T., Yamashita, Y. (2005). Adiponectin inhibits Toll-like receptor family-induced signaling. *FEBS Lett,* 579(30), 6821-6826. doi: 10.1016/j.febslet.2005.11.019

Yamauchi, T., Kamon, J., Ito, Y., Tsuchida, A., Yokomizo, T., Kita, S., Kadowaki, T. (2003). Cloning of adiponectin receptors that mediate antidiabetic metabolic effects. *Nature,* 423(6941), 762-769. doi: 10.1038/nature01705

Yokota, T., Oritani, K., Takahashi, I., Ishikawa, J., Matsuyama, A., Ouchi, N., Matsuzawa, Y. (2000). Adiponectin, a new member of the family of soluble defense collagens, negatively regulates the growth of myelomonocytic progenitors and the functions of macrophages. *Blood,* 96(5), 1723-1732.

Zhang, J., Valverde, P., Zhu, X., Murray, D., Wu, Y., Yu, L., Chen, J. (2017). Exercise-induced irisin in bone and systemic irisin administration reveal new regulatory mechanisms of bone metabolism. *Bone Res,* 5, 16056. doi: 10.1038/boneres.2016.56

Zhang, L., Meng, S., Tu, Q., Yu, L., Tang, Y., Dard, M. M., Chen, J. (2014). Adiponectin ameliorates experimental periodontitis in diet-induced obesity mice. *PLoS One,* 9(5), e97824. doi: 10.1371/journal.pone.0097824

Example 2

Adiponectin Receptor Agonists Ameliorate Type 2 Diabetes-Associated Periodontitis by Enhancing Autophagy in Osteoclasts Type 2 diabetes (T2D)-associated periodontitis is severe and refractory in many cases. Considered an inflammatory disease, T2D predisposes to periodontitis by increasing whole-body inflammation. One mechanism of increased inflammation is that T2D is mediated by loss of production or function of the anti-inflammatory hormone adiponectin. AdipoR agonists attenuate T2D-associated inflammation by inhibiting osteoclastogenesis and LPS-induced endotoxemia. Autophagy plays an important role during osteoclast differentiation and function. AdipoR agonist AdipoRon inhibited osteoclastogenesis and AdipoAI inhibited osteoclastogenesis at lower doses than AdipoRon without any cytotoxicity. In DIO mice with experimental periodontitis, AdipoAI reduced mouse body weight in 14 days, reducing fasting glucose levels, alveolar bone destruction, osteoclast number along the alveolar bone surface, and decreased the expression of pro-inflammatory factors in periodontal tissues. AdipoAI and AdipoRon also enhanced LC3A/B expression when cultured with RANKL. 3-Methyladenine, a known autophagy inhibitor, decreased LC3A/B expression and reversed the inhibition of osteoclastogenesis during AdipoAI treatment. These results demonstrate that AdipoR agonists, such as AdipoAI, ameliorate the severity of T2D-associated periodontitis by enhancing autophagy in osteoclasts. AdipoAI demonstrates such activity at lower doses than AdipoRon without demonstrable side effects. Thus, AdipoAI has pharmaceutical potential for treating diabetes-associated periodontal disease.

MATERIALS & METHODS

RAW 264.7 cell culture

RAW 264.7 cells (ATCC, Manassas, Va., USA) were cultured and passaged in DMEM supplemented with 10% (v/v) FBS (Invitrogen, Grand Island, N.Y., USA) and 1% Penicillin-Streptomycin (Gibco, Gaithersburg, Md., USA). For the induction of osteoclastogenesis, RAW 264.7 cells were cultured [24] in α-MEM supplemented with 10% FBS and 1% Penicillin-Streptomycin in the presence of 100 ng/ml RANKL (Peprotech, Rocky Hill, N.J., USA) for 2 days, and subsequently treated or not with AdipoRon or AdipoAI for another 2 days changing cell culture medium every 2 days. After a total of 6 days of culture, morphologic examination was performed, as was mRNA and protein expression. To simulate high glucose environment in vitro, α-MEM was supplemented with D-glucose to 25 mmol/l (high glucose) or 5 mmol/l (physiological glucose). 20 mmol/l D-mannitol served as an osmotic control.

CCK-8 Assay

RAW 264.7 cells (2×10³ cells/well) were seeded in 96-well plates and treated with or without AdipoRon or AdipoAI for 48 hours in a humidified chamber at 37° C. in 5% $CO_2$ and air.

Cell viability was determined with the Cell Counting Kit-8 (CCK-8 kit, Dojindo, Santa Clara, Calif., USA) following the manufacturer's recommendations. Briefly, CCK-8 solution (10 μL) was added to each well and cells were incubated in dark for 3 hours. Cell viability was determined by measuring the absorbance at 450 nm.

Mouse Model for Experimental Periodontitis

DIO (C57BL/6J background, Jax #380050) were purchased from the Jackson Laboratory (Bar Harbor, Me., http://www.jax.org/). After acclimatization, animals were fed a high-fat diet (containing 60% kcal from fat, Jackson Laboratory) from 6 weeks of age onwards. Experimental periodontitis was induced in 20-week-old mice by 5-0 silk suture as described previously [26]. Briefly, animals were anesthetized using ketamine/xylazine and buprenorphine and the sutures were placed around the maxillary second molar and tied on the palatal side for 2 weeks. The ethical approval of this study was provided by the IACUC of UCSD. The care and use of laboratory animals and Animal Research was performed in accordance with NIH guidelines.

AdipoRon (50 mg/kg body weight) [23, 24] and the AdipoAI (25 mg/kg body weight) [25] were administered by oral gavage concurrently with establishment of experimental periodontitis for 2 weeks.

Tissue Sampling, Micro-Computed Tomography, and Histology Staining Protocols

Gingival tissues from the palatal side were sampled and immediately stored in liquid nitrogen until further analysis. The skulls were scanned by the Bruker Skyscan micro-CT system (Bruker, Kontich, Belgium). Alveolar bone loss, defined as the distance between the cementoenamel junction (CEJ) to the alveolar bone crest (ABC), was measured at six sites (mesio-buccal, mid-buccal, disto-buccal, mesio-palatal, mid-palatal, and disto-palatal) using Ctan software (http://bruker-microct.com/products/downloads.htm) as previously reported [26]. Periodontal hard tissue sections were stained with Acid Phosphatase, Leukocyte (TRAP) Kit (Sigma, St. Louis, Mo., USA) according to the manufacturer's instructions.

RNA Extraction and RT-qPCR Analysis

Total RNA was isolated from cell cultures and gingival soft tissues using TriZol reagent (Life Technologies, Carlsbad, Calif., USA) according to the manufacturer's instructions [24]. Reverse transcription was performed using the PrimeScript RT Master Mix (Takara Bio, Otsu, Japan) and real-time-qPCR analyses were performed using SYBR-Green Real-Time PCR Master Mix (Takara Bio, Otsu, Japan) as described earlier [27]. Primers used for the PCR amplification are listed in Table 2.

TABLE 2

List of the primers used in real-time qPCR.

| Primer | Forward 5'-3' | Reverse 5'-3' |
|---|---|---|
| LC3 | GACCGCTGTAAGGAGGTGC (SEQ ID NO: 37) | CTTGACCAACTCGCTCATGTTA (SEQ ID NO: 38) |
| IL-6 | CCAAGAGGTGAGTGCTTCCC (SEQ ID NO: 39) | CTGTTGTTCAGACTCTCTCCCT (SEQ ID NO: 40) |
| CCL2 | TTAAAAACCTGGATCGGAACCAA (SEQ ID NO: 41) | GCATTAGCTTCAGATTTACGGGT (SEQ ID NO: 42) |
| β-actin | GGCTGTATTCCCCTCCATCG (SEQ ID NO: 43) | CCAGTTGGTAACAATGCCATGT (SEQ ID NO: 44) |
| TRAP | CACTCCCACCCTGAGATTTGT (SEQ ID NO: 45) | CATCGTCTGCACGGTTCTG (SEQ ID NO: 46) |
| Cathepsin K | GAAGAAGACTCACCAGAAGCAG (SEQ ID NO: 47) | TCCAGGTTATGGGCAGAGATT (SEQ ID NO: 48) |

Preparation of Protein Extracts and Western Blot Analysis

Total cellular extracts were prepared using RIPA Lysis and Extraction Buffer containing three Protease Inhibitors (Santa Cruz, Dallas, Tex., USA). Western blot analyses were performed as previously described [24]. Antibodies for β-actin (1:2000) and GAPDH (1:5000), LC3A/B (1:1000), AKT1 (1:1000), p-AKT1 (1:1000), AKT (1:1000), p-AKT (1:1000), mTOR (1:1000), p-mTOR (1:1000) were purchased from Abcam and Cell Signaling Technology, respectively. SC79, an AKT activator was purchased from Sigma Aldrich. Blots were visualized using ECL chemiluminescence reagents from Thermo Fisher Scientific.

Immunofluorescence Staining

For the detection of the autophagosomes, the RAW 264.7 cells were transfected with a plasmid expressing green fluorescent protein linked LC3 (GFP-LC3) using the Lipofectamine 2000 reagent (Thermo Fisher Scientific, Waltham, Mass., USA) according to the manufacturer's instructions. The fluorescence of GFP-LC3 was detected using a laser scanning confocal microscope (Leica Microsystems, Germany) [28].

Statistical Analysis

Data are presented as mean±SD. Statistical significance between the two groups was evaluated using the student's t-test, and one-way ANOVA was performed followed by Dunnett's test to evaluate the statistical significance among three or more groups. GraphPad Prism 7.0 software was used for all calculations. Results with $p<0.05$ were considered statistically significant and thresholds for significance are expressed as *$P<0.05$, $P<0.01$, and *$P<0.001$.

Results

Anti-Osteoclastogenic Impact of AdipoAI In Vitro

The ability of AdipoRon and AdipoAI to inhibit the osteoclast differentiation by RAW 264.7 cells was evaluated.

Figure 18:
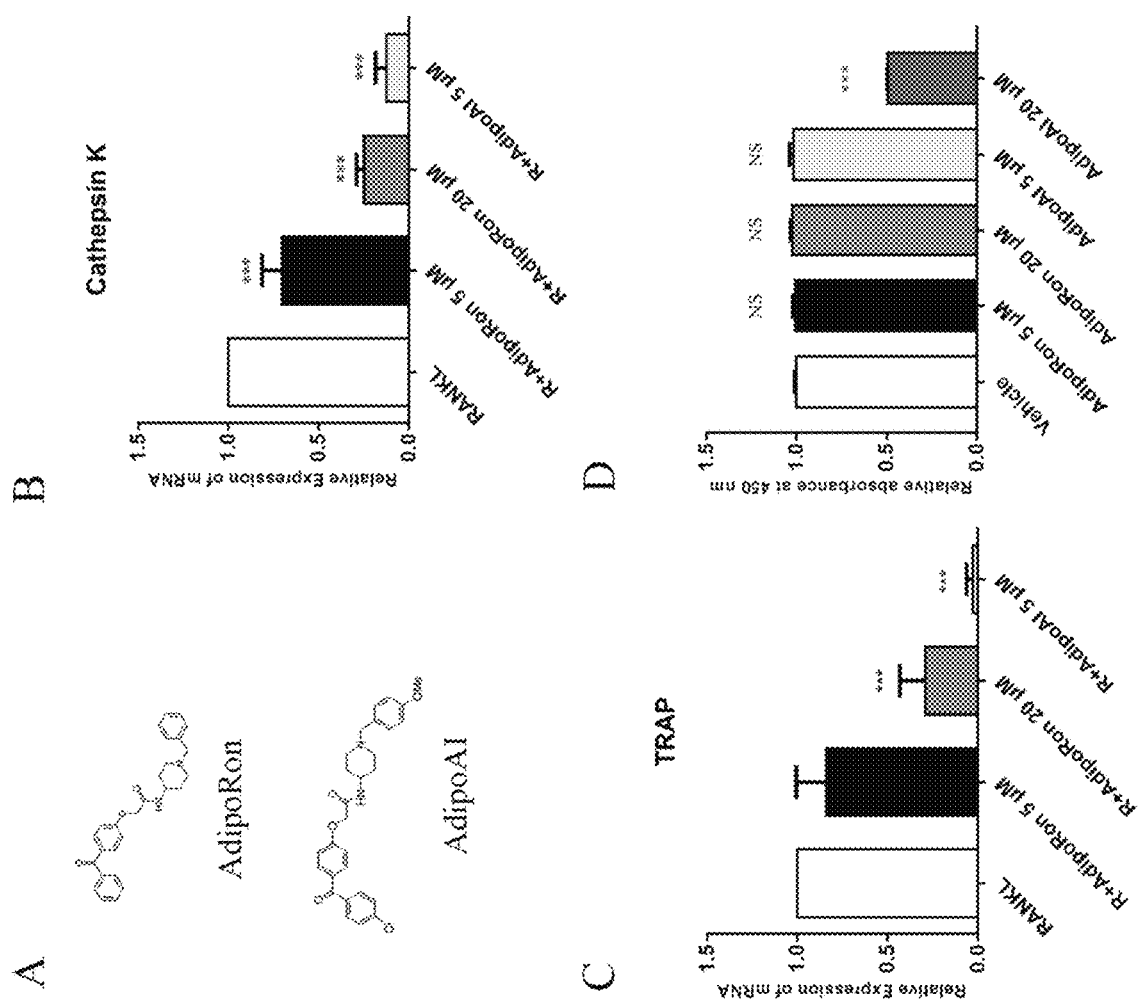
FIG. 18 AdipoRon and AdipoAI inhibit osteoclast differentiation by RAW 264.7 cells. RAW 264.7 cells were treated with receptor activator of nuclear factor κKB ligand (RANKL) (100 ng/ml) for 2 days with or without AdipoRon (20 μM) or AdipoAI (5 μM) for another 2 days. Quantitative reverse transcription polymerase chain reaction (qRT-PCR) analysis of cathepsin K (A) and tartrate-resistant acid phosphatase (TRAP) (B) and messenger RNA (mRNA) expression were calculated (n>3). (C) The CCK-8 analysis of RAW 264.7 cells treated with 20 μM AdipoRon or 5 μM AdipoAI for 48 h. (D) The CCK-8 analysis of RAW 264.7 cells' proliferation at different doses of APR and AdipoAI. Cells were treated with 100 ng/mL RANKL for 2 days with or without AdipoRon (5, 20 μM) or AdipoAI (5, 20 μM) every 2 days for 4 days. (E) Cells were stained with TRAP according to the manufacturer's recommendation (scale bar=100 μm). Data are shown as mean±SD., compared with the vehicle-treated group, *P<0.05. P<0.01. *P<0.001.
Figure 18:
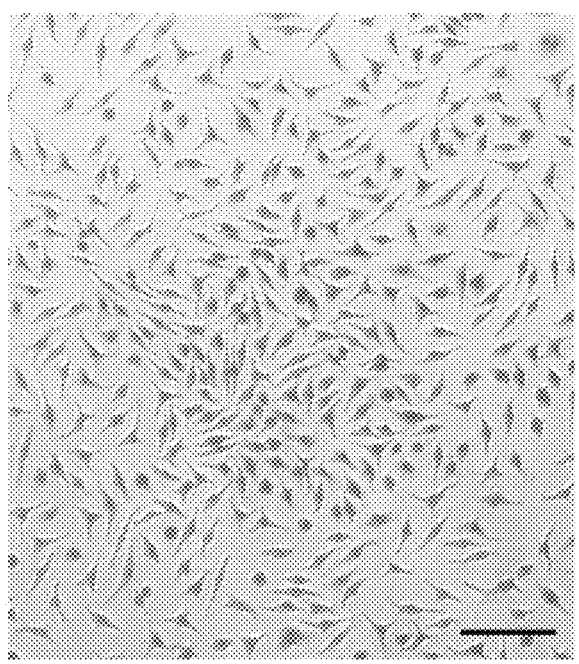
Figure 18:
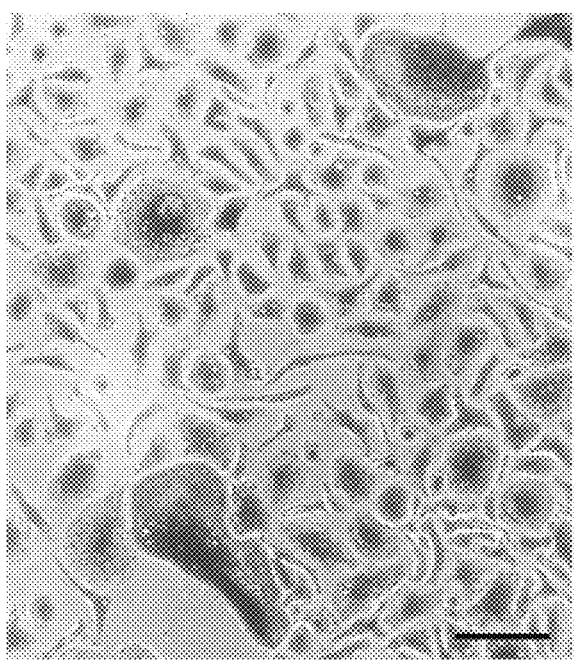
Figure 18:
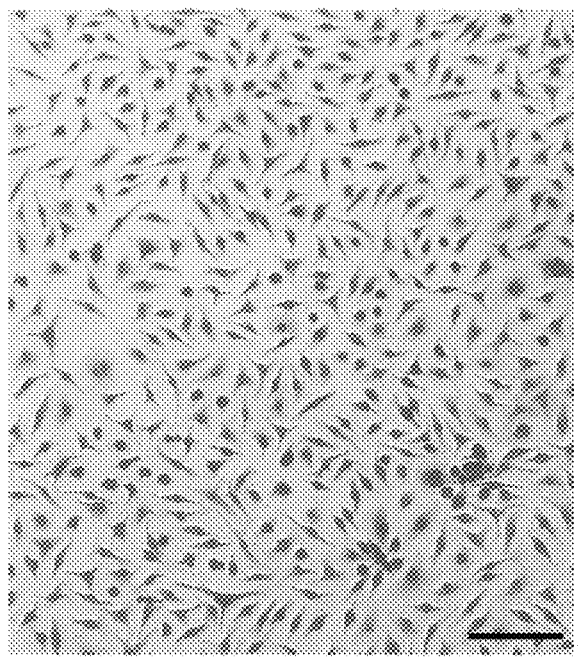
Figure 18:
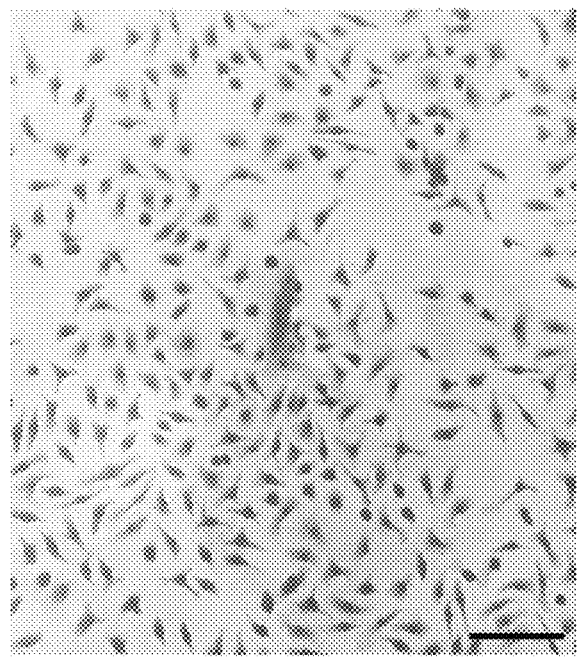

Results from the real-time PCR revealed that treatment with AdipoAI (5 µM) downregulated mRNA expression of the osteoclastogenic markers cathepsin K and TRAP, by 87.5% and 97.0%, respectively, but AdipoRon showed no significant inhibition in TRAP mRNA expression within 5 µM (FIG. 18C) and only displayed a significant inhibition in the cathepsin K (65.1%) and TRAP (64.5%) in treated cells with a higher concentration (20 µM [24]) (FIGS. 18A, B and C). The doses chosen were based on a previous study [25].

The results of the cell viability (CCK-8) assay showed that the co-treatment with 20 µM AdipoRon or 5 µM AdipoAI for 2 days did not reduce the number of RAW 264.7 cells compared with the vehicle-treated group (FIG. 18D). Otherwise, 20 µM AdipoAI reduced cell number (FIG. 18D).

The actions of AdipoRon and AdipoAI in osteoclastogenesis was evaluated. After co-culture with RANKL and AdipoRon (20 µM) and AdipoAI (5 µM) for 6 days, AdipoRon and AdipoAI significantly reduced the number of osteoclast-like cells, compared with RANKL-alone treated group (FIG. 18E).

Figure 19:
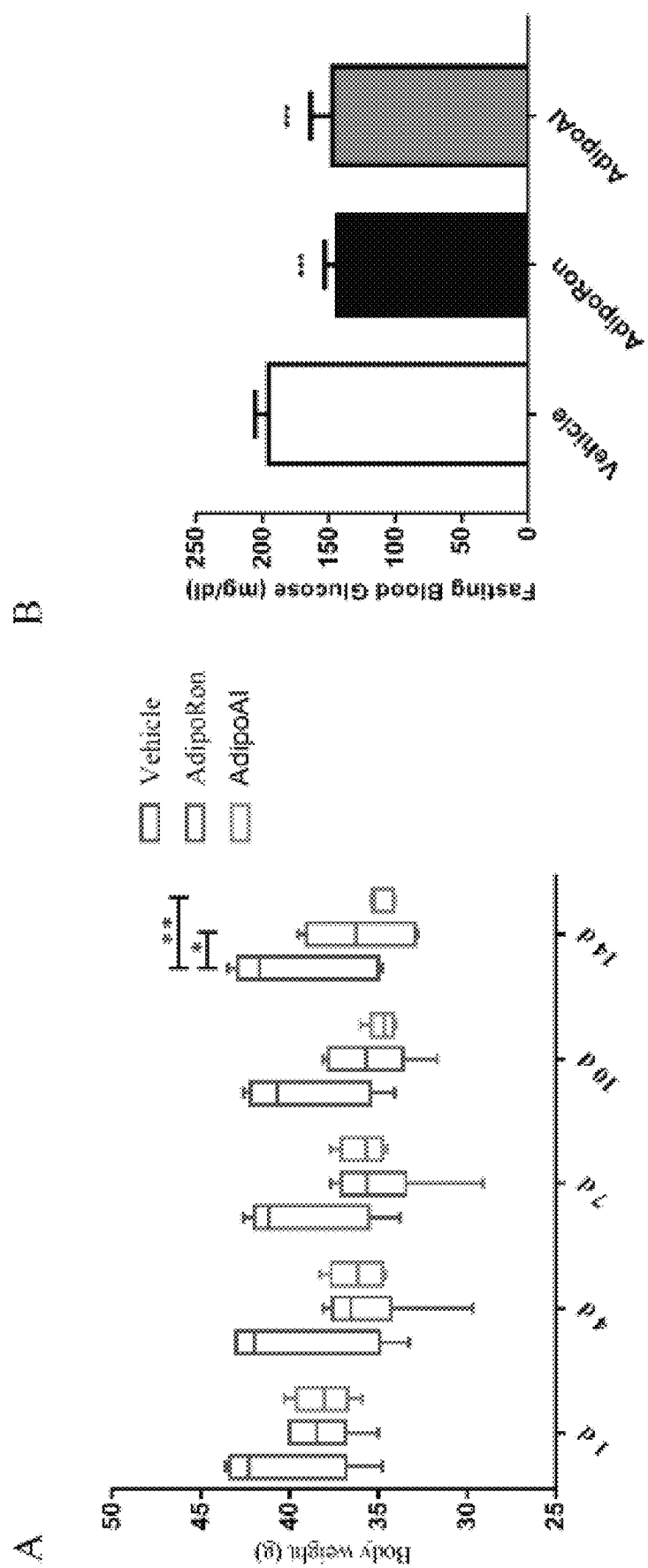
FIG. 19 AdipoRon and AdipoAI attenuate experimental periodontitis in diet-induced obesity (DIO). (A) Bodyweight of vehicle, AdipoRon and AdipoAI-treated DIO mice with experimental periodontitis. (B) Fasting blood glucose in DIO mice with experimental periodontitis treated with vehicle, AdipoRon and AdipoAI. (C) A representative 3-dimensional model of alveolar bone in DIO mice with experimental periodontitis. The red line shows the alveolar bone crest (ABC) and the distance from ABC to the cementoenamel junction (CEJ) on the buccal and palatal sites. The distance from ABC to CEJ in four groups is shown in (D) (n≥7). (E) Representative TRAP-stained alveolar bone in DIO mice with experimental periodontitis. Black arrow, osteoclast (scale bar=200 μm). The number of osteoclasts attached to the alveolar bone surface was calculated (F). (G) Relative expression of IL-6 and CCL2 genes in gingival tissue from DIO mice with experimental periodontitis was analyzed using real-time PCR. The animals were treated AdipoRon and AdipoAI or vehicle alone (n≥5). Data are shown as mean±SD., compared with the vehicle-treated group, *P<0.05. P<0.01. *P<0.001.
Figure 19:
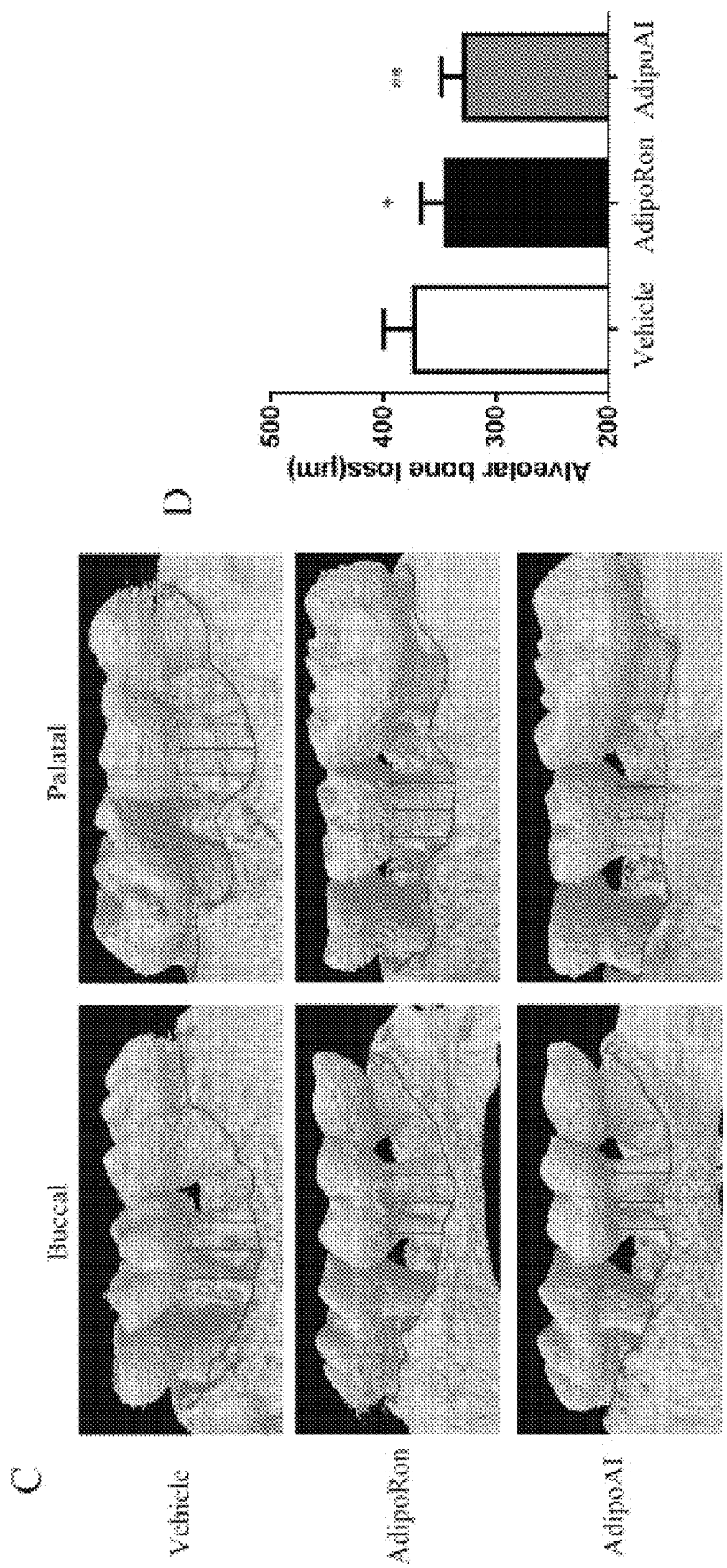
Figure 19:
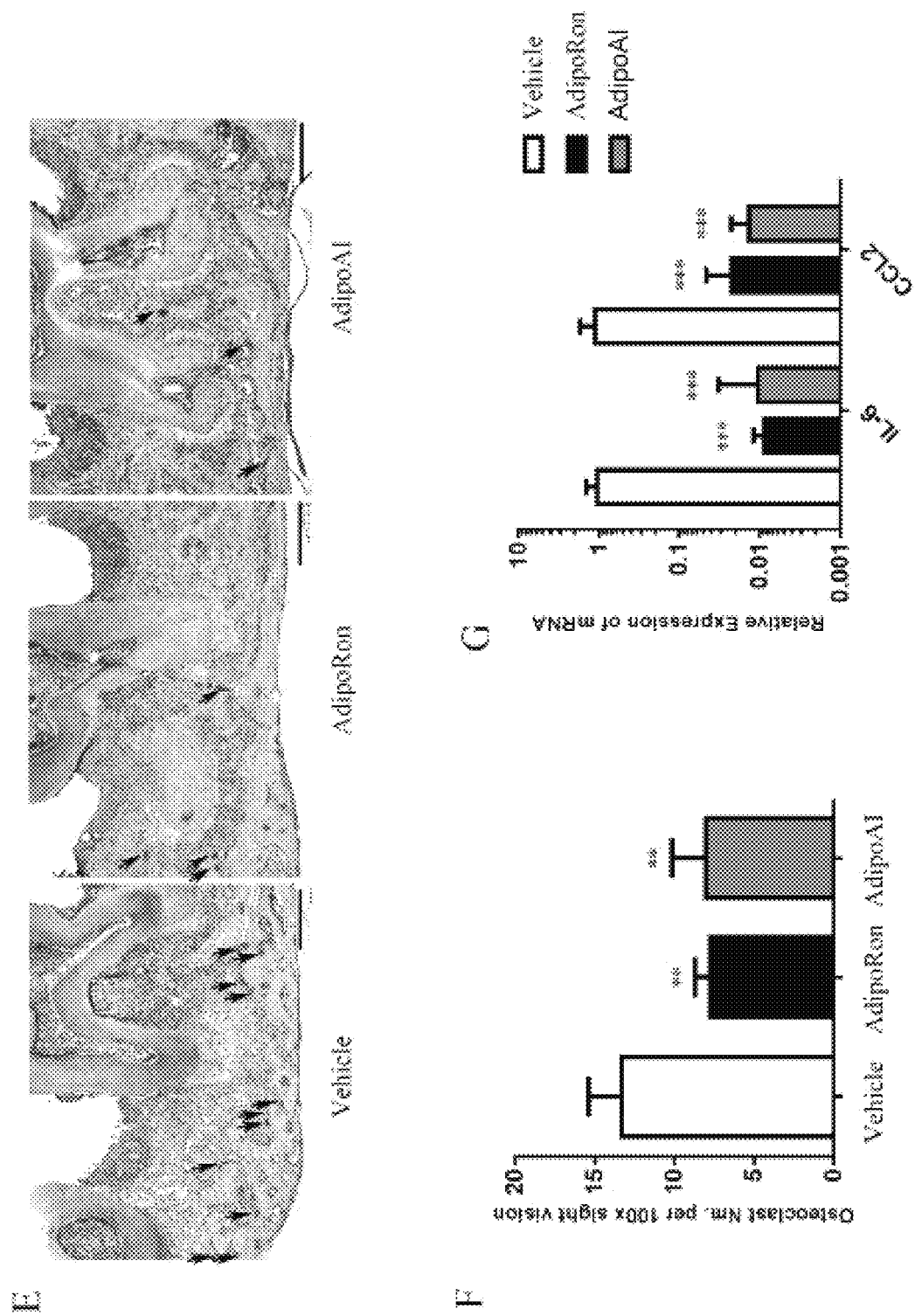

Impact of AdipoAI on Fasting Blood Glucose and Experimental Periodontitis in DIO Mice To emulate the T2D-associated periodontitis and alveolar bone destruction, experimental periodontitis was induced in DIO mice for 2 weeks with simultaneous oral gavage with AdipoRon and AdipoAI. The bodyweight of the animals treated with AdipoRon and AdipoAI decreased significantly during the two weeks treatment compared with the vehicle-treated group (FIG. 19A). In addition, fasting blood glucose levels of DIO mice were tested. The results revealed a significant decrease in fasting blood glucose level (by 73.3% and 75.3% in AdipoRon and AdipoAI-treated mice, respectively) when compared with vehicle-treated group (FIG. 19B).

Further, these results showed that the average alveolar bone loss at 6 sites was 372.3±27.3 µm in vehicle-treated DIO mice, and 344.5±22.2 µm, 328.5±19.9 µm in mice treated with AdipoRon and AdipoAI treated DIO mice, respectively (FIG. 19C, D). Furthermore, TRAP-stained alveolar bone samples showed significantly decreased numbers of osteoclasts in the AdipoRon and AdipoAI-treated DIO mice compared to vehicle-treated DIO mice (FIG. 19E, F). Next, the inflammatory markers IL-6 and CCL-2 were analyzed in the periodontal epithelium, and results showed that AdipoRon and AdipoAI significantly attenuated the IL-6 and CCL-2 gene expression when compared to the vehicle-treated group (FIG. 19G).

AdipoAI Promotes RANKL-Inhibited Autophagy in High Glucose Medium

To evaluate the actions of AdipoAI in hyperglycemia in vitro, cells were cultured in high glucose medium (25 mM). In high glucose medium, RANKL increased mRNA expression of the osteoclastogenesis markers Cathepsin K (FIG. 20A) and TRAP (FIG. 20B) in RAW 264.7 cells. AdipoRon (20 µM) and AdipoAI (5 µM) decreased the RANKL-induced mRNA expression of osteoclastogenesis markers (FIG. 20A, B).

Figure 20:
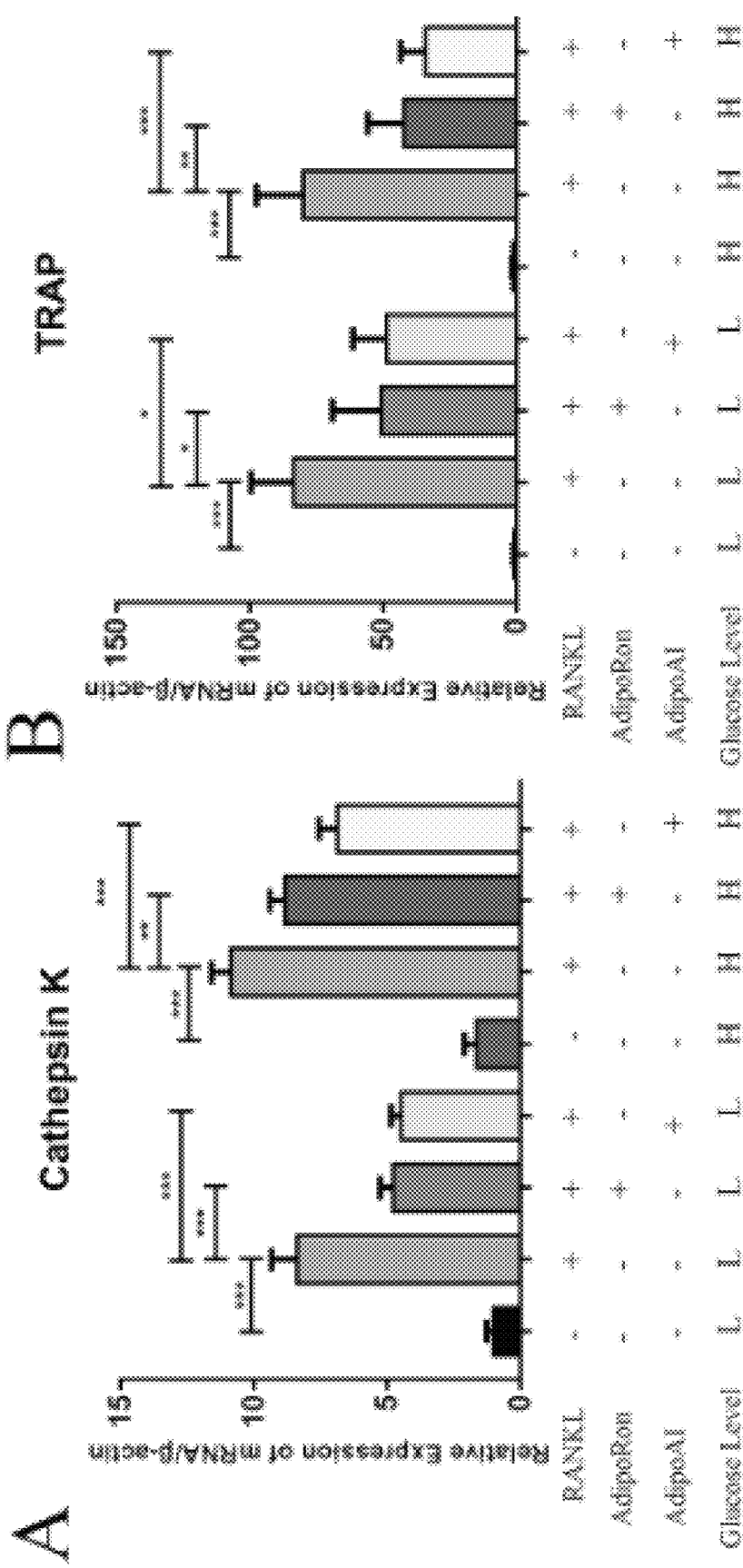
FIG. 20 RAW 264.7 cells were treated with RANKL (100 ng/ml) with or without AdipoRon (20 μM) or AdipoAI (5 μM) in low (5 mmol/l) glucose, 20 mmol/l D-mannitol or high (25 mmol/l) glucose medium. qRT-PCR analysis of cathepsin K (A), TRAP (B) and microtubule associated protein 1 light chain 3 (LC3) (C), and mRNA expression were calculated (n≥3). (D) Western blot analysis of LC3A/B protein levels normalized to β-actin. (E) The mean of protein/β-actin ratios normalized to 1.0 (RANKL-AdipoRon-AdipoAI-H group) quantified by densitometry. (F) Autophagosome images obtained with laser confocal microscopy after the RAW 264.7 cells were transfected with a GFP-LC3 plasmid and treated with RANKL and AdipoRon or AdipoAI (scale bar=50 μm). Data are shown as mean±SD. *, P<0.05. P<0.01. *P<0.001.
Figure 20:
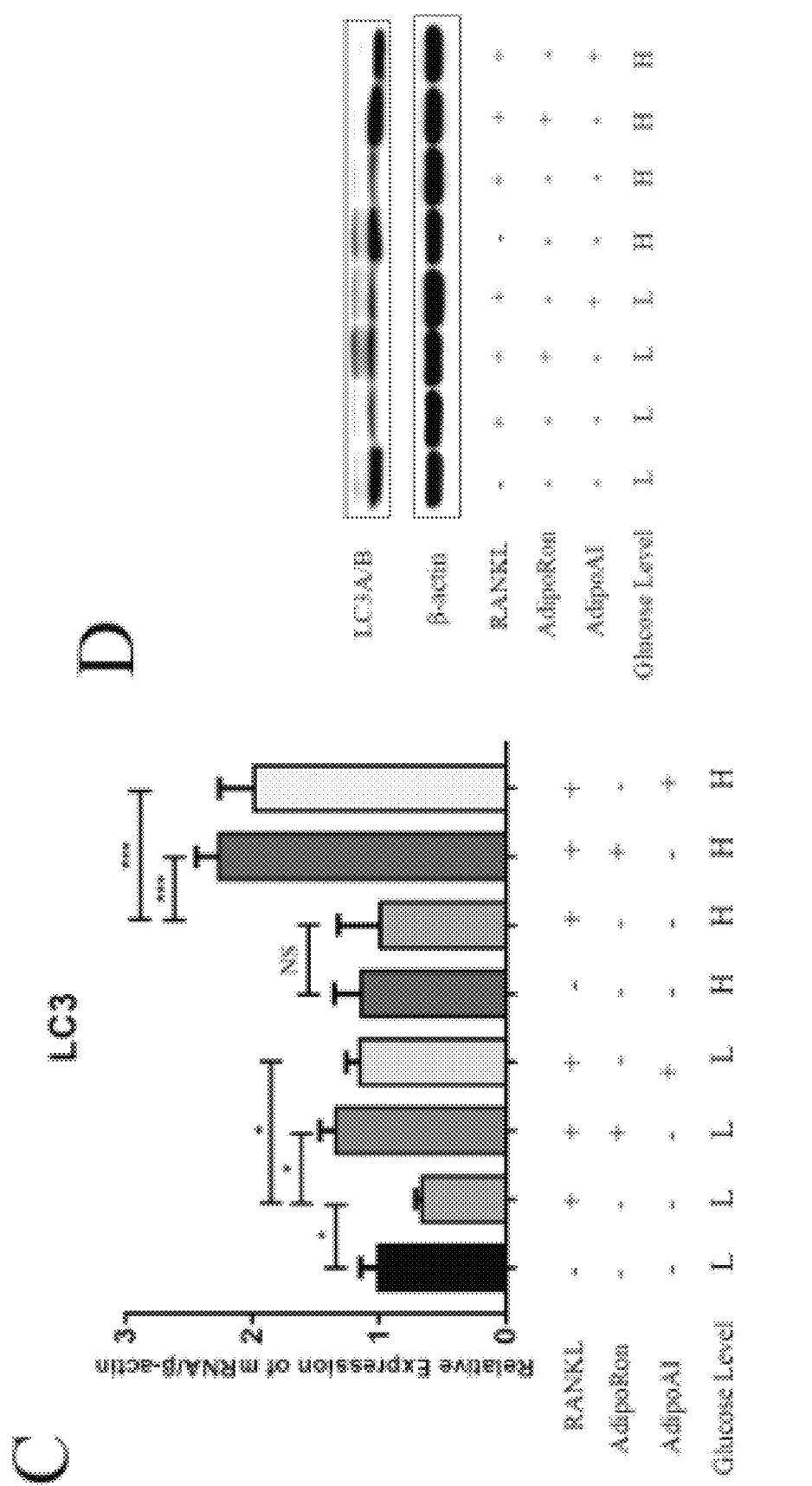
Figure 20:
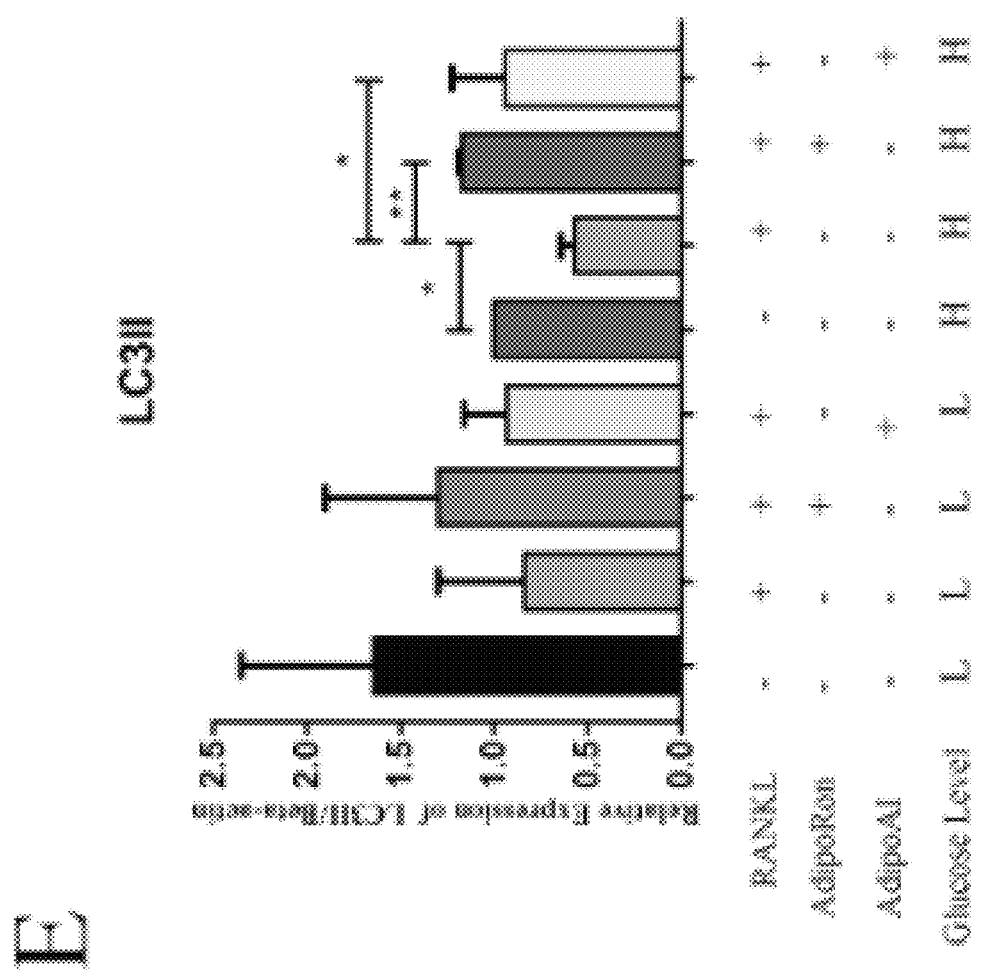
Figure 20:
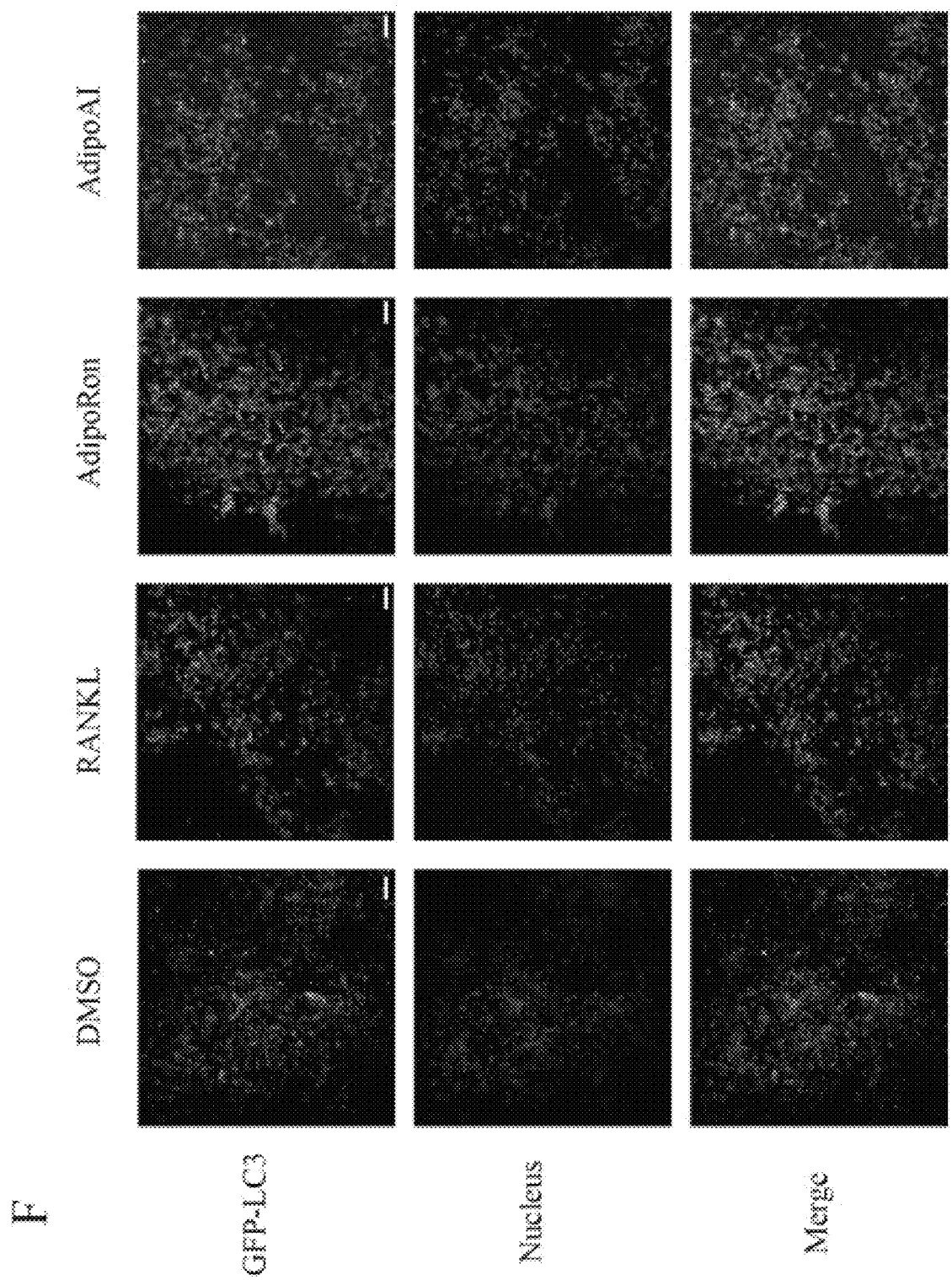

In addition, in high glucose medium, the protein expression of LC3II was inhibited by RANKL stimulation (FIG. 20D, E), but with no significant difference in mRNA expression (FIG. 20C). Moreover, AdipoRon and AdipoAI increased the mRNA expression of LC3, protein expression of LC3II and LC3 puncta (FIG. 20F) by RAW 264.7 cells in high glucose medium with RANKL.

Figure 21:
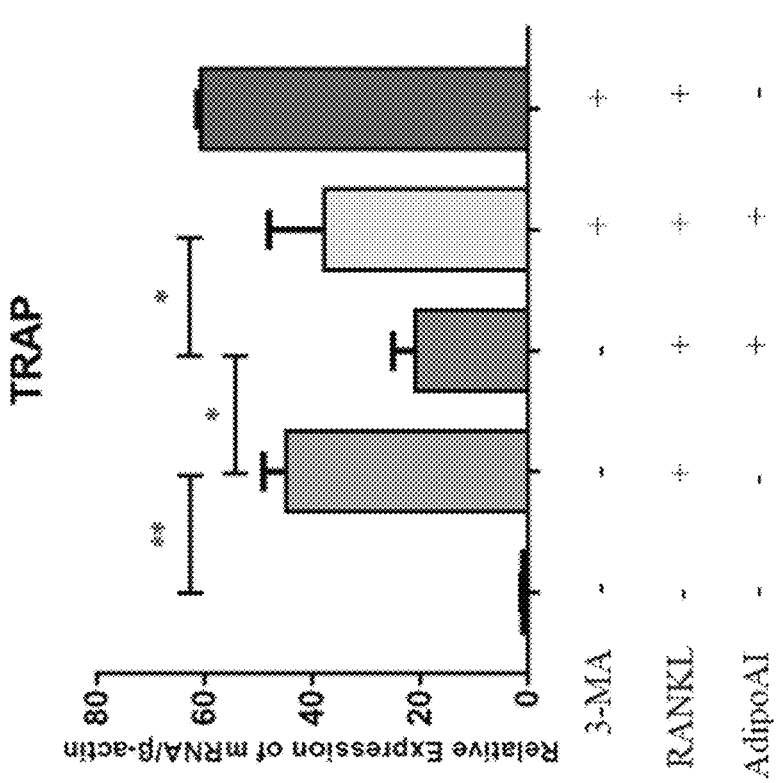
FIG. 21 Autophagy inhibitor reverses AdipoAI-inhibited osteoclastogenesis in high glucose medium. RAW 264.7 cells were treated with RANKL (100 ng/ml) in 2 days and with or without AdipoAI (5 μM) for 24 hours followed by 3-methyladenine (3-MA, 2.5 mM) treatment for another 24 hours in high glucose medium. qRT-PCR analysis of cathepsin K (A), TRAP (B) and LC3 (C) mRNA expression were calculated (n≥3). (D) Western blot analysis of LC3A/B protein levels normalized to β-actin. (E) The mean of protein/β-actin ratios normalized to 1.0 (3-MA-, RANKL-, AdipoAI- group) quantified by densitometry. Data are shown as mean±SD. *, P<0.05. P<0.01. *P<0.001.
Figure 21:
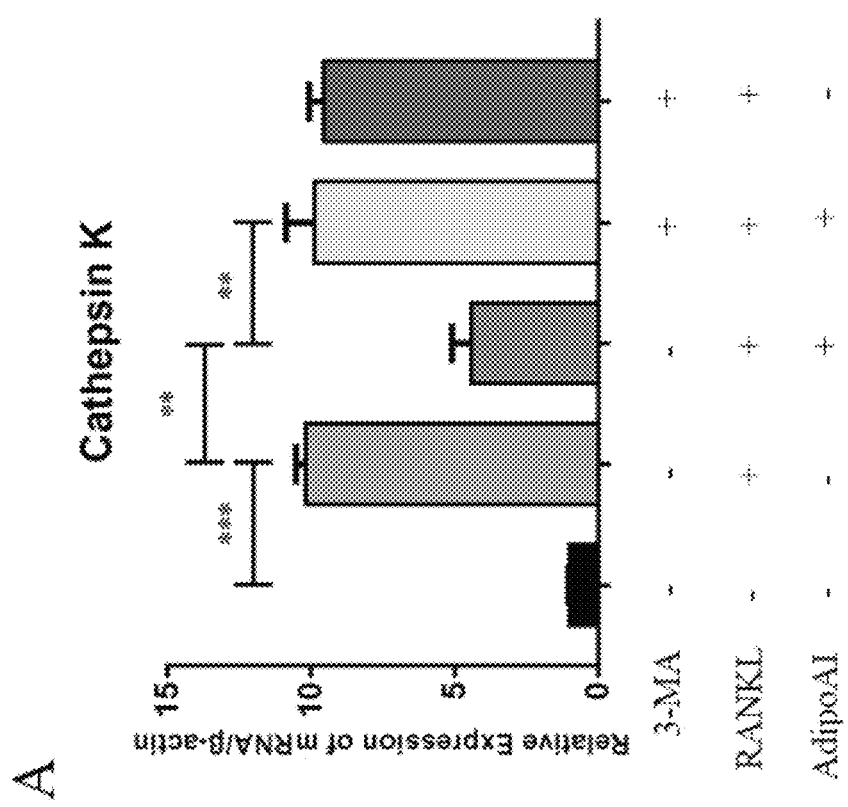
Figure 21:
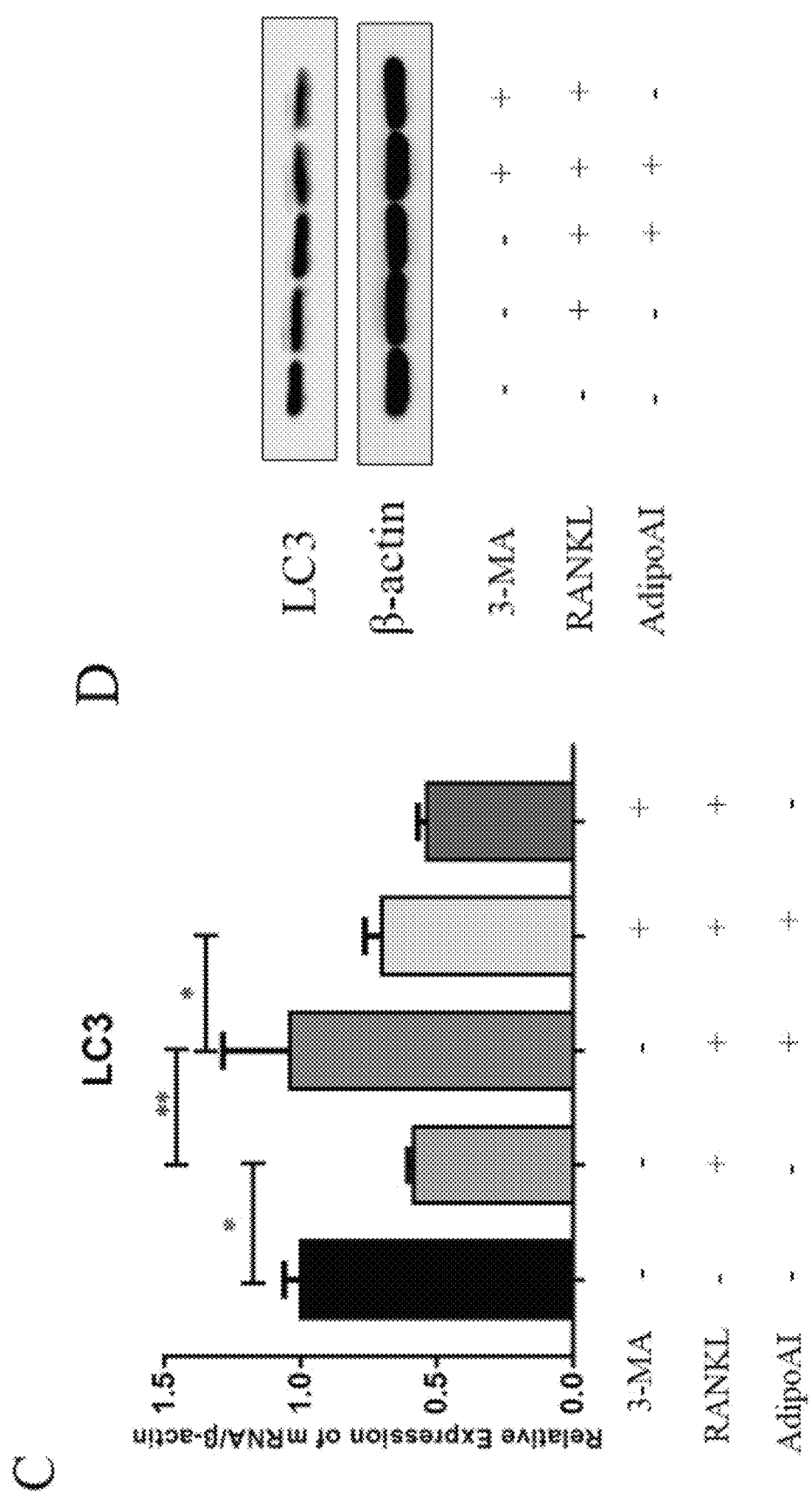
Figure 21:
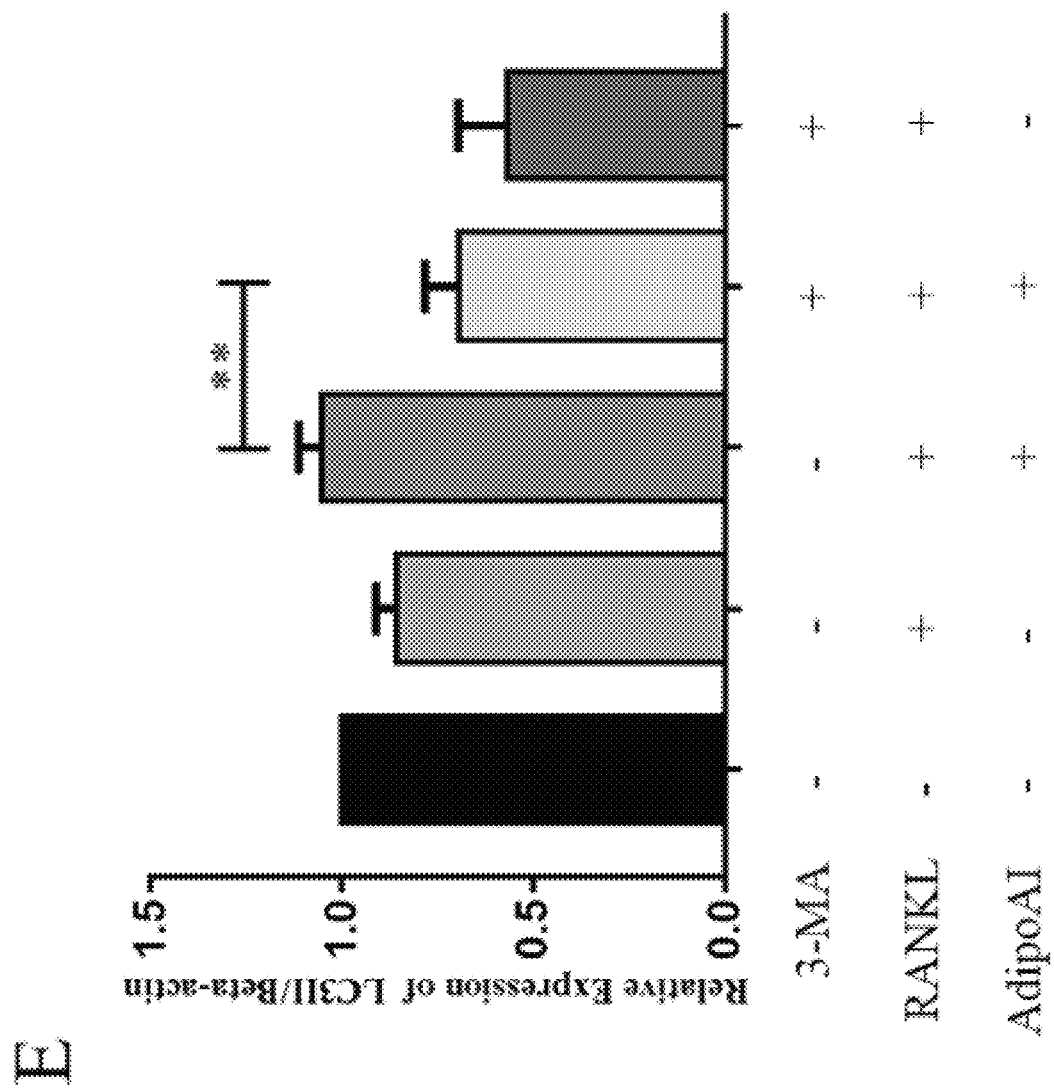

Autophagy Inhibition Reverses the AdipoAI-Induced Inhibition of Osteoclastogenesis in High Glucose Medium The autophagy inhibitor, 3-methyladenine, decreased the mRNA expression of LC3 and protein expression of LC3II induced by AdipoAI (FIG. 21C-E). In addition, 3-methyladenine reversed the AdipoAI-inhibited mRNA expression of osteoclastogenesis markers Cathepsin K and TRAP in high glucose medium (FIG. 21A, B).

AdipoAI-Induced Autophagy of Osteoclasts in High Glucose Medium via the Akt1/mTOR Signaling Pathway.

Figure 22:
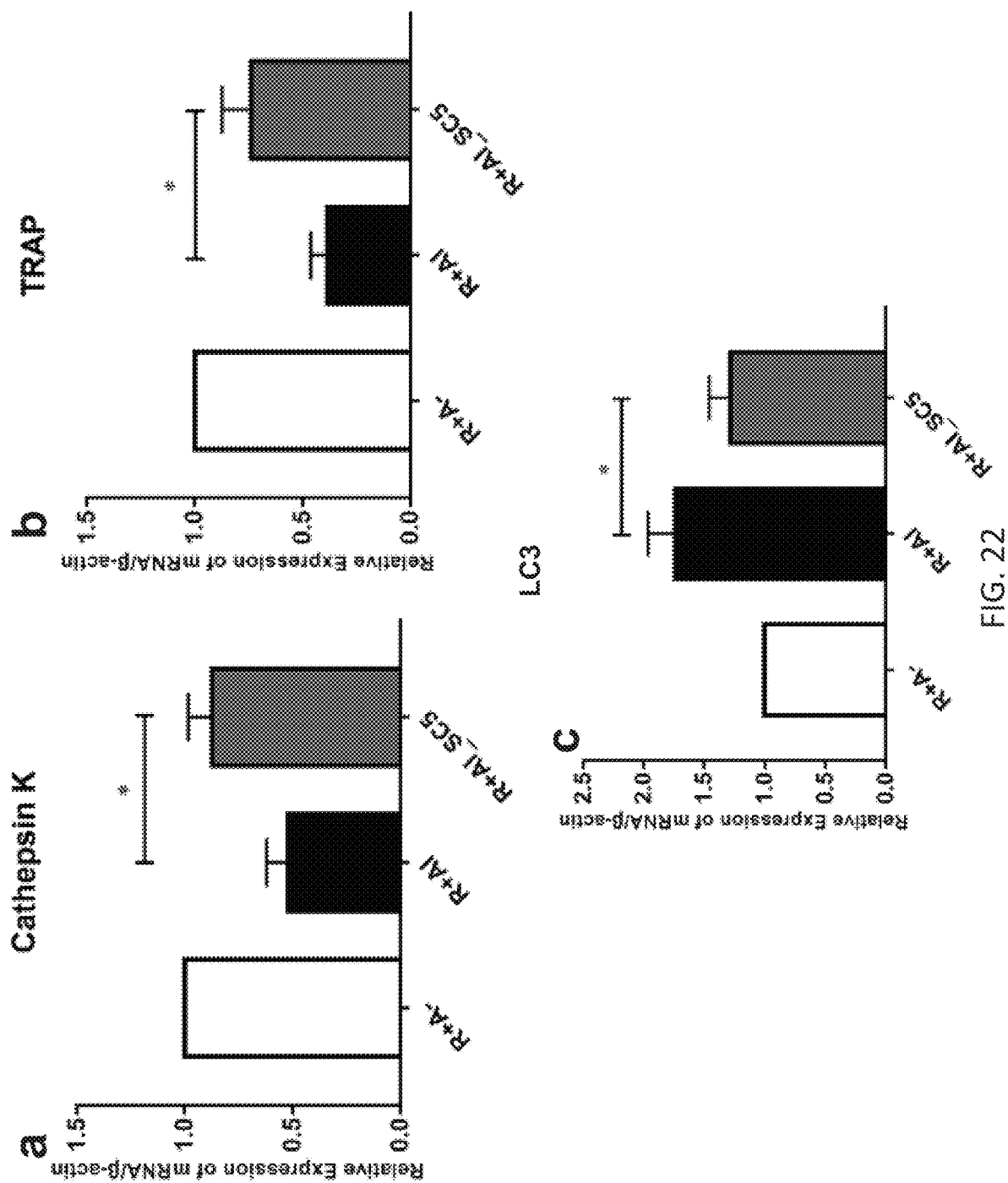
FIG. 22 AdipoAI-induced autophagy of osteoclasts in high glucose medium via AKT1/mTOR signaling pathway. RAW 264.7 cells were induced with RANKL for 2 days and then treated with or without (5 μM) additional 24 hours after serum starvation for 4 hours. Then, the cells were treated with RANKL, AdipoAI or SC79 (5 μM), an AKT activator, for another 24 hours in high glucose medium. qRT-PCR analysis of mRNA expression of cathepsin K (A), TRAP (B) and LC3 (C) were calculated (n≥3). (D) Representative images show the protein expression levels of AKT, p-AKT, AKT1, p-AKT1, mTOR, p-mTOR, and LC3A/B in osteoclasts. Quantitative analysis of bands is shown in (E-K) (n≥3). Data are shown as mean±SD. *, P<0.05. P<0.01. *P<0.001. R: RANKL. A, AI: AdipoAI. SC5: SC79 (5 μM).
Figure 22:
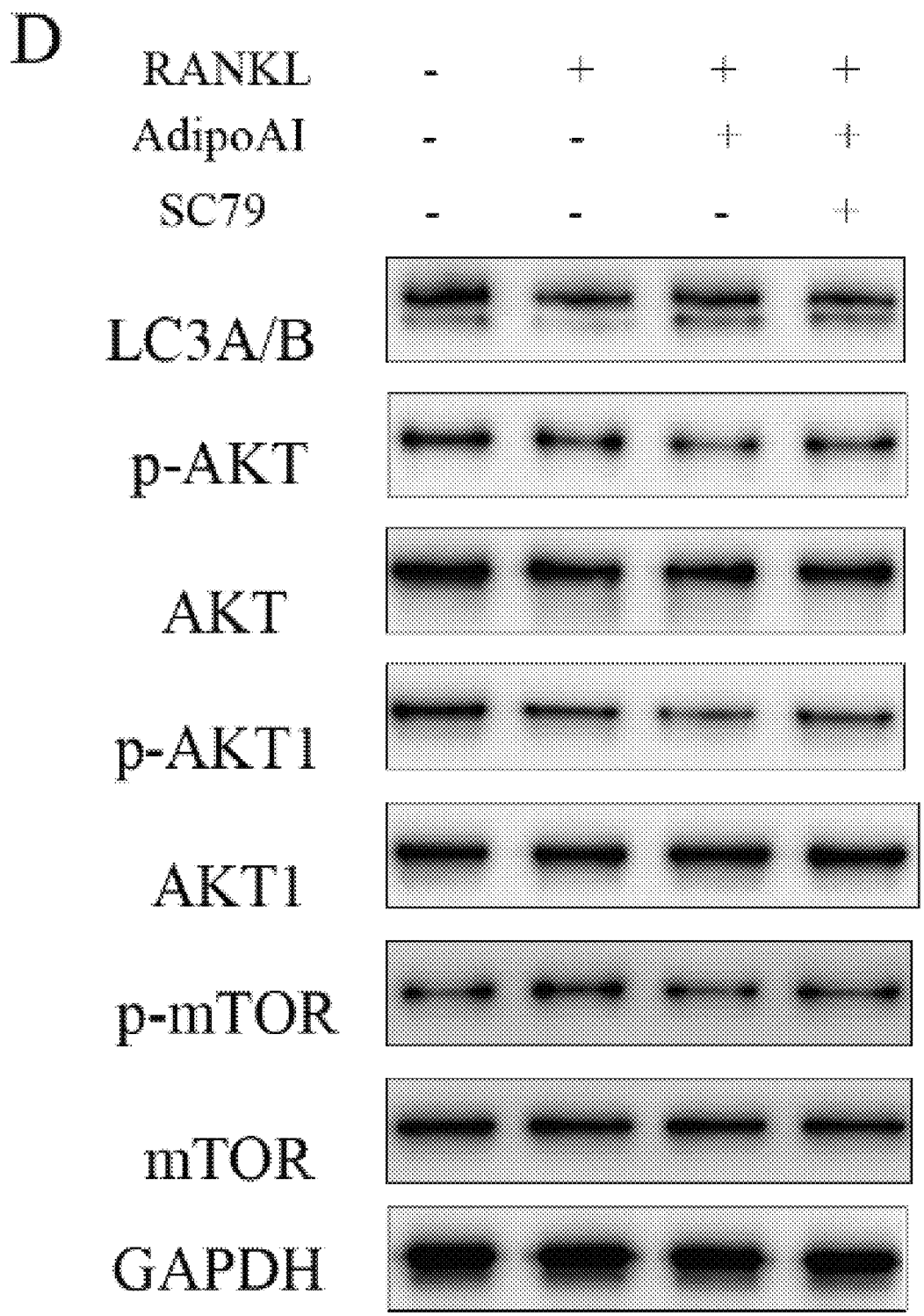
Figure 22:
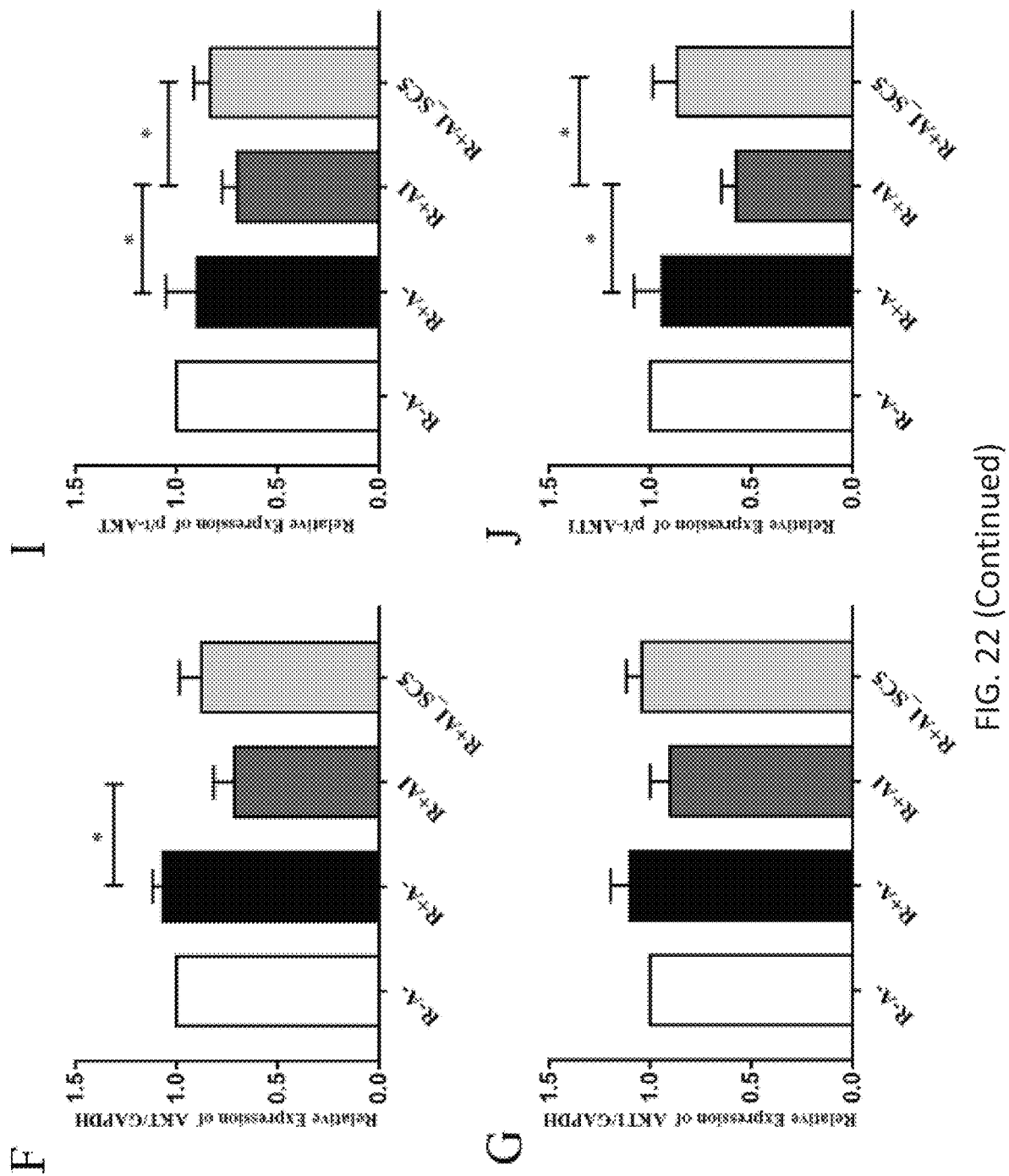
Figure 22:
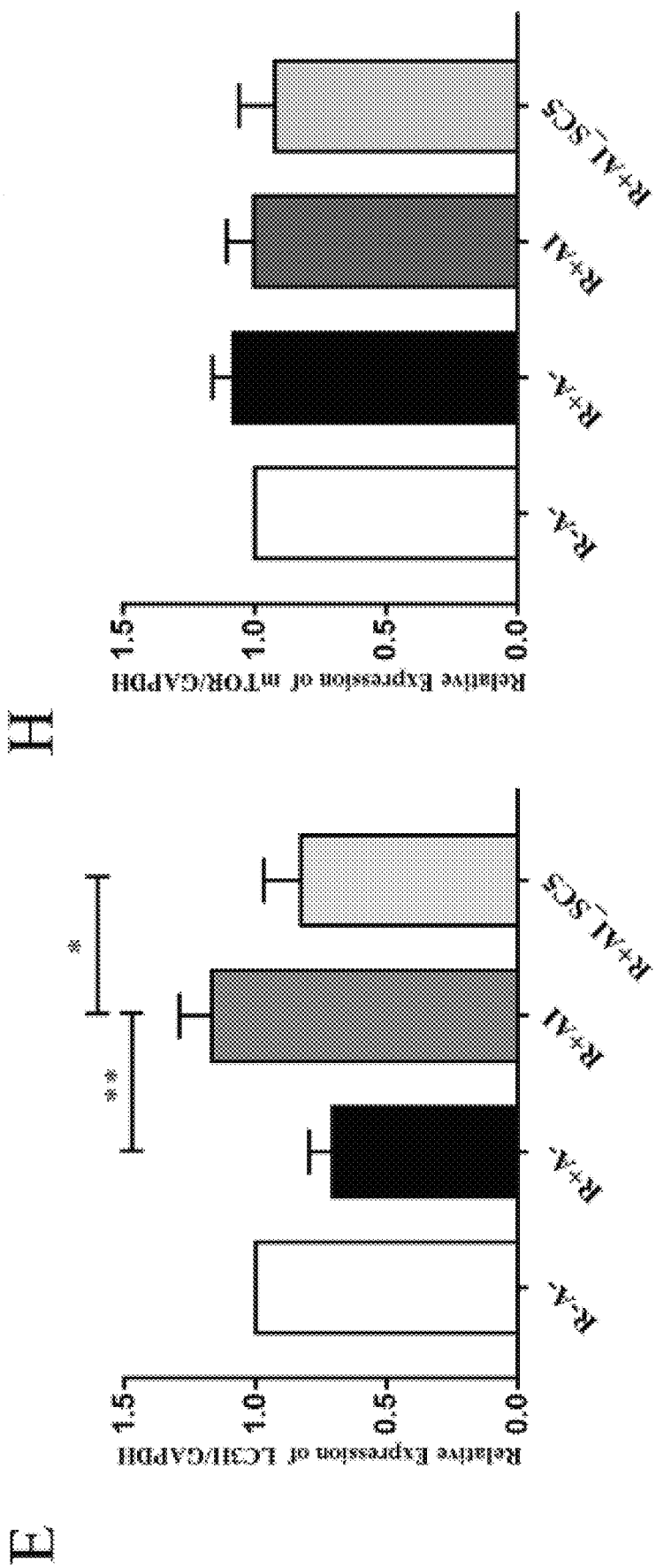
Figure 22:
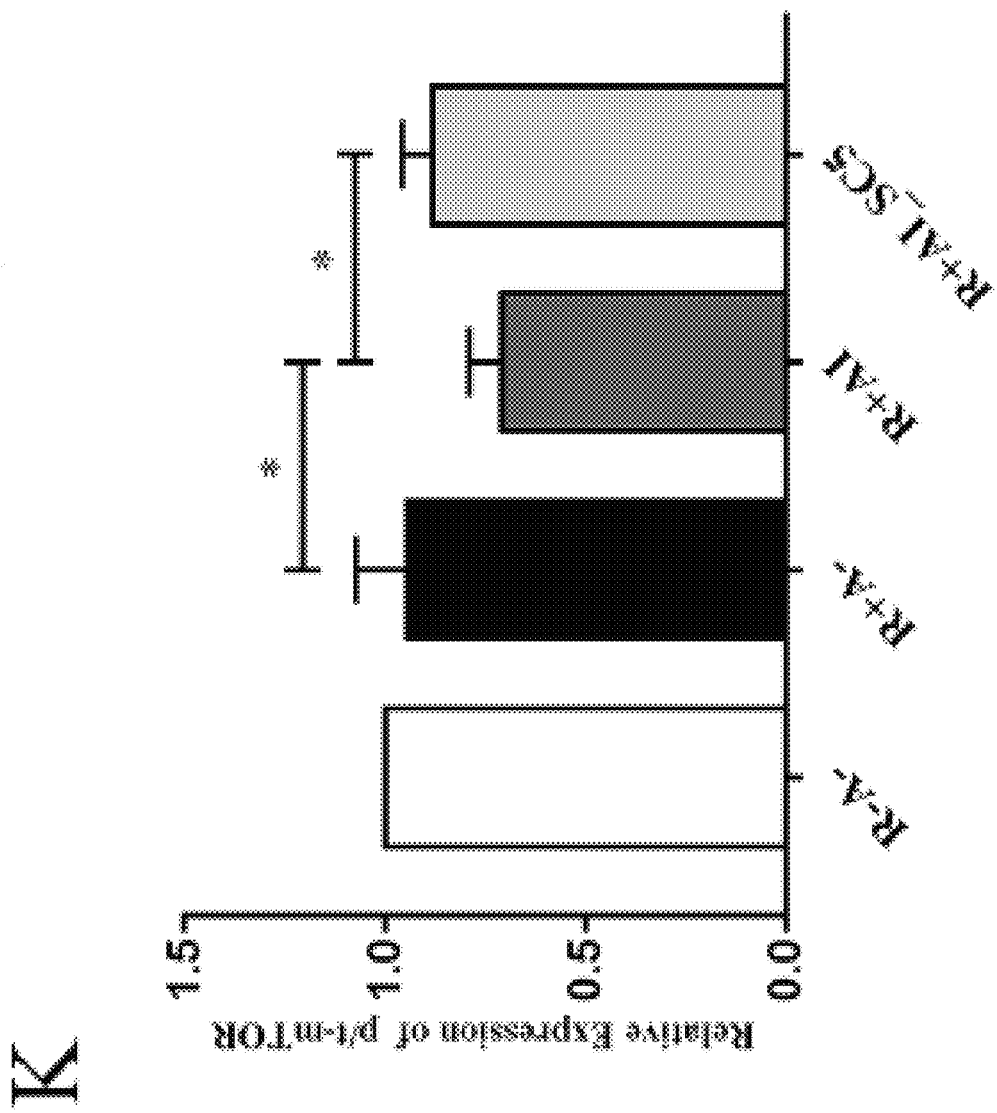

To investigate whether AdipoAI-induced autophagy was related to the AKT signaling pathway, SC79, an AKT activator, was used to evaluate the actions of AdipoAI on osteoclast autophagy and osteoclastogenesis in high glucose medium. To investigate whether SC79 impacts RANKL-induced osteoclastogenesis, qRT-PCR was performed. As shown in FIG. 22A-C, SC79 reverses the upregulated expression of LC3 mRNA and downregulated expression of osteoclastogenic markers including Cathepsin K and TRAP. The phosphorylation of AKT1/mTOR signaling related protein factors was investigated, including AKT, AKT1 and mTOR, in response to RANKL with or without AdipoAI and SC79 treatment in RAW 264.7 cells (FIG. 22D). AdipoAI promotes the expression of LC3II, inhibits the expression of AKT, and reduces the phosphorylation of AKT, AKT1 and mTOR by 21%, 40% and 25%, respectively. Furthermore, SC79 reverses the promoted expression of LC3II, decreases expression of AKT, and reduces phosphorylation of AKT, AKT1 and mTOR induced by AdipoAI (FIG. 22E-K).

DISCUSSION

AdipoRon, an adiponectin receptor agonist, is a potential therapeutic molecule that has shown promise in attenuating diabetes-related complications, such as cardiovascular disease [29], kidney disease [30], and periodontal disease [24] in animal models. However, the low binding affinity for AdipoRs and relatively low solubility limited its clinical application [23]. The impact of a novel adiponectin receptor agonist AdipoAI on T2D-associated periodontitis was evaluated. It was found that AdipoAI was effective in inhibiting osteoclast differentiation and attenuating experimental periodontitis in DIO mice by promoting autophagy in osteoclasts.

These results demonstrated the anti-osteoclastogenic actions of AdipoRon both in low and high level glucose medium in vitro. It was also confirmed that AdipoAI exhibits anti-osteoclastogenic actions without affecting the cell viability at an effective dosage.

Treatment of DIO mice with AdipoAI and AdipoRon led to a significant decrease in body weight, fasting blood glucose level, which were in agreement of previous study that AdipoRon could alleviate body weight, blood glucose tolerance and insulin sensitivity in diabetic db/db mice due to the improvement of diabetes control [23]. In addition, the two chemicals were also capable of decreasing alveolar bone loss, osteoclast number and inhibiting the expression of inflammatory markers in the periodontium of DIO animals.

Autophagy is a major protective mechanism allowing cell survival in response to multiple stressors, including nutrient deprivation, growth factor depletion, infection, and hypoxia [31,32]. It has been shown that dysfunction of autophagy is involved in loss of bone [22]. A series of studies have reported on the induction of autophagy by adiponectin in different tissues and cells and on the protective effects of adiponectin mediated by improving autophagy [33-35]. Nevertheless, few publications have studied adiponectin in osteoclastogenesis via autophagy, nor are there any reports of the impact the recently synthesized adiponectin receptor agonists, AdipoRon nor AdipoAI on autophagy. LC3 mRNA and LC3II and LC3 puncta protein expression during osteoclastogenesis induced by RANKL with or without AdipoAI or AdipoRon treatment was observed. AdipoAI and AdipoRon promoted autophagy, and also negatively regulated osteoclast formation. The downregulation of the AKT1/mTOR signaling pathway was mediated by AdipoAI actions in autophagy induced anti-osteoclastogenesis, which is consistent with previous studies that show that Adiponectin inhibits osteoclastogenesis via suppression of Akt1 [36] and induction of autophagy (via mTOR inhibition, rapamycin) negatively regulates both osteoclast formation and activity from osteoclast precursor cells [37-39].

Whether reduction of food intake or decreased inflammation was responsible for the reduction of body weight could not be determined.

In conclusion, this study demonstrates a role for AdipoAI in attenuating experimental periodontitis in DIO mice. These results reveal that AdipoAI ameliorates experimental periodontitis by inhibiting the production of pro-inflammatory cytokines, osteoclast differentiation, and decreases osteoclast numbers at a lower dosage than AdipoRon via suppression of Akt1/mTOR signaling pathway without side effects.

REFERENCES

1. Nesse W, Dijkstra P U, Abbas F, et al. Increased prevalence of cardiovascular and autoimmune diseases in periodontitis patients: a cross-sectional study. *Journal of periodontology.* 2010; 81(11):1622-1628.

2. Nibali L, Tatarakis N, Needleman I, et al. Association between metabolic syndrome and periodontitis: a systematic review and meta-analysis. *The Journal of Clinical Endocrinology & Metabolism.* 2013; 98(3):913-920.

3. Zhou X, Han J, Liu Z, Song Y, Wang Z, Sun Z. Effects of periodontal treatment on lung function and exacerbation frequency in patients with chronic obstructive pulmonary disease and chronic periodontitis: a 2-year pilot randomized controlled trial. *Journal of clinical periodontology.* 2014; 41(6):564-572.

4. Preshaw P M, Alba A L, Herrera D, et al. Periodontitis and diabetes: a two-way relationship. *Diabetologia.* 2012; 55(1):21-31.

5. Sanz M, Ceriello A, Buysschaert M, et al. Scientific evidence on the links between periodontal diseases and diabetes: Consensus report and guidelines of the joint workshop on periodontal diseases and diabetes by the International Diabetes Federation and the European Federation of Periodontology. *Journal of clinical periodontology.* 2018; 45(2): 138-149.

6. Ainamo J, Lahtinen A, Uitto V J. Rapid periodontal destruction in adult humans with poorly controlled diabetes. A report of 2 cases. *Journal of clinical periodontology.* 1990; 17(1):22-28.

7. Seppala B, Ainamo J. A site-by-site follow-up study on the effect of controlled versus poorly controlled insulin-dependent diabetes mellitus. *Journal of clinical periodontology.* 1994; 21(3):161-165.

8. Sima C, Van Dyke T E. Therapeutic Targets for Management of Periodontitis and Diabetes. *Curr Pharm Des.* 2016; 22(15):2216-2237.

9. Eke P I, Dye B A, Wei L, Thornton-Evans G O, Genco R J, Cdc Periodontal Disease Surveillance workgroup: James Beck GDRP. Prevalence of periodontitis in adults in the United States: 2009 and 2010. *J Dent Res.* 2012; 91(10):914-920.

10. Graves D T, Li J, Cochran D L. Inflammation and uncoupling as mechanisms of periodontal bone loss. *J Dent Res.* 2011; 90(2):143-153.

11. Liu R, Bal H S, Desta T, et al. Diabetes enhances periodontal bone loss through enhanced resorption and diminished bone formation. *J Dent Res.* 2006; 85(6):510-514.

12. Wu Y, Song L T, Li J S, Zhu D W, Jiang S Y, Deng J Y MicroRNA-126 Regulates Inflammatory Cytokine Secretion in Human Gingival Fibroblasts Under High Glucose via Targeting Tumor Necrosis Factor Receptor Associated Factor 6. *J Periodontol.* 2017; 88(11):e179-e187.

13. Tang Y, Sun F, Li X, Zhou Y, Yin S, Zhou X. Porphyromonas endodontalis lipopolysaccharides induce RANKL by mouse osteoblast in a way different from that of Escherichia coli lipopolysaccharide. *Journal of endodontics.* 2011; 37(12):1653-1658.

14. Yin X, Zhou C, Li J, et al. Autophagy in bone homeostasis and the onset of osteoporosis. *Bone research.* 2019; 7:28.

15. Djajadikerta A, Keshri S, Pavel M, Prestil R, Ryan L, Rubinsztein DC. Autophagy Induction as a Therapeutic Strategy for Neurodegenerative Diseases. *J Mol Biol.* 2020; 432(8):2799-2821.

16. Mizushima N. Autophagy: process and function. *Genes Dev.* 2007; 21(22):2861-2873.

17. Wang L, Gao Z, Zhang J, Huo Y, Xu Q, Qiu Y. Netrin-1 regulates ERK1/2 signaling pathway and autophagy activation in wear particle-induced osteoclastogenesis. *Cell Biol Int.* 2021.

18. Pierrefite-Carle V, Santucci-Darmanin S, Breuil V, Camuzard O, Carle G F. Autophagy in bone: Self-eating to stay in balance. *Ageing Res Rev.* 2015; 24(Pt B):206-217.

19. Tong X, Gu J, Song R, et al. Osteoprotegerin inhibit osteoclast differentiation and bone resorption by enhancing autophagy via AMPK/mTOR/p70S6K signaling pathway in vitro. *J Cell Biochem.* 2018.

20. Boyce B F, Xing L. Functions of RANKL/RANK/OPG in bone modeling and remodeling. *Archives of biochemistry and biophysics.* 2008; 473(2):139-146.

21. Li R F, Chen G, Ren J G, et al. The adaptor protein p62 is involved in RANKL-induced autophagy and osteoclastogenesis. *J Histochem Cytochem.* 2014; 62(12):879-888.

22. Montaseri A, Giampietri C, Rossi M, Riccioli A, Del Fattore A, Filippini A. The Role of Autophagy in Osteoclast Differentiation and Bone Resorption Function. *Biomolecules.* 2020; 10(10).

23. Okada-Iwabu M, Yamauchi T, Iwabu M, et al. A small-molecule AdipoR agonist for type 2 diabetes and short life in obesity. *Nature.* 2013; 503(7477):493-499.

24. Wu X, Qiu W, Hu Z, et al. An Adiponectin Receptor Agonist Reduces Type 2 Diabetic Periodontitis. *J Dent Res.* 2019; 98(3):313-321.

25. Qiu W, Wu H, Hu Z, et al. Identification and characterization of a novel adiponectin receptor agonist adipo anti-inflammation agonist and its anti-inflammatory effects in vitro and in vivo. *British journal of pharmacology.* 2021; 178(2):280-297.

26. Lian J, Wu X, Liu Y, et al. Potential roles of miR-335-5p on pathogenesis of experimental periodontitis. *J Periodontal Res.* 2020; 55(2):191-198.

27. Li R, Sun J, Yang F, et al. Effect of GARP on osteogenic differentiation of bone marrow mesenchymal stem cells via the regulation of TGFbeta1 in vitro. *PeerJ.* 2019; 7:e6993.

28. Chen J F, Wu P, Xia R, et al. STAT3-induced lncRNA HAGLROS overexpression contributes to the malignant progression of gastric cancer cells via mTOR signal-mediated inhibition of autophagy. *Mol Cancer.* 2018; 17(1):6.

29. Zhang Y, Zhao J, Li R, et al. AdipoRon, the first orally active adiponectin receptor activator, attenuates postischemic myocardial apoptosis through both AMPK-mediated and AMPK-independent signalings. *Am J Physiol Endocrinol Metab.* 2015; 309(3):E275-282.

30. Kim Y, Lim J H, Kim M Y, et al. The Adiponectin Receptor Agonist AdipoRon Ameliorates Diabetic Nephropathy in a Model of Type 2 Diabetes. *J Am Soc Nephrol.* 2018; 29(4):1108-1127.

31. Dikic I, Elazar Z. Mechanism and medical implications of mammalian autophagy. *Nat Rev Mol Cell Biol.* 2018; 19(6):349-364.

32. Hansen M, Rubinsztein D C, Walker D W. Autophagy as a promoter of longevity: insights from model organisms. *Nat Rev Mol Cell Biol.* 2018; 19(9):579-593.

33. Xu A, Sweeney G. Emerging role of autophagy in mediating widespread actions of ADIPOQ/adiponectin. *Autophagy.* 2015; 11(4):723-724.

34. Liu Y, Palanivel R, Rai E, et al. Adiponectin stimulates autophagy and reduces oxidative stress to enhance insulin sensitivity during high-fat diet feeding in mice. *Diabetes.* 2015; 64(1):36-48.

35. Ahlstrom P, Rai E, Chakma S, Cho H H, Rengasamy P, Sweeney G. Adiponectin improves insulin sensitivity via activation of autophagic flux. *J Mol Endocrinol.* 2017; 59(4):339-350.

36. Tu Q, Zhang J, Dong L Q, et al. Adiponectin inhibits osteoclastogenesis and bone resorption via APPL1-mediated suppression of Akt1. *J Biol Chem.* 2011; 286(14): 12542-12553.

37. Hocking L J, Whitehouse C, Helfrich M H. Autophagy: a new player in skeletal maintenance? *Journal of bone and mineral research: the official journal of the American Society for Bone and Mineral Research.* 2012; 27(7): 1439-1447.

38. Sanchez C P, He Y Z. Bone growth during rapamycin therapy in young rats. *BMC Pediatr.* 2009; 9:3.

39. Smink J J, Tunn P U, Leutz A. Rapamycin inhibits osteoclast formation in giant cell tumor of bone through the C/EBβ—MafB axis. *J Mol Med (Berl).* 2012; 90(1):25-30.

We claim:

1. A compound of formula

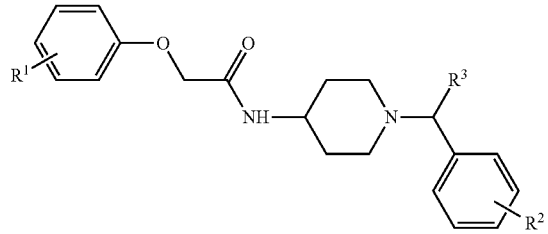

or a pharmaceutically acceptable salt thereof, wherein $R^1$ is —C(=O)$R^4$; $R^4$ is a halo-substituted phenyl, an unsubstituted phenyl, or a $C_1$-$C_4$ alkyl; $R^2$ is a $C_1$-$C_4$ alkoxyl, hydrogen, or a halo; and $R^3$ is hydrogen or a $C_1$-$C_4$ alkyl; or wherein $R^1$ is an unsubstituted phenyl; $R^2$ is a $C_1$-$C_4$ alkoxyl or hydrogen; and $R^3$ is hydrogen or a $C_1$-$C_4$ alkyl; and wherein if $R^1$ is —C(=O)$R^4$ and $R^4$ is a 4-chloro substituted phenyl, $R^2$ and $R^3$ are not both hydrogen;

if $R^1$ is —C(=O)$R^4$ and $R^4$ is the unsubstituted phenyl, (i) $R^2$ and $R^3$ are not both hydrogen or (ii) $R^2$ and $R^3$ are not respectively 4-chloro and hydrogen;

if $R^1$ is —C(=O)$R^4$ and $R^4$ is methyl, $R^2$ and $R^3$ are not respectively 3,4-dichloro and hydrogen, 3,4-dichloro and hydrogen, or 4-bromo and hydrogen;

if $R^1$ is —C(=O)$R^4$ and $R^4$ is ethyl, $R^2$ and $R^3$ are not respectively 3,4-dichloro and hydrogen; and if $R^1$ is phenyl, $R^2$ and $R^3$ are not respectively hydrogen and methyl.

2. The compound of claim 1, wherein the compound is

Compound 1

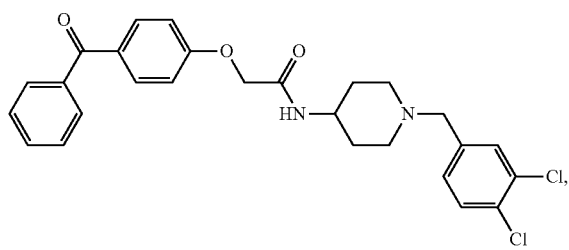

Compound 2

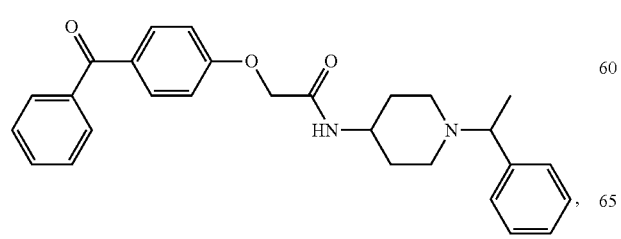

Compound 3

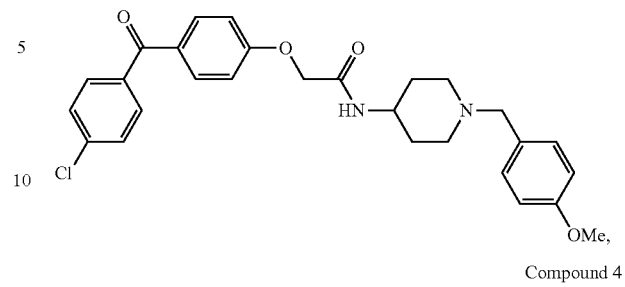

Compound 4

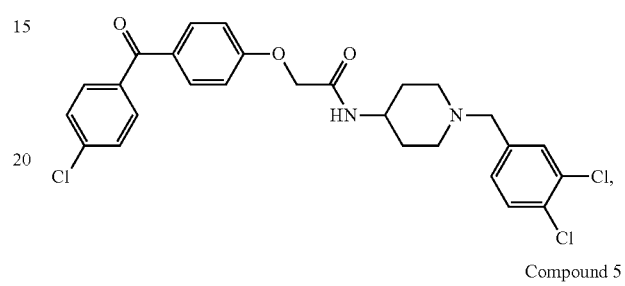

Compound 5

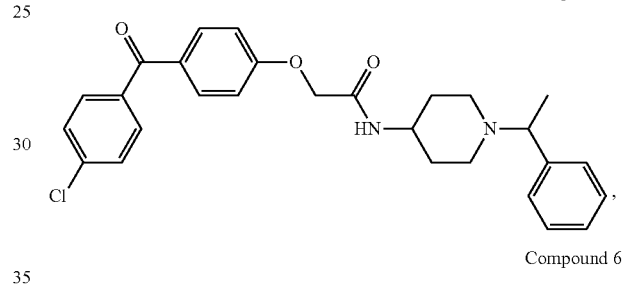

Compound 6

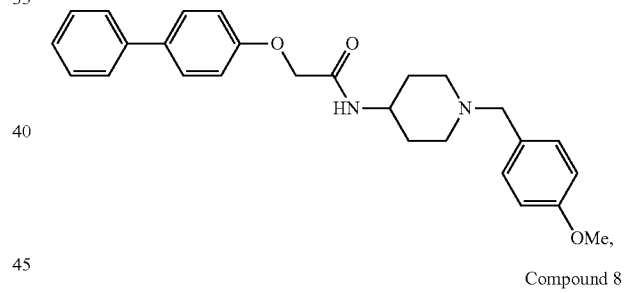

Compound 8

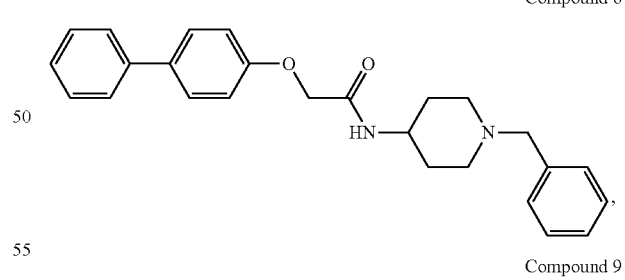

Compound 9

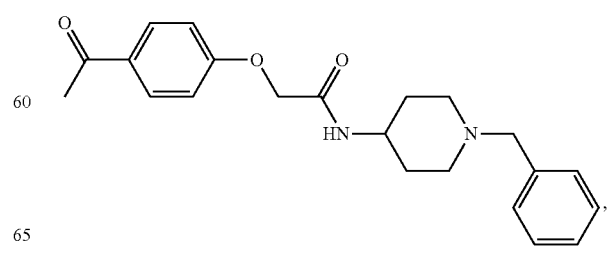

-continued

Compound 10

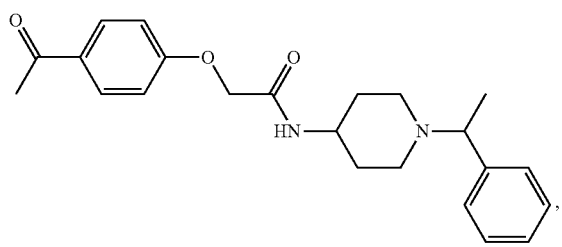

or a pharmaceutically acceptable salt thereof.

3. The compound of claim 1, wherein the compound is

Compound 3

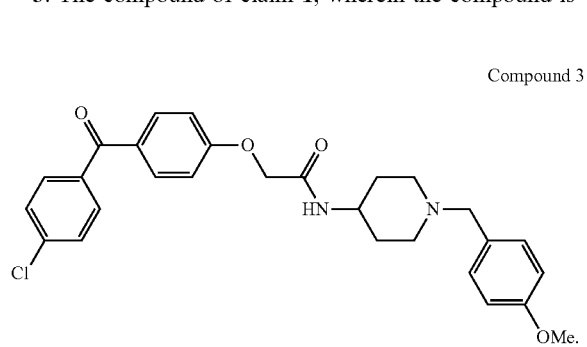

4. The compound of claim 1, wherein the compound is

Compound 5

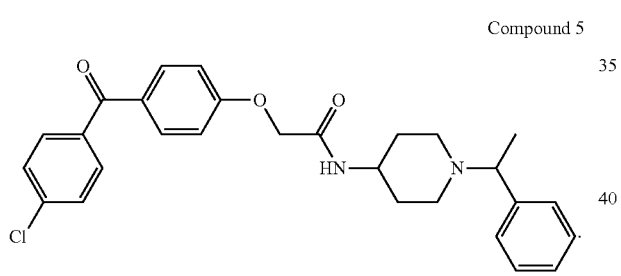

5. A pharmaceutical composition comprising the compound according to claim 1 and a pharmaceutically acceptable excipient, carrier, or diluent.

6. A method for the treatment of inflammation a subject, the method comprising administering an effective amount of the compound according to claim 1.

7. The method of claim 6, wherein the subject has chronic inflammation.

8. The method of claim 6, wherein the subject has diabetes.

9. The method of claim 6, wherein the subject is obese.

10. The method of claim 6, wherein the subject has an infection.

11. The method of claim 10, wherein the subject suffers from sepsis, septic shock, or endotoxemia.

12. The method of claim 6, wherein administering the effective amount of the compound decreases fasting blood glucose in the subject.

13. The method of claim 6, wherein administering the effective amount of the compound inhibits or reduces expression of a proinflammatory cytokine in the subject.

14. The method of claim 6, wherein administering the effective amount of the compound increases expression of an anti-inflammatory cytokine in the subject.

15. The method of claim 6, wherein the compound is

Compound 3

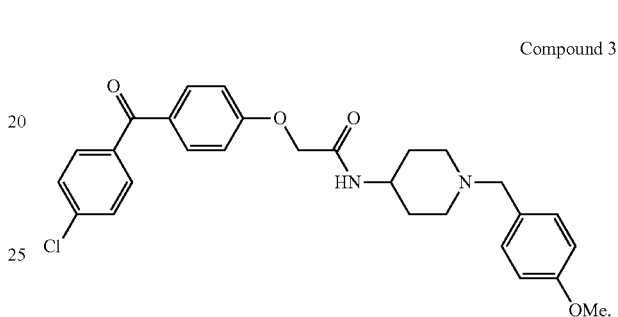

16. A method for the treatment of bone loss a subject, the method comprising administering an effective amount of the compound according to claim 1.

17. The method of claim 16, wherein the subject has periodontitis.

18. The method of claim 16, wherein the subject has type 2 diabetes (T2D)-associated periodontitis.

19. The method of claim 16, wherein administering the effective amount of the compound increases autophagy in osteoclasts.

20. The method of claim 16, wherein the compound is

Compound 3

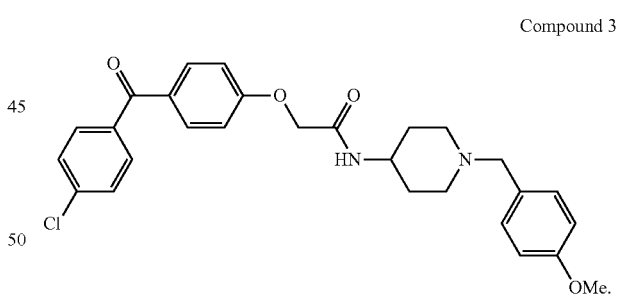

* * * * *